United States Patent [19]

Reich et al.

[11] Patent Number: 5,993,972
[45] Date of Patent: Nov. 30, 1999

[54] HYDROPHILIC AND HYDROPHOBIC POLYETHER POLYURETHANES AND USES THEREFOR

[75] Inventors: Murray H. Reich, Princeton; John Teffenhart, Edison; Jirina Kuzma, Princeton, all of N.J.

[73] Assignee: Tyndale Plains-Hunter, Ltd., Lawrenceville, N.J.

[21] Appl. No.: 09/040,692

[22] Filed: Mar. 18, 1998

Related U.S. Application Data

[63] Continuation-in-part of application No. 08/915,583, Aug. 26, 1997
[60] Provisional application No. 60/024,526, Aug. 26, 1996, and provisional application No. 60/040,094, Mar. 7, 1997.
[51] Int. Cl.$^6$ .................................................... C08G 18/44
[52] U.S. Cl. .................. 428/423.1; 428/375; 428/423.7; 428/424.8; 604/891.1; 2/161.7; 528/76
[58] Field of Search .............................. 428/423.1, 423.7, 428/424.8, 375; 604/891.1; 528/28, 76; 2/161.7

[56] References Cited

U.S. PATENT DOCUMENTS

| | | | |
|---|---|---|---|
| 4,424,305 | 1/1984 | Gould et al. | 525/127 |
| 4,920,172 | 4/1990 | Daoud | 524/502 |
| 5,563,233 | 10/1996 | Reich et al. | 528/76 |

*Primary Examiner*—Rachel Gorr
*Attorney, Agent, or Firm*—Mathews, Collins, Shepherd & Gould, P.A.

[57] ABSTRACT

An improved amphiphilic diol is prepared with a controlled type and amount of alkylene glycol, catalyst, hydrophobic and hydrophilic diol with diisocyanate and water. Critical selection of the type, molecular weight and ratios of hydrophilic to hydrophobic diol, isocyanate to hydroxyl groups, average molecular weight of the diol component, the amount of water in the reaction mixture produces a polyuretheane having high slip, Shore A Hardness values, wet tensile strength and tear strength. This invention also includes uses of the polyurethane in catheters, shaving products, synthetic valves, veins and arteries, stents, ports, shunts and coatings. Preferably, the polyurethane is used in combination with a filler for application to rubber gloves. In addition, dispersions, lotions, gels and solutions can be formed of the polyurethane.

31 Claims, No Drawings

HYDROPHILIC AND HYDROPHOBIC POLYETHER POLYURETHANES AND USES THEREFOR

This is a continuation-in-part of application Ser. No. 08/915,583 filed Aug. 26, 1997 which claims the benefit of U.S. Provisional Application No. 60/024,526 entitled Hydrophilic/Hydrophobic Polyether Polyurethanes filed by the applicants on Aug. 26, 1996 and U.S. Provisional Application No. 60/040,094 entitled Hydrophilic and Hydrophobic Polyether Polyurethanes and Uses Therefor filed by the applicants on Mar. 7, 1997.

BACKGROUND OF THE INVENTION

1. Field of the Invention

The present invention relates to novel amphiphilic polyether polyurethanes which can be low encrustation, swellable, soft, biocompatible, hydrated unitary materials having specific hardness and swellable properties and superior wet tear and tensile strengths for use in intravenous, central venous, dialysis, and cardiovascular catheters, vessels, ports, synthetic veins and arteries, gaskets, medical stents, drug delivery systems, medical, cosmetic, shaving and industrial applications, and which can be blended into hydrophobic elastomers for use in expandable rubber products such as moldings and sealants. The present invention also relates to novel polyether polyurethanes polymers which form spreadable, foams, solutions, dispersions and gels for use as creams, lotions, antiperspirants, emulsifiers, hair conditioners, drug and fragrance delivery systems, coatings of rubber products, and which form breathable, nongreasy, water-resistant, tough, biocompatible, soft, and lubricious films. The present invention also relates to novel hydrophilic polyether polyurethanes which can be coated onto plastics, elastomers and woven and nonwoven cloth into which can be incorporated long and short chain materials such a drug, fragrance and enzyme for imparting controlled release of the material, and which coated material can have extended material and drug release properties. Coated elastomers have improved dry, damp and wet donnability.

2. Description of the Related Art

Hydrophobic and hydrophilic polymers are known and have been used for forming articles such as catheters and body implants with improved swelling properties. U.S. Pat. No. 4,883,699 describes a body implant comprising a multiple phase polymer having one phase with a substantially non-hydrophilic polymer and another phase having a hydrophilic polymer. This swollen and softened material has high strength. The polyurethane is hydrophobic and the hydrophilic material is polyethylene oxide, which is susceptible to leaching, eluting from water. Further, the hydrophobic and hydrophilic materials are blended together, to form a composite. The swelling rate depends upon the water reaching the hydrophilic material and its rate is slowed by the surrounding hydrophobic polymer.

U.S. Pat. No. 4,994,047 ('047 patent) describes a swellable cannula formed of concentric inner and outer hydrophilic and substantially non-hydrophilic layers. The hydrophilic layer is at least ⅔ of the cross-sectional layer of the wall of the cannula. Polyoxyethylene oxide is used as the hydrophilic material. This patent suggests that swelling and softening polymers described in U.S. Pat. Nos. 4,359,558, 4,424,305, 4,454,309, and 4,439,583 may be incorporated into the cannula as hydrophilic materials. The polyurethane-diacrylate polymers are not readily extrudable because the diacrylate monomers form cross-linked networks, possibly even cross-linking the polyurethanes. The '047 patent has the shortcoming that the rate of softening of the inner hydrophilic layer is low, and the use of an outer hydrophilic layer can quickly swell the outside of the cannula, but the diameter of the cannula does not increase until its unstable layer is hydrated.

U.S. Pat. Nos. 3,822,238 and 3,975,350 describe a class of hydrophilic polyether polyurethanes containing about 0.3% of water. The hydrophilic polyurethanes absorb water and are cross-linked. The softness-hardness ratio of the polymers was modified by varying the ratio of soft ($-OC_2 H_4-$) units to hard alkylene units of ($-C_2 H_4 OC_2 H_4-$). The increase in hard units of the polymers increases rigidity of the polymer. An increase in soft units of the polymers results in the polymers being weak, especially in the wet and swollen state. The cross-linked polymer does not lend itself to extrusion into tubing with precise dimensions.

U.S. Pat. No. 4,789,720 of common ownership with the present disclosure overcame some of the above described shortcomings. A hydrophilic polyurethane is formed comprising polyoxyethylene glycol and polyoxypropylene glycol (PPG) and water in the reaction mixture of less than about 0.5% weight percent. The polyurethanes are particularly useful for body implants and feeding tubes. This patent teaches the use of PPG imparts higher dry and wet tensiles to the polymers without substantially diminishing their hydrophilic properties. The use of large amounts of PPG has the drawback of causing considerable blocking of the polymers and reducing the hydrophilicity of the polymer. This reduction in hydrophilicity is disadvantageous in certain applications such as medical device products in which it is advantageous to have high water contents and expansions.

U.S. Pat. No. 5,120,816, of common ownership with the present disclosure, describes a polyurethane resin having improved tear strength in which the amount of water in the reaction mixture is in the range of about 1.0% to about 2.5% weight percent. The reaction product includes a diol formed of a long chain polyoxyethylene glycol and a medium chain polyoxyethylene glycol. The polymers have the shortcoming of not being readily extrudable.

U.S. Pat. No. 5,102,401 ('401 patent) teaches the use of a hydrophobic polymer coextruded over a hydrophilic polymer made with aromatic and aliphatic diisocyanates, in order to reduce the rate of swelling. The swelling rates for the uncoated catheters are 10% in one minute and 21% after 10 minutes. The swelling rate for the hydrophobic coated catheter reached 3.6% in four minutes and 14.7% in 10 minutes. These values were superior to those for a noncoated hydrophilic expandable catheter such as 20 gauge Streamline®, Menlo Care, Inc., Palo Alto, Calif. catheter, described in the preceding patents, which reached 9% swelling in 60 minutes. Typically, nurses and doctors insert and remove needles within two to three minutes, and want the catheter to swell quickly to a high value. Accordingly, the catheters described in the '401 patent have the shortcoming of not swelling fast enough to meet the needs of health-care professionals.

U.S. Pat. No. 5,000,955 describes a thermally reversible gel comprising a polyether polyurethane formed using a mixture of anhydrous polyoxyethylene diols, allylene glycol and an aliphatic diisocyanate. The viscosities of the gel drops as the temperature was increased from room temperature to body temperature. U.S. Pat. No. 5,273,742 describes solutions of polyether polyurethanes for use in eye surgery and arthritic operations.

SUMMARY OF THE INVENTION

It has now been found that careful selection and control of the type and amount of the alkylene glycol, hydrophobic and hydrophilic diols, the type, molecular weight and ratios of the hydrophilic to hydrophobic polyoxyalkylene diol and of isocyanate to hydroxyl groups, the average molecular weight of the diol component, catalyst and the amount of water in the reaction mixture within very small ranges, produces novel amphiphilic and hydrophilic polyether polyurethanes having improved properties such as better biocompatability, high slip, high absorptivity, high Shore A Hardness values, and high wet tensile and tear strengths at low to moderate hydrophilicity. The polyurethane can be formed in a one-shot polymerization in which all ingredients are combined at the same time.

The hydrophilic and amphiphilic polymers of this invention can be used to coat nonwoven polypropylene, polyester, polyethylene, silk, acrylic and polytetrafluoroethylene cloth for use as implanted vascular grafts and in securing implants, the vascular grafts and implants can include a long or short chain material such as for example, a drug, enzyme, anticoagulant, endothilial growth factor, or antibiotic. Preferable materials can include growth factors heparin and tissue plasminogen activator. The rate of release of such a material from the graft or implant is controlled by the hydrophilicity or amphiphilicity and concentration of polymer used for forming the graft or implant. It has also been discovered that certain hydrophilic and amphiphilic polymers can be used to control the release of the material from the polymers. It has been discovered that the hydrophilic and amphiphilic polymers useful for controlling the release of the material from the polymer form hydrogels in the presence of water which can entrap the material. The hydrophilic and amphiphilic polymers of the present invention and combinations thereof can also be used as coatings of an elastomer, plastic, woven cloth, nonwoven cloth and metal to control the rate of release of the material from the coating and substrate.

By definition, all percentages of components are by weight of the reaction mixture unless otherwise specified. According to one embodiment of the present invention, an amphiphilic polyether polyurethane is produced by reacting (A) a diol component comprising a polyoxyalkylene diol, (B) an alkylene glycol, (C) a diisocyanate, (D) water in an amount constituting from about 0.05% to about 0.80% of the combined weight of the reaction ingredients, and (E) catalyst in which the ratio of NCO to OH in the water, diol and glycol mixture is from about 0.70 to about 1.1. The amount of diisocyanate can be from about 1% to about 70% in the reaction mixture.

The resulting polymer is an amphiphilic polyether polyurethane having certain hydrophilic and hydrophobic polyoxyalkylene units, so called soft segments and alkylene units, so-called hard segments connected through urethane linkages. The polymer chain also includes precise amounts of urea groups which originate from the reaction of water with isocyanate groups and which urea groups enhance the dry and wet hardness and tensile strength of the polymer. It has been found that precisely controlling the combination of the different groups in specific proportions produces improved polymer properties such as extrudability, hydrophilicity, high dry and wet tear and tensile strength, flexibility, soft feel, high slip, superior biocompatibility, controlled release of hydrophilic materials and desired expansion in aqueous media.

Preferably, a hydrophilic diol of polyoxyethylene diol and a hydrophobic diol selected from polyoxytetramethylene diol, polyoxypropylene diol, polyether polycarbonate diol and polydimethylsiloxane polyoxyalkylene copolymer is used in the reaction mixture. The polyurethane has a low water absorption value of about 0.1% to about 25% after 24 hours in water and a low expansion value of about 0.1% to about 30% in 24 hours in water.

Substrates can be coated with the amphiphilic polymers having more hydrophobic properties and then biocompatible hydrophilic polymers can be coated over the amphiphilic polymers to obtain biocompatible surfaces and to regulate the leaching of drugs. Also, hydrophobic polymers can be coated over the hydrophilic materials. The hydrophilic polymers can absorb much larger amounts of drug than the amphiphilic polymers which can delay the onset of swelling and of leaching of drugs in aqueous media from the more hydrophilic polymers.

The amphiphilic polymers are specifically adapted as tubing for use as infusion therapy catheters such as intravenous and peripherally inserted catheters, dialysis catheters, cardiovascular catheters, stents, and ports. Also, the amphiphilic polymers can be used as a prime coat over hydrophobic surfaces for hydrophilic materials which do not bond to hydrophobic surfaces. The hydrophilic and hydrophobic polyether polyurethanes of this invention impart enhanced slip, softness, a smooth feel, and biocompatability to the surfaces for use in shaving systems. The polymers can be coated on metal, silicon, elastomers, nonwoven cloth, latex rubber, polyolefins, polystyrene and hydrophilic polymers. Additives such as drugs, fragrances and hydrophilic polymers can be added to the amphiphilic polymer and coatings and solutions of the polymer. Additives can be added to the polymer or in solutions of the polymer such as drugs, fragrances and hydrophilic polymers. The coated material can delay release the additives from the polymer. The hydrophilic polymers can include polyvinylpyrrolidone (PVP) and polyethyleneoxide (Polyox). The additives can be released at a slower rate when the coated material is subjected to an aqueous medium.

In another embodiment of the invention, in particular for certain medical device and cosmetic applications, the amphiphilic polymers are produced from (A) a hydrophobic polyoxypropylene diol having a molecular weight of about 400 to 3000; (B) an alkylene glycol, preferably ethylene glycol and diethylene glycol; (C) diisocyanate; (D) water in the amount comprising about 0.05% to about 0.7%; (E) a catalyst; and (F) a minor portion of a polyoxyethylene diol having a molecular weight of about 400 to about 10,000, the ratio of NCO to OH in the water, diol, and glycol mixture being about 0.60 to about 1.2. The polyurethane has a water absorption value of about 30% to about 60% and an expansion value of about 10% to about 35% after 24 hours in water.

The polymers of this embodiment are particularly useful in and as coatings of medical devices, more specifically for use as infusion therapy catheters, including peripherally inserted catheters, intravenous catheters (IV), central venous, dialysis and cardiovascular catheters, shaving products, mechanical and synthetic heart valves, stents, ports, introducers, valves, shunts, breathable and water-resistant films, cosmetic, medical and therapeutic lotions and creams, and for biocompatible extrudable materials which soften and swell to controlled amounts. Also, the polymers can be used as coatings of elastomers, polymers, glass, including treated and untreated latex rubber and polyolefins such as polyethylene and polypropylene, polystyrene, high impact polystyrene, polyether polyamides, polyurethane, polyurethane-polycarbonate, and the like, metals including stainless steel, aluminum, brass, bronze, copper, silicon, silicon dioxide, nickel and chrome coated metal, brass, bronze, silicon chips, and the like, natural and nonwoven materials. The substrates can be coated with a primer and also can be treated with plasma energy and oxidative gases to enhance bonding of the primer and the topcoat. The amphiphilic polyether polyurethanes of this aspect bond to a wide variety of substrates, impart enhanced slip and biocompatiblity to the surfaces, and also can serve as a primer for more hydrophilic polymers. The amphiphilic polyether polyurethanes are especially valuable for certain medical devices and shaving systems because the polyurethanes of this invention have the advantages of extrudability, improved slip compared to hydrophobic polymers and elastomers including polyurethane, polystyrene, and the like, improved feel and biocompatability, superior dry and wet tensile and tear strengths, and high dry and wet Shore A hardness values. In these cases, low hydrophilicity is needed to reduce expansion upon exposure to water, and unexpectedly minor amounts of hydrophilic diols impart improved biocompatability, slip and compatability with hydrophilic materials compared to polymers without amounts of polyoxyethylene diol.

Alternatively, an amphiphilic polyether polyurethane having improved wet and dry strength comprising the reaction product of a mixture of a hydrophilic diol of polyoxyethylene diol having a number average molecular weight of about 800 to about 20,000, the amount by weight of the hydrophilic diol in the reaction mixture being from about 10% to about 50%; at least one hydrophobic diol selected from polyoxytetramethylene diol, polyoxypropylene diol, polyetherpolycarbonate diol, butylene oxide and polydimethylsiloxane polyoxyethylenecopolymer, an alkylene glycol, an organic diisocyanate; and water in an amount by weight of about 0.20% to about 0.8% of the reaction mixture, the ratio of NCO to OH of the diols, the alkylene glycol and the water being from about 0.70 to about 1.1, wherein said polyurethane has an absorption value of about 30% to about 70% of water after 24 hours in water and an expansion value of about 30% to about 50% after 24 hours in water.

This polyurethane can be used to form a shape structure such as tubing, catheters, valves, introducers, shunts, ports, stents, synthetic veins and synthetic arteries.

In addition, a polyether polyurethane having improved slip is formed from the reaction product of a diol selected from polyoxyethylene diol having a number average molecular weight of from about 400 to about 20,000, the amount by weight of the polyoxyethylene diol in the reaction mixture being at least 60%, polyoxypropylene diol having a number average molecular weight of about 200 to about 4,000, a polyoxytetramethylene diol having a number average molecular weight of about 200 to about 4,000, a polyetherpolycarbonate diol having a number average molecular weight of about 1000 to about 2,200, a polydimethylsiloxane polyoxyalkylene copolymer diol having a number average molecular weight of about 500 to about 3,000, and a polybutylene oxide having a number average molecular weight of about 1000 to about 3,000; an alkylene glycol, a catalyst, an organic diisocyanate; and water in an amount by weight of from about 0.001% to about 0.8% of the reaction mixture, the ratio of NCO to OH of the diols, the alkylene glycols and water being from about 0.85 to about 0.99.

The polyurethane of this aspect can preferably be used to form an article or a coating. The coating can be applied to metal, plastic, woven cloth, nonwoven cloth, rubber, hair, glass, silicon, chlorinated elastomers and nonchlorinated elastomers, razor strips, polymers and silicon chips.

In an alternate aspect of the invention, an amphiphilic polyurethane is formed from a reaction product of a hydrophilic diol of polyoxyethylene diol having a number average molecular weight of about 4,000 to about 10,000 in an amount of about 45% to about 96% and polyoxyethylene diol having a number average molecular weight of about 600 to about 2,000 in an amount of about 0.5% to about 10%, a hydrophobic polyoxyalkylene diol selected from at least one hydrophobic diol such as polyoxytetramethylene diol having a number average molecular weight of from about 600 to about 3,000, polyoxypropylene diol having a number average molecular weight of from about 400 to about 2,500, a polyether polycarbonate diol having a number average molecular weight of about 1,000 to about 2,000, and a polydimethylsiloxane polyoxyalkylene copolymer having a number average molecular weight of about 500 to about 3,000, water in an amount by weight of about 0.005% to about 0.30% of the reaction mixture, the ratio of NCO to OH of the diol and water by about 0.80 to about 0.99. A cream, gel, film, solution coating and dispersion can be formed from the polymer of this aspect.

DETAILED DESCRIPTION OF THE INVENTION

The present invention is based on the discovery that a class of amphiphilic polyether polyurethanes more filly described herein formed from the reaction product of a diol component, an alkylene glycol, a diisocyanate and water are advantageous in medical device, drug delivery, industrial, and cosmetic applications. Infusion therapy catheters and stents formed of the amphiphilic polyurethane have improved soft feel, dry and wet strength integrity, dry and wet Shore A Hardness values, and controlled expansion upon hydration. Creams, foams, lotions, barrier solutions, emulsions, dispersions, and gels formed of the polymers form breathable, spreadable, water-resistant, and non-greasy films for use in medical and cosmetic products. Coatings of the amphiphilic polyether polyurethanes of this invention on hydrophobic surfaces including elastomers and plastics such as natural and silicone rubber, ethylene and propylene co- and terpolymers, high impact polystyrene, butadiene and styrene copolymers and the like, form tenacious bonds that have improved slip. The coatings can be used as a primer for application of high slip hydrophilic polymers. In cosmetic and shaving applications, the polymers of the present invention provide smoothness, enhanced slip, soft feel, improved dry and wet strength, breathability, non-greasy feel, water-resistance, excellent compatability with hydrophilic materials, controlled release of additives and controlled expansion in aqueous media.

A first aspect of the present invention pertains to an amphiphilic polyether polyurethane formed from the reaction product of a diol component which includes a mixture of hydrophilic and hydrophobic polyoxyallylene diols. Preferably, the diol component comprises a hydrophilic diol having a portion of polyoxyethylene diols having a number average molecular weight of from about 400 to about 10,000 of about 15% to about 45% mixed with a portion of hydrophobic diol of about 15% to about 30% having about 10% to about 25% of polyoxytetramethylene diol having a number average molecular weight of about 600 to about 3000 and a hydrophobic diol of about 1.0% to about 25% polyoxypropylene diol having a number average molecular weight from about 400 to about 2500, thereby providing a hydrophobic diol component with a number average molecular weight of about 1000 to about 3000. The diol component is mixed with about 0.5% to about 10% by weight of an alkylene glycol selected from ethylene glycol, propylene glycol, 2-ethyl-1,3-hexanediol, tripropylene glycol, triethylene glycol, 2,-4-pentane diol, 2-methyl-1,3-propanediol, 2,-methyl-1,3- pentanediol, cyclohexanediol, diethylene glycol, 1,4-butanediol, 1,6-hexanediol, cyclohexanedimethanol, dipropylene glycol, and mixtures thereof, an organic diisocyanate and a water equivalent in an amount comprising from about 0.05% to about 0.7% of the reaction mixture in an equivalent mole weight ratio of NCO to OH of the diol, alkylene glycol and water of from about 0.60 to about 1.2.

The polymers formed in this aspect of the invention have intermediate water absorption values of about 30 to about 60% and linear expansion values of about 10% to about 35% after 24 hours in water.

Alternatively about 1% to about 30% of polyetherpolycarbonate diols (PCD) of about 1000 to about 2000 number average molecular weight, polydimethylsiloxane polyoxyalkylene copolymers (PDMSD) of about 500 to about 3000 number average molecular weight, and polybutylene oxides (PBO) having a number average molecular weight of about 1000 to about 2200, preferably 2000, can be used as the hydrophobic diol. The polyether groups in PCD are preferably alkylene glycols, such as for example, butane diol, propylene glycol, dipropylene glycol, pentane diol and hexane diol. The polyoxyalkylene diols in PDMSD are preferably polyoxyethylene diols and polyoxypropylene diols, more preferably polyoxyethylene diols, and most preferably polyoxyethylene diols having a number average molecular weight of about 200 to about 2000, preferably from about 200 to about 1000.

For example, the polyoxyethylene diols are available from Union Carbide Corporation under the trademark and designation Carbowax, such as Carbowax® 3360, Carbowax® 4500, Carbowax® 8000, and Carbowax® 1450 wherein numbers represent the number average molecular weight.

Polyoxypropylene diols are available from various sources such as from ARCO under the trademark of NIAX® PPG 1025, PPG-425, PPG-725, PPG 4025 and PPG 2025 and Acclaim 2200 and Acclaim 4200 wherein the numbers represent the number average molecular weight except in the case of Acclaim where the number average molecular weight values are 2000 and 4000 respectively. For example, polyoxytetramethylene diols are available from E. I. Dupont de Nemours as Terathanes 600, 1000, 1400, 2000, 2900 and from Nippoly America as CD250. Polyetherpolycarbonate diols are available, for example, from BASF as PolyTHFCD-1000 and PolyTHF CD-2000, CD4200, CD4201 and Nippollan 980 and Nippollan 981 are available from Nippoly America Corp. For example, polydimethylsiloxane polyoxyethylene copolymers are available from OSI as Silwets, Dow Corning as Q4-3667, Q2481, Q2 5211 and from GE as GE Silicones as 1161-11-925, 1161-11-926, 1161-1032, 1161-11-928, and polybutylene oxides are available from Dow Company as XAS.1096.01 and XAS 1096.05.

Alternatively, block copolymers of ethylene oxide and propylene oxide having a number average molecular weight of about 1000 to about 2500 can also be used in the reaction. For example, a propylene oxide terminated block of ethylene glycol manufactured by BASF under the tradename Pluronic R and an ethylene oxide terminated block of propylene glycol manufactured by BASF under the tradename of Pluronic can be used for the polyoxyalkylene diol in the reaction. Examples of the block copolymers of the sequential addition of ethylene oxide and propylene oxide to ethylene diamine are made by BASF under the tradename of Pluronics and Pluronic R such as F64, F127, L35, L92, F68, L82, 17R2 and 25R2.

Preferably the polyoxyalkylene diol used to form the amphiphilic polyether polyurethanes of this invention are formed from a combination of a hydrophilic diol of about 5% to about 20% of a polyoxyethylene diol (PED) of a number average molecular weight from about 400 to about 2000, referred to as low molecular weight, and about 10% to about 25% of a PED of a number average molecular weight from about 2500 to about 5000, referred to as high molecular weight, with hydrophobic diols of about 1% to about 25% of a polyoxypropylene diol having a number average molecular weight of about 400 to about 2500, preferably from about 1000 to about 2000, and from about 10% to about 30% of a polyoxytetramethylene diol having a number average molecular weight of about 600 to about 2500, preferably from about 1000 to about 2000. Preferably, the amount in the reaction mixture of the hydrophobic polyoxyalkylene diol is from about 10% to about 25%.

Preferably, the ratio of the high to low molecular weight polyoxyethylene diol is from about 2/1 to about 0.5/1 more preferably from about 1.5/1 to about 0.9/1. Preferably the average molecular weight of the polyoxyalkylene diol component, including the hydrophilic and hydrophobic diol, is from about 1500 to about 3000. Preferably, the amount of polyoxyalkylene diol used in the reaction is from about 40% to about 70%, more preferably from about 45% to about 60%. Preferably, the amount of polyoxypropylene diol used in the reaction mixture is from about 3% to about 20%, more preferably in the amount of about 4% to about 15% of the reaction mixture, and most preferably in the amount of about 5% to about 10% of the reaction mixture.

Alternatively, the polyoxyethylene diols in the reaction mixture can be about 20% of a polyoxyethylene diol having a number average molecular weight of about 6000 to about 10,000 and about 10% to about 25% of a PED of a number average molecular weight of from about 2500 to about 5000. The increased molecular weight of the hydrophilic diol in the amphiphilic polyurethane imparts higher hydrophilicity, higher water absorption, higher water expansion, higher dry Shore A Hardness values and lower wet Shore A Hardness values.

Alternatively, the polyoxyethylene diol can include about 12% to about 18% of a polyoxyethylene diol having a number average molecular weight of about 400 to about 1000 and about 10% to about 15% of polyoxyethylene diol having a number average molecular weight from about 1000 to about 2000. Polyoxyethylene diols having a number average molecular weight of about 400 to about 1000 can be used in combination with about 12% to about 20% of polyoxypropylene diol, in order to obtain high dry and wet tear and tensile strength polymers with enhanced slip, soft and smooth feel, low expansion and water content after immersion in water, and improved bondability to hydrophobic surfaces.

Alkylene glycols are available from chemical supply houses. For example, ethylene glycol and diethylene glycol are available from Aldrich Chemical Company.

Preferably, the amount by weight of the alkylene glycol used in the reaction mixture is from about 3% to about 20%, and more preferably from about 4% to about 12%. Preferably the alkylene glycol is dipropylene glycol, triethylene glycol, diethylene glycol, 1,4-butanediol, 1,6-hexanediol, and ethylene glycol. For some products, the preferred amount of the ethylene glycol is from about 4% to about 10%.

The ratio of NCO to OH of the hydroxyl groups from the diols, alkylene glycol, and water in the reaction mixture is preferably in the range from about 0.80 to about 1.0 and most preferably from about 0.90 to about 0.99. The sum of all ingredients, including the diols, glycols, water, and diisocyanate in the reaction mixture totals 100 parts by weight.

The diisocyanate used in the present invention can include both aliphatic and aromatic types and mixtures thereof. Still more preferably, isocyanates are methylene bis(-cyclohexyl-4-isocyanate) and methylene bis(-phenyl-4-isocyanate), and more preferably is methylene bis(cyclohexyl-4-isocyanate). Other examples of diisocyanates are trimethyl hexamethylene diisocyanate and isophorone diisocyanate. Representative examples of the preferred aliphatic diisocyanates include, but are not limited to tetramethylene diisocyanate, hexamethylene diisocyanate, trimethylene diisocyanate, trimethylene hexamethylene diisocyanate, cyclohexyl 1,2-diisocyanate, cyclohexylene 1,4-diisocyanate, and aromatic diisocyanates such as methylene bis(phenyl-4-isocyanate) (MDI), 2,4-toluene diisocyanates and 2,6-toluene diisocyanates. Also suitable are the isocyanate equivalents which form urethane linkages as exemplified by nitrile carbonates, such as adiponitrile carbonate of the formulas described in U.S. Pat. No. 4,810,543 of common ownership therewith, hereby incorporated by reference into this application. The amount of diisocyanate in the reaction mixture can vary from about 1% to about 70%, preferably from about 20% to about 60%, and more preferably from about 30% to about 55%. The polymers are prepared by reacting the polyoxyalkylene diols with the diisocyanates.

In forming the polyurethane of the present invention, the diol and glycol components are formed into a homogeneous mixture which is then reacted with diisocyanate, the reaction is catalyzed with known catalysts such as tin salts and organic tin esters such as bismuth neodecanate, bismuth octoate, dibutyl tin dilaurate and stannous octoate. The amount of catalyst in the reaction mixture is about 0.5 cc to about 6 cc per pound of reactants.

In an alternative method, a semi-batch reaction is used in which the diols are heated and the mixture is analyzed for water; and a predetermined amount of additional water is added. The catalyst is added to the mixture. Diisocyanate is added to another reactor and heated under dry nitrogen. Two streams of heated reactive mixtures are mixed in a predetermined ratio in a tube and allowed to flow into a pan, extruder, static and dynamic mixers, trough, conveyor belt or other container. The mixture is allowed to react further at a temperature from about 20° to about 140° C., preferably from about 30° to about 135° C., more preferably from about 40° to about 130° C., and most preferably from about 60° to about 120° C. for about one minute to about one week, preferably from about five minutes to about 240 minutes, more preferably from about 10 minutes to about 120 minutes. The reaction can be completed at room temperature.

The polymers can be cut into strips by a bandsaw and then granulated into small flakes or granules using a granulator and chipper. The particle size of the granules depends upon the mesh size of the screen. The blocks of polymers can be granulated and then cryogenic ground or pulverized to powder. Alternatively, the reaction mixture can be fed to continuous trough-type dryers and extruders, chopped into granules, and then fed to a pulverizer, or used without farther treatment.

It has surprisingly been found that controlling several factors in the reaction mixture provides polymers with valuable properties for effective use in medical, cosmetic, and industrial applications, more specifically for use in medical devices and as coatings of metals, glass, hair, elastomers and plastics. It has been found that controlling precisely the type, total amount and molecular weight of hydrophilic and hydrophobic diols, type and amount of alkylene glycol, ratio of isocyanate to hydroxyl groups and total amount and number average molecular weight of polyoxyalkylene diol provide properties of the polymer for effective use in tubing for medical devices, industrial applications, and coatings. It has been found experimentally, for example, that a polymer with a low to moderate amount of urea groups which is tough, extrudable, flexible, biocompatible, with requisite wet and dry hardness values and desired expansion in water can be obtained by controlling the urea groups, number average molecular weight of the polyoxyalkylene diol, ratios of hydrophobic to hydrophilic diol and high to low molecular weight hydrophilic diol of PED, type and amount of the hydrophobic polyoxyallylene diol, and type and amount of alkylene glycol and catalyst. It has been found that too few urea groups in the polymer can produce soft, low tensile polymers, and too many urea groups in the polymer can yield hard, less flexible and stable polymers. The polymers of this aspect of the invention have the optimum and preferred balance of properties for use in certain medical devices and cosmetic and shaving applications, especially for components, accessories and catheters for infusion therapy, biliary and urinary stents and as coatings.

Further it has unexpectedly been found that the amphiphilic polyether polyurethanes of this aspect are extrudable into strong and tough tubing which have expansion values in water from about 10% to about 40%, preferably from about 11% to about 35%, water contents after 24 hours in water from about 30% to about 55%, dry tensile strengths from about 2000 to about 4500 pounds/square inch, wet tensile strengths from about 800 psi to about 3000 psi, preferably from about 1000 psi to about 2500 psi, wet tear strengths from about 100 to about 300 psi, wet Shore A Hardness values from about 50 to about 90, preferably from about 55 to about 85, and dry Shore A Hardness values from about 60 to about 95.

It has been discovered that polymers having at least about 30% to about 40% PED having a number average molecular weight of about 3000 to about 9000 have water contents in 24 hours of about 35% to about 55% and have low receding water contact angles, preferably, less than about 45%, more preferably less than 35%.

The polymers of this aspect of the invention are valuable for medical device applications which require biocompatibility, low encrustation, superior antithrombogenicity, melt strength, flexibility, low kinkability, extrudability, low initial rates of swelling. A tube formed of the polymer of this aspect has controlled inner diameter expansion of about 20% to about 30% at body temperature of about 37° C. The polymer can be used in medical device applications such as infusion therapy catheters, central venous and intravenous catheters, peripherally inserted catheters, dialysis catheters, valves, introducers, shunts, ports, drainage catheters, urinary, biliary and other medical stents, synthetic veins and arteries, and regulation of drug delivery.

The polymers of this aspect can be used to coat materials including, silicon, silicon dioxide, steel, brass, bronze, aluminum, iron, and nickel-coated and chrome-plated surfaces, nonwoven and woven materials, and to coat polymers and elastomers, for example, latex rubber, butadiene/ nitrile and other synthetic and natural rubbers, butadiene/ styrene copolymers, silicone, polyurethane, polyether polyamides, polyurethane polycarbonates, polyolefins, polystyrene, high impact polystyrene, polyphenylene oxides, hydrophilic and biodegradable polymers, and mixtures thereof, and chlorinated, plasma and gas-treated hydrophobic surfaces, to improve slip, smoothness, softness, biocompatability, breathability of the materials. For example, hydrophobic polyurethane catheters can be coated with the polymers of this aspect to facilitate insertion and withdrawal of catheters.

It has been found that amphiphilic polyether polyurethanes comprising about 0.1% to about 30% polyetherpolycarbonates diols and polydimethylsiloxane polyoxyalkylene copolymers are less blocky than polymers formed without these diols.

The polymers of this aspect can be coextruded with hydrophobic and hydrophilic polymers in order to control the slip, biocompatibility, and expansion of the surface and can be blended with hydrophobic plastics and elastomers. The polymers can be used in the manufacture of medical devices such as cardiovascular catheters, cardiovascular circulatory pumps, invertebral discs, absorbent packaging, shaving systems, razors, blood oxygenators, intrauterine devices, oral delivery systems, and high slip coatings for silicon computer chips and sorting arrays used in the computer industry and for medical devices, protective coatings for automotive and electronic parts, cosmetic applications, paint additives and thickening additives for water-soluble paints and to increase breathability of nonwoven polyolefins while retaining anti-strike properties.

A second aspect of the present invention pertains to amphiphilic polyether polyurethanes comprising the reaction product of a polyoxyalkylene diol having a portion of about 5% to about 70% of a hydrophobic polyoxyalkylene diol selected from a polyoxypropylene diol and a polyoxytetramethylene diol having a number average molecular weight from about 400 to about 3000, a portion of a hydrophilic diol of about 1% to about 40% of a polyoxyethylene diol having a number average molecular weight of from about 400 to about 20,000, an alkylene glycol selected from ethylene glycol, propylene glycol, 2-ethyl-1,3-hexane diol, tripropylene glycol, 1,6-hexane diol, triethylene glycol, 2,-4-pentane diol, 2-methyl-1,3-propanediol, cyclohexanediol, 1,4-butane diol, cyclohexanedimethanol, dipropylene glycol, 1,5-pentane diol and diethylene glycol, an organic diisocyanate and a water equivalent in an amount comprising from about 0.10% to about 0.70% by weight of the reaction mixture in an equivalent mole weight ratio of NCO to OH of the hydroxyl groups of the diols, alkylene glycol and water in the reaction mixture from about 0.7 to about 1.1.

Preferably the number average molecular weight of the polyoxyalkylene diol component is from about 1000 to about 3000. Preferably, the hydrophobic polyoxyalkylene diol is a polyoxypropylene diol having from about 1000 to about 2200 number average molecular weight. Preferably the amount of polyoxypropylene diol in the reaction mixture is from about 10% to about 60% and most preferably from about 15% to about 50%.

Preferably the number average molecular weight of the polyoxyethylene diol in the reaction mixture is from about 800 to about 10,000. Preferably a polyoxyethylene diol having a number average molecular weight of about 1,000 to about 2,000 is used in the reaction mixture in an amount of about 1% to about 30%, preferably from about 2% to about 25%, still more preferably from about 3% to about 20%, and most preferably from about 4% to about 15%. Preferably the NCO to OH ratio is from about 0.80 to about 1.0, more preferably from about 0.90 to about 0.99.

The amount of diisocyanate used in the reaction mixture can vary from about 10% to about 70%, preferably from about 20% to about 60%, and more preferably from about 30% to about 55%. The polymers are prepared by reacting the polyoxyalkylene diols with the diisocyanates. Preferably, the dissocyanates are methylene bis(-cyclohexyl4-isocyanate) and methylene bis(-phenyl-4-isocyanate). Most preferably the isocyanate used in the reaction mixture is methylene bis(-cyclohexyl-4-isocyanate).

Alternatively about 4% to about 15% of polyoxyethylene diol having a number average molecular weight from about 3,000 to about 10,000 can be used in the reaction mixture.

Alternatively about 5% to about 25% of a hydrophobic polyoxytetramethylene diol having a number average molecular weight from about 1000 to about 2000 can be used as the hydrophobic diol in the reaction mixture.

Alternatively about 1% to about 30% of hydrophobic diols having a number average molecular weight from about 1000 to about 2400, selected from polyether polycarbonate, comprising hexane and butane diol, polydimethylsiloxane polyoxyalkylenecopolymer, having a number average molecular weight from about 500 to about 3800, preferably from about 600 to about 3000, and preferably polyoxyethylene copolymer, and polybutylene oxide, and mixtures thereof can be used in the reaction mixture.

The amphiphilic polymers formed in this aspect have an expansion in water of about 0.1% to about 20%, preferably from about 0.2% to about 16%, and have water contents after 24 hours in water at room temperature of about 0.1% to about 45%, preferably from about 0.2% to about 40%, more preferably from about 0.5% to about 35%, and most preferably from about 0.5% to about 25%. Preferably the polymers have dry Shore D Hardness values from about 10 to about 70, and wet Shore A Hardness from about 20 to about 98. For applications, such as stents, adhesives, coating, gaskets and valves, the dry Shore A Hardness can be controlled to about 20 to about 40, and about 40 to about 70 for the other applications, such as catheters and coatings. The preferred wet Shore D Hardness value is from about 30 to about 80, and more preferably from about 40 to about 70 for applications, such as certain types of coatings, catheters, hot melt adhesives and gaskets. Preferably the tensile strength of the polymer after 24 hours in water is at least about 800 psi, more preferably at least about 1200 psi.

Nonswellable catheters preferably have expansions in water of less than about 10%, more preferably less than about 5%, and most preferably less than about 3%, and have dry hardness A values of about 85 to about 97, and wet hardness A values of about 50 to about 70. The ratios of the hydrophobic and hydrophilic polymers used in the reaction mixture can be adjusted to obtain the desired dry and wet hardness values to form a polymer without appreciable swelling.

An amount of about 30% to about 50% of a hydrophobic diol of polyoxypropylene diol forms an amphiphilic polyurethane having expansion values of less than about 10% and water contents of less than about 20% after immersion in water for 24 hours.

The hydrophilicity of the polymers formed by this combination of reaction ingredients can be increased from about 2% to about 10% water content after water immersion to about 10% to about 20% without significant losses in wet tear and tensile strength, by replacing a number average molecular weight polyoxyethylene diol (PED) of 1,000 to 2,000 with a comparable amount of about 5% to about 20% of a PED having a number average molecular weight from about 3200 to about 10,000.

Polymers comprising at least about 5% of higher number average molecular weight of 3,200 to 10,000 PED have improved slip and extruded products of these polymers have greater resistance to collapse and are less tacky after being subjected to temperatures above 40° C. and ethylene oxide sterilization.

Polymers comprising about 4% to about 15% of a polyoxyethylene diol having a number average molecular weight of about 800 to about 2000, and about 8% to about 25% each of a mixture of polyoxypropylene diol, polyetherpolycarbonate diol, and polyoxytetramethylene diol have dry tensile strengths greater than about 3000 psi, and retain a high proportion of the tensile strength after 24 hours in water. The polymers have wet tensile strengths greater than about 2000 psi, preferably greater than about 2500 psi, and still more preferably tensile strengths greater than about 2800 psi.

Preferably the number average molecular weight of the hydrophobic polyoxyalkylene diol is from about 1000 to about 2400. Preferably the amount of the hydrophobic diol in the reaction mixture is from about 20% to about 60%, more preferably from about 30% to about 50%.

Preferably, the amount of the alkylene glycol used in the reaction mixture is in the amount about 1.5% to about 30%, preferably from about 3% to about 20%, and more preferably from about 4% to about 15%, and most preferably from about 5% to about 10%. Preferably the alkylene glycol is triethylene glycol, dipropylene glycol, butane diol, hexane diol, diethylene glycol, and ethylene glycol, and more preferably the alkylene glycol are hexanediol and ethylene glycol; the amount of the ethylene glycol in the reaction mixture is from about 4% to about 10%. The amount of water in the reaction mixture is preferably from about 0.10% to about 0.5%, and more preferably from about 0.15% to about 0.45%.

The polymers of this aspect of the present invention and blends with hydrophilic and hydrophobic polymers described below are specifically adapted for use in medical device applications such as accessories, components, and infusion therapy catheters, midline catheters, intravenous catheters, softenable, nonswellable catheters, synthetic heart valves, veins, and arteries, scar flatteners, cardiovascular therapy catheters, stents, ports, dilators, and dialysis catheters and the like, and for shaving products. The polymer can be used to coat metal, elastomers, polymers, nonwoven cloth, and mixtures thereof The polymers of the second aspect of this invention can be used to coat hydrophobic materials including but not limited to latex rubber, polyolefins, polystyrene, high impact polystyrene, nitrile and butadiene/styrene copolymers, nonwoven cloth and hydrophilic polymers. The polymers can be used to coat metals such as for example stainless steel, iron, silicon, silicon dioxide, brass, copper, bronze, nickel and chrome plated metals. The polymers can be used to prime hydrophobic substrates over which a topcoat of a more hydrophilic polymer is coated.

It has been found that amphiphilic polyether polyurethanes formed of this aspect comprising about 0.1% to about 30% polydimethysiloxane polyoxyethylenecopolymers in the reaction mixture are soft, do not block and have improved oxidative resistance. Polymers comprising about 0.5% to about 30% of polyetherpolycarbonate diols and mixtures thereof in the reaction mixture have been found to be less blocking than those with equal amounts of polyoxypropylene diols, have superior dry and wet stress-strain properties and improved oxidative resistance.

The polymers are valuable for medical device, industrial, cosmetic, and shaving applications because of their soft feel, flexibility, toughness, breathability, excellent dry and wet strength, low expansion, superior biocompatability, low kinkability, compatability with other hydrophilic materials, low drug release rates and high slip. The polymers are especially useful as scar flatteners, for softenable, non-swellable catheters, and cosmetic and shaving applications because of their soft feel, breathability, superior compatability with more hydrophilic materials, improved slip compared to prior art hydrophobic polymers, superior dry and wet tensile and tear strength, and low expansion. The polymers can be coated over hydrophobic surfaces comprising hydrophilic materials to delay and control the release of additives. For example, a coating of an amphiphilic polymer over polystyrene comprising hydrophilic polymers can reduce the elution rates in the presence of water in the hydrophilic polymers and materials.

The polymers can be used with and without fillers for incorporating fragrance and coating latex rubber and synthetic rubber goods, including gloves, condoms, and coating fingers, because of improved donnability, breathability, hypoallergenicity, smoothness, and enhanced slip without use of powder and pretreatment. Chlorinated and nonchlorinated gloves can comprise natural and synthetic copolymers and terpolymers of dienes, styrene, acrylonitrile, and methacrylic acid. To further enhance damp and wet donnability, the polymers can be mixed in a concentration of polymer of about 0.01% to about 10% preferably about 0.3% to about 3.5% in a coating solution with about 0.01% to about 20%, based on polymer solids, of hydrophilic polymers such as polyvinylpyrrolidone and polyoxyethyleneoxide, and with polymers made with polydimethylsiloxane polyoxyethylene copolymers, as described in this aspect and in the fourth and fifth aspects of this invention described below.

The polymers can be treated with chlorine, plasma energy and oxidative gases to obtain more hydrophilic surfaces.

The polymers of the second aspect of the invention can be used for delivery systems, and to coat silicon chips used for computer and medical devices. By using primers having different hydrophilicity, as described in this invention, the surface properties can be modified. It is desirable in analyzing certain proteins to apply a hydrophilic polymer over silicon metal as a primer, and then topcoat with a less hydrophilic polymer, such as one described in aspects one and two. It may be valuable to form a device using the low expansion polymers described in aspects one and two, eliminating the need to coat the silicon metal. Elution rates with chemicals, drugs and protein, cells, enzymes incorporated into hydrophilic polymers can be controlled by coating a hydrophobic coating over the hydrophilic coating. And drugs can be incorporated into an aqueous media, and their reaction with enzymes, cells, and proteins incorporated into the coating can be observed and measured using computer chips and lasers.

A third aspect of the present invention relates to amphiphilic polyether polyurethanes comprising the reaction product of a polyoxyalkylene diol having a hydrophilic diol of polyoxyethylene diol of about 10% to about 50% having a number average molecular weight of about 800 to about 20,000, hydrophobic polyoxyalkylene diol of about 1% to about 30% having a number average molecular weight of from about 400 to about 3,000 selected from polyoxypropylene and polyoxytetramethylene diols, and mixtures thereof, to provide a number average molecular weight for the polyoxyethylene diol component of about 4000 to about 6500,an alkylene glycol selected from ethylene glycol, propylene glycol, 2-ethyl-1,3-hexane diol, tripropylene glycol, triethylene glycol, 2,-4-pentane diol, 1,5-pentane diol, 1,4-butane diol, 1,6-hexane diol, 2-methyl-1,3-propanediol, cyclohexanediol, cyclohexanedimethanol, dipropylene glycol, and diethylene glycol, a catalyst, an organic diisocyanate and a water equivalent in an amount comprising from about 0.03% to about 0.80% by weight of the reaction mixture in an equivalent mole weight ratio of NCO to OH of from about 0.7 to about 1.1.

The polymers formed in this aspect of the present invention have high water absorption values of about 30% to about 60% and high expansion values of about 30% to about 50% after 24 hours in water.

Preferably the hydrophobic polyoxyalkylene diol is polyoxypropylene diol having a number average molecular weight from about 1000 to about 2000. The amount of the hydrophobic polyoxyalkylene diol preferably in the reaction mixture is from about 3% to about 20%, and most preferably from about 4% to about 15%.

Preferably a major portion of the hydrophilic polyoxyalkylene diol is polyoxyethylene diol having a number average molecular weight from about 3000 to about 10,000, more preferably from about 7000 to about 9000. Preferably the amount used in the reaction mixture of this polyoxyethylene diol is preferably from about 20% to about 45% of the reaction mixture, and most preferably from about 25% to about 40% by weight of the reaction mixture.

Preferably a minor portion of the hydrophilic polyoxyalkylene diol is a polyoxyethylene diol having a number average molecular weight from about 800 to about 2000. Preferably the amount of this polyoxyethylene diol in the reaction mixture is from about 1% to about 20%, more preferably from about 2% to about 15%.

Preferably, the amount of water in the reaction mixture by weight is from about 0.02% to about 0.6%, more preferably from about 0.04% to about 0.45%. For some applications, the amount of water is about 0.05 to about 0.20% and the catalyst is about 0.8 cc to about 5.0 cc per pound of reactants.

Preferably, the NCO/OH ratio is from about 0.85 to about 1.0 and more preferably from about 0.88 to about 0.99.

The amount of diisocyanate in the reaction mixture for this aspect is from about 5% to about 60%, preferably from about 20% to about 55%, more preferably from about 30% to about 50%. Preferably the diisocyanate is methylene bis (-cyclohexyl-4,4'-isocyanate). Other representative diisocyanates which can be used in the reaction mixture are tetramethylene diisocyanate, hexamethylene diisocyanate, and aromatic diisocyanates, such as 2,6-tolylene dIisocyanate and methylene bis (-phenyl-4, 4-isocyanate).

Alternatively about 1% to about 30% of hydrophobic diols can be used in the reaction mixture. The hydrophobic diols have a number average molecular weight from about 500 to about 3500. The hydrophobic diols can be selected from polyether polycarbonate diols formed with hexane diol and butane diol, polydimethylsiloxane polyoxyethylenecopolymer having a number average molecular weight from about 500 to about 3200, preferably from about 600 to about 3000 and polybutylene oxide, and mixtures thereof can be used in the reaction mixture.

The polymers of this aspect have expansion values in water of about 20% to about 75%, and water contents after 24 hours immersion in water of about 30% to about 75%, and dry Shore D Hardness values of about 40 to about 70, and wet Shore A Hardness values of about 20 to about 98. The degree of hardness and expansion is related to the amount in the reaction mixture of polyoxyethylene diol having a number average molecular weight from about 6000 to about 10,000. Preferably, the water contents are from about 30% to about 70% and expansion values in water are from about 25% to about 65%. Preferably the polymers have a wet tensile strength of at least about 800 psi.

The polymers can be used as infusion therapy catheters, such as for example, acute and central venous catheters, dialysis catheters, subcutaneous ports, and peripherally inserted catheters, biliary, coronary and urinary stents, as gaskets, plugs, in urinary products, and as coextrusions and coatings of hydrophobic surfaces including chlorinated and nonchlorinated latex rubber, butadiene/styrene copolymers, high impact polystyrene, blends of polystyrene with other polymers, polyurethane, polyurethane-polycarbonate, polyolefins, and the like to provide a tenacious biocompatible and expandable coating having improved slip. The coating with and without filler can also act as a primer for more hydrophilic polymers including polyether polyurethanes. Coating applications include powder-free exam gloves, surgeon's gloves, industrial and electronic gloves, strips for razors, infusion therapy, dialysis and cardiovascular catheters, stents, and other medical devices.

In a fourth aspect of the present invention, amphiphilic polyether polyurethanes are used to form high slip, high water absorptive, hypoallergenic and biocompatible coatings. High slip is used to refer to a polymer having a coefficient of friction value of less than about 0.1. The high slip polymers can be used to make dip coated, extruded, coextruded, and molded products with high slip, absorptive, hypoallergenic and biocompatible properties. The polyurethane comprises the reaction product of a mixture of a diol component comprising a polyoxyalkylene diol selected from polyoxyethylene diol having a number average molecular weight of from about 400 to about 20,000, polyoxypropylene glycol having a number average molecular weight of about 200 to about 4,000, a polyoxytetramethylene diol having a number average molecular weight of about 200 to about 4,000, a polyetherpolycarbonate diol having a number average molecular weight of about 1000 to about 2,200, a polydimethylsiloxane polyoxyethylene copolymer diol having a number average molecular weight of about 500 to about 3,000, and mixtures thereof, a catalyst an organic diisocyanate and water in an amount from about 0.001% to about 0.70% of the reaction mixture in an equivalent weight ratio of NCO to OH of from about 0.80 to about 1.05.

The polyoxyalkylene diol in this aspect is preferably polyoxyethylene diol. Preferably the amount of alkylene glycol by weight in the reaction mixture is about 0.05% to about 5.0%. Alternatively, the alklene glycol can be omitted. Preferably the polyoxyethylene diol has a number average molecular weight from about 1000 to about 20,000, more preferably from about 3,200 to about 16,000, still more preferably from about 4,500 to about 10,000 and most preferably from about 6,000 to about 9,000. Preferably the alkylene glycol is ethylene glycol and diethylene glycol, more preferably diethylene glycol. Preferably the amount of water in the reaction mixture is from about 0.01% to about 0.7%, and most preferably from about 0.03% to about 0.45%. Preferably the equivalent weight ratio of NCO to OH used in the reaction mixture is from about 0.55 to about 1.0, more preferably from about 0.88 to about 0.99. Alternatively, the NCO/OH ratio is from 0.50 to about 0.65 and the amount of water in the reaction mixture is from about 0.5 to about 0.75%.

The amount of diisocyanate by weight in the reaction mixture can vary from about 2% to about 70%, preferably from about 3% to about 40%, and more preferably from about 3% to about 25%. The polymers are prepared by reacting the alkylene glycols, polyoxyalkylene diols with the diisocyanates. Preferred isocyanates are methylene bis(-cyclohexyl-4-isocyanate) (DW) and methylene bis(-phenyl-4-isocyanate) (MDI).

The reaction mixture can include a polybutylene oxide having a number average molecular weight of about 1000 to about 3,000, an alkylene glycol selected from ethylene glycol, propylene glycol, 2-ethyl-1,3-hexane diol, tripropylene glycol, triethylene glycol, 2,-4-pentane diol, 2-methyl-1,3-propanediol, cyclohexanediol, cyclohexanedimethanol, dipropylene glycol, and diethylene glycol.

For use as high slip, high water absorptive and biocompatible absorbents, coatings and gels-forming polymers, preferably the amount of water by weight in the reaction mixture is about 0.02% to about 0.25% and for use as tough coatings, and in high slip, biocompatible, extrudable, coextrudable, strong products, preferably the amount of water is about 0.25% to about 0.50%.

Polymers having high slip and water absorptive properties can be used as gels, absorbents and coatings of nonwoven cloth, rubber products and medical devices and can be produced with PED of about 4,000 to about 12,000, about 0.8 cc to about 5.0 cc of catalyst per pound of reactants at 0.88 to about 0.99 NCO/OH ratio. The reaction ingredients can be reacted preferably at 70° C. to about 120° C. for twenty minutes to about three hours. Alternatively, the alkylene glycol is omitted and alternatively the reactants are postcured at about 15° C. to about 70° C. for about 0.5 hours to about four weeks. Preferably, the catalyst is selected from dibutyl tin dilaurate, stannous octoate, bismuth neodecanate and bismuth octoate, and preferably the PED has a number average molecular weight of about 6,000 to about 10,000. The polymers have a viscosity in water at 2% concentration of at least 500 cps, preferably at least 5,000 cps and a viscosity at 3% concentration in 60/40 propylene glycol/water of at least 50 cps, more preferably at least 100 cps, and most preferably at least about 300 cps. The polymers can be insoluble in water and solvent. For certain applications, such as absorbents and some high slip coatings, preferably the polymers are insoluble in water and have a viscosity of at least 500 cps in 60/40 propylene/glycol at 3% concentration.

The hydrophilic polymers of this aspect can be coated and coextruded over metals, plastics, and rubber to modify surface characteristics and obtain high slip and biocompatible surfaces for use in medical devices, shaving and cosmetic, and industrial applications. At higher ratios of about 0.90 to about 0.99, of NCO to OH and higher levels of water of about 0.30% to about 0.60%, of water, the polymers are extrudable into tough products possessing superior slip, biocompatibility, and water absorption and enhanced wet tensiles and tear strengths.

Preferably for forming an improved slip product, an amount of at least about 60% of polyoxyethylene diol can be used in the reaction mixture, more preferably at least by weight about 75% of polyoxyethylene diol, most preferably at least about 80% of the polyoxyethylene diol of the total weight of the reactants is used in the reaction mixture. Also, the improved reaction product of this aspect forms a high slip, biocompatible, water absorptive coating, exhibiting low advancing and receding water contact angles. The receding angles can be less than about 25%, preferably less than about 20%, most preferably less than about 15%. The improved slip reaction product preferably has an amount of water added in the reaction mixture of from about 0.001% to about 0.18%, and a NCO to OH ratio of about 0.85 to about 0.99. The high slip polymer can have a viscosity at about 3% concentration in 60/40 propylene glycol/water from about 50 cps to insolubility, preferably from about 200 cps to insolubility, more preferably from about 300 cps to insolubility.

At water levels by weight of the reaction mixture of about 0.001% to about 0.07% and NCO to OH ratios of about 0.85 to about 0.96, the formed polymers are soluble in water and form spreadable solutions. At water levels by weight of the reaction mixture of about 0.07% to about 0.20%, about 5% to about 3.0% of an alkylene glycol and NCO to OH ratios of about 0.87 to about 0.99 the polymers can be insoluble in water.

Alternatively, about 0.1% to about 15.0% of polyetherpolycarbonate diols, polybutylene oxides, polyoxytetramethylene diols, polydimethylsiloxane polyoxyethylene copolymers, and polyoxypropylene diols having a number average molecular weight of about 250 to about 2400 can be used in the reaction mixture, preferably from about 0.2% to about 10%, and most preferably from about 0.4% to about 8.0%.

Solubility in water depends upon the type and amount of alkylene glycol and the amount of water in the reaction.

The polymers of the fourth aspect can be used to coat metals, hair, glass, elastomers, and plastics for use in medical, electronic, industrial, and cosmetic applications. The polymers can be dissolved in a variety of solvents, including ethanol, 95/5 to 5/95 ethanol/water, tetrahydrofuran/ethanol, ethyl acetate, acetone, methyl pyrrolidone, methyl ethyl ketone, mixtures thereof, and the like at concentrations of about 0.001% to about 10.0%, preferably from about 0.1% to about 5.0%. The type of solvent and concentration chosen to be used with the polymer depends upon the substrate to be coated and desired thickness of the coating. Preferably for metals the concentration of polymer in the solvent is from about 0.01% to about 4.0%. Metals which can be coated include silicon, silicon dioxide, stainless steel, iron, brass, bronze, copper, zinc, chromium, nickel, plated metals, alloys, and the like. The high slip polymers can be used to coat silicon computer chips for use as medical devices, to aid in the manufacture of computer chips, and also to coat plastic molds of computer chips and arrays for use as medical sorting devices. The high slip polymers of this aspect can be used to coat chlorinated and nonchlorinated elastomers including latex rubber, synthetic elastomers including scrap rubber, silicone rubber, butadiene/acrylonitrile/methacrylic acid terpolymers, butadiene/styrene and butadiene/acrylonitrile copolymers and the like. The polymers can be used to coat polyurethane, polymethylmethacrylate and copolymers, polyvinyl chloride, polystyrene, and blends of polystyrene with other polymers including polyphenylene oxide, and hydrophobic elastomers and plastics that have been treated by plasma energy and oxidative gases to increase the hydrophilicity of the surface. The treated polymers include scrap rubber, polyethylene, polypropylene, polyetherpolyamides made by Elf Aquitaine under the tradename of Pebak, and the like.

The high slip polymers can also be used to coat hydrophobic surfaces that have been primed with amphiphilic polyether polyurethanes described in the first, second and third aspects of this disclosure. For example, latex and synthetic rubber gloves and rubber products can be coated with an amphiphilic polymer described in the second aspect of this disclosure and then topcoated with the more hydrophilic high slip polymer described in this aspect. The concentration of polymer in solution is about 0.01% to about 10%, preferably about 0.1% to about 6% and most preferably about 0.15% to about 3.5%.

The coated products can be used in medical, cosmetic, and industrial applications. Products which can be coated include polyethylene stylets, synthetic and natural woven and nonwoven cloths such as polypropylene, and polyethylene cloths, and polyester and polytetrafluoroethylene cloths made under the tradenames of Gortex, Dacron and Teflon for medical and industrial applications, cotton, silk, and sutures, stainless steel needles and guide wires for use in urinary, cardiovascular, and infusion therapy catheters, elastomeric type exam, surgeon, dental, electronic, automotive, and industrial gloves, cosmetic products and medical sorting devices, medical gloves, condoms, and other rubber gloves products. The high slip polymers of the fourth aspect can impart rapid softening, high slip, hypoallergenicity, smoothness, high and rapid water absorptivity, excellent wet strength, high expansion, biocompatability, lubricity and breathability to the coated product.

The high slip polymers comprising about 0.1% to about 15% polydimethylsiloxane polyoxyethylenecopolymers having a number average molecular weight of about 250 to about 3000 can be used as a coating of synthetic and rubber gloves due to their excellent solubility and dispersability in aqueous solutions and solutions with 1% to 70% of ethanol. The polymers impart excellent dry, damp and wet donnability. The polymers can also be applied on-line, that is, during the production of the gloves, and do not require additional curing time such as needed by other hydrophilic polymers. The polymers can also be useful in hair care products such as, for example, hair conditioner, spray, mousse, gel and shampoo, and skin care products such as an antiperspirant, face and hand cream, make-up, sunscreen, medical and body cream and lotion and are suitable for use in latex and oil paints, lubricant, foam, disinfectants, fragrance and drug delivery systems.

For use in coating rubber products such as surgical, medical, clean-room, electronic and industrial gloves and condoms, and to further enhance damp and wet donnability, the hydrophilic polymers of the fourth aspect of the present invention can be mixed at a concentration of polymer solution of about 0.1% to about 6% with about 0.01% to about 20%, based on polymer solids, of hydrophilic polymers such as polyvinylpyrrolidone and polyoxyethyleneoxide, and with polymers described in the first, second and fifth aspects of this invention made with polydimethylsiloxane polyoxyethylene copolymers, based on polymer solids.

It has been discovered that the high slip polymers of the present invention because of their high hydrophilicity and inherent biocompatible nature can be used to transport proteins, pharmaceutically active drugs, cells, blood and vitamins without significantly modifying their structure and effectiveness. The polymers can be used as coatings of blood collection containers, coronary, urinary and biliary stents, and infusion therapy catheters. The hydrophilic polymers of this aspect do not significantly alter the structure and composition of the complex proteins. This property enhances their use in wound dressings, absorbents, sorting devices, coatings of rubber products, catheters, guide wires, cannula, ports, introducers, valves, tubing, and a wide range of medical devices. The high slip polymers allow aqueous solutions of a wide range of molecules to pass through a sorting medical device such as a computer chip because of high slip, biocompatability, high water absorptivity, low to nonadsorption of complex proteins and cells, and smoothness of the coating. The high slip polymers of this aspect comprising about 0.03% to about 0.2% by weight water in the reaction mixture and about 0.88 to about 0.98 NCO to OH ratio can be used to coat metals, plastics, nonwoven and woven cloth and rubber. The polymers comprising 0.05% to about 3.0% alkylene glycols and about 0.01% to about 0.07% water in the reaction mixture, and those comprising 0.01% to about 0.20% water made without an alkylene glycol can be used to form water soluble polymers which are spreadable for use in cosmetics, make-up and as coatings of skin, plastics, metals, and rubber. Solutions of water soluble polymer produce breathable, soft, water-absorptive films. The high slip polymers can be extruded to form tough, water absorbable products that can be used for medical devices, absorbents, cosmetics, shaving razor strips, and industrial applications.

The polymers can be coextruded over other plastics and elastomers possessing lower expansion values. To enhance the adhesion of the hydrophilic polymers to metals and hydrophobic surfaces, isocyanate primers, such as Adcote 533 made by Morton Corporation and Desmophen 670A-80 and BL31-75 made by Bayer Corporation can be coated onto the hydrophobic surface. Polymers comprising mixtures of hydrophobic and hydrophilic segments such as the polymers described in aspect three of this invention, and about 0.01% to about 5% of di and trifunctional acrylates and methacrylate such as trimethylol dimethacrylate, ethylene glycol dimethacrylate, zinc dimethacrylate, and about 0.01 to about 5% of a peroxide, based upon the acrylate, can be mixed into both hydrophilic and hydrophobic polymers and added separately between the layers and mixed only with the hydrophilic layer and heated to form cross4inked interpenetrating networks which hook both hydrophilic and hydrophobic polymers. Because of their unique high hydrophilicity, the polyether polyurethanes of aspect four of this invention impart excellent biocompatibility and superior slip low protein and cell adhesion properties to medical devices enhancing their value in shunts, stents, cardiovascular and infusion therapy catheters, introducers, blood collection units, arterial and venous grafts, mechanical and synthetic heart valves, and the like. The high slip of the polyurethane polymers of this aspect enhances their use for cosmetic and shaving devices and industrial applications.

Also, water soluble molecules including drugs, pharmaceutically active agents, enzymes, and proteins can be absorbed into the high slip polymer coating because of its high absorptivity. Water can be evaporated from the coating at about 15° C. to about 40° C., and then a solution of another molecule can be passed through the device to observe the interaction at a molecular level on screen. A solution of this polymer can be applied to cuts and wounds for aiding in healing the cuts and wounds. Also, the hydrophilicity of the polymers can be further modified with about 0.1% to about 20%, preferably from about 0.3% to about 15%, of a hydrophobic polyoxyalkylene diol selected from the group of polybutylene oxide, polyoxypropylene diol, polyoxytetramethylene diol, polydimethylsiloxane polyoxyalkylene copolymer and polyetherpolycarbonate diols comprising butane and hexane diol, as herein described to impede the leaching of the water soluble molecule from the coating. Alternatively, an amphiphilic polymer such as described in aspects one, two and three of this invention can be coated over the hydrophilic polymer which serves as the reservoir for the drug, cell, protein, chemical, material and extends the elution, thereby increasing the activity of the material.

The hydrated hydrophilic polymers have a helix nature allowing long chain materials such as hydrophilic polymers, enzymes, cells, drugs, and molecules to become intertwined with the helix and form interpenetrating networks with the hydrated hydrophilic polymer helix. The entrapped molecules and materials can exhibit their unique activity for a greater period of time than if the materials which were not captured by the helix hydrated polymer. For example, some of the heparin, TPA, long chain enzymes, materials and DNA type materials incorporated into the polymer elutes out of the hydrated structure within a short period, and the rest can remain captured within the helix for a much longer period, and retain its activity for an extended period.

The coated material can be used to remove a specific virus, bacteria, cell, protein, ingredient from a solution by preabsorbing a receptor for the molecule and cell, an adsorber of the molecule and cell from the solution. The molecule containing the receptor of a particular virus can be adsorbed into the polymer, allowing a blood sample containing the virus to pass through tubing in order to adsorb and denature the virus. The diols in the fourth aspect impart biocompatibility, controlled drug delivery and fragrance leaching, lubricity, low tack and viscosity, controlled water repellency, superior wetting, and flow for use in hair conditioners, drug and fragrance delivery systems, and coatings of rubber and non-woven products.

Polymers of this aspect can be extruded into water permeable and water swellable films and can be mixed with water, propylene glycol and water, and glycerine and water to form unique gels for use in wound care, cleaning fluids, oil-drilling, and delivery of drugs, and can form unique films for cosmetic, medical and industrial products.

The fifth aspect of the present invention relates to creams, pastes, foams, lotions, emulsions, dispersions, solutions, coatings and gels formed from the above-described amphiphilic polyether polyurethanes. In the fifth aspect of the invention, the amphiphilic polyether polyurethanes can be blended with water, oils, humectant, drugs, herbs, vitamins, solvents, waxes, fillers and emulsifiers to thicken liquids, form emulsions and dispersions, and to form spreadable lotions, creams, solutions, amorphous gels and coatings of rubber products for cosmetic, medical and industrial applications. The amphiphilic polyether polyurethanes can be formed of the reaction product of a polyoxyalkylene diol having hydrophilic polyoxyethylene diol having a number average molecular weight of about 4000 to about 20,000, hydrophilic polyoxyethylene diol having a number average molecular weight of about 600 to about 2000, hydrophobic polyoxyalkylene diol having a number average molecular weight of about 200 to about 3000, an organic diisocyanate, and a water equivalent from about 0.005% to about 0.30% in an equivalent mole weight ratio of NCO to OH from about 0.80 to about 0.99.

Preferably the amount of the hydrophilic polyoxyethylene diol having a number average molecular weight of about 4,000 to about 20,000 in the reaction mixture is from about 45% to about 96%, preferably from about 50% to about 92%, and most preferably from about 60% to about 90%. Preferably the amount of the lower molecular weight polyoxyethylene diol having a number average molecular weight of about 600 to about 2,000 is from about 0.1% to about 20%, preferably from about 1% to about 15%, still more preferably from about 2% to about 10%.

The hydrophobic polyoxyalkylene diol can be a polyoxypropylene diol having a number average molecular weight from about 300 to about 1200, and most preferably from about 400 to about 1000. Preferably, the amount of the polyoxypropylene diol is from about 0.2% about 20%, and more preferably from about 0.5% to about 10%.

Alternatively the hydrophobic polyoxyalkylene diol is a polyoxytetramethylene diol and polybutylene oxide having a number average molecular weight from about 200 to about 3000, and most preferably from about 250 to about 2,000. Preferably, the amount of the polybutylene oxide and polyoxytetramethylene diol is from about 0.1% about 20%, and more preferably from about 0.2% to about 10% by weight of the reaction mixture.

Preferably the amount of water in the reaction mixture for polymers of this aspect comprising polybutylene diol and polyoxytetramethylene diol is from about 0.005% to about 0.35%, preferably from about 0.008% to about 0.30%, still more preferably from about 0.01% to about 0.25%, and most preferably from about 0.02% to about 0.20%. Preferably the ratio of NCO to OH is from about 0.80 to about 1.00, more preferably from about 0.85 to about 0.98.

The amount of diisocyanate in the reaction mixture can vary from about 2% to about 70%, preferably from about 3% to about 40%, and more preferably from about 3% to about 25%. The polymers are prepared by reacting the polyoxyalkylene diols with the diisocyanates. Still more preferably, isocyanates are methylene bis(-cyclohexyl-4-isocyanate) and methylene bis(phenyl-4-isocyanate), and most preferably methylene bis(-cyclohexyl-4-isocyanate).

Alternatively, an alkylene glycol is selected from butane diol, hexanediol, 2-methyl-1,3 propanediol, cyclohexane methanol, 2,4, pentne diol, diethylene glycol, dipropylene glycol, and tripropylene glycol can be used in the reaction mixture. The amount of the glycol in the reaction mixture is from about 0.5% to about 10%, preferably from about 1% to about 7%. Alternatively, block copolymers of ethylene oxide and propylene oxide having a number average molecular weight of about 1000 to about 2500 can also be used in the reaction mixture. Preferred block copolymers are those produced by Union Carbide Corporation under the trademark of F127, F68, and L35. The amount of block polymers in the reaction mixture is from about 2% to about 20%.

Alternatively, the hydrophobic polyoxyalkylene diol used in the reaction mixture of the sample is a polyether polycarbonate diol (PCD) having a number average molecular weight from about 600 to about 2400, preferably from about 800 to about 2000. Preferably the diol in the PCD is selected from propylene glycol, butane diol, pentane diol, and hexane diol, more preferably butane diol and hexane diol. Preferably about 0.1% to about 20% of PCD is used in the reaction mixture, more preferably from about 0.2% to about 20.0%, and most preferably from about 0.20% to about 10.0%. Preferably the amount of water by weight in the reaction mixture is from about 0.001% to about 0.3%.

It has been discovered that polymers comprising polyether polycarbonate diols made with butane diol and hexane diol and having a molecular weight of about 800 to about 2000 form emulsions and thicken aqueous media. Polymers comprising polydimethylsiloxane polyoxyethylene copolymers and having a molecular weight of about 500 to about 2500 form solutions, emulsions and dispersions depending upon the molecular weight and concentration of PDMS and type of diol, and amount of urea groups in the reaction formula. Apparently the dimethylsiloxane group in PDMS having a number average molecular weight of about 1500 to 3500 is sufficiently hydrophobic to cause the polymer chain to coil. Polymers made with PDMS having a number average molecular weight of about 500 to about 1500 can form solutions in water.

Polymers comprising polyether polycarbonate diol groups based upon butane diol and hexane diol are soluble in water and emulsify oils in an aqueous media because the polymer is extremely hydrophilic. The butane-carbonate section in the polymer forms the head and the polyoxyethylene section group forms the tail of the polymer chain to function as an emulsifier. For each type of silicone and carbonate comprising polymer, further modification of the effect can be realized by the amount of urea groups and the molecular weights of the hydrophilic diol and the alkylene diol, respectively. All these effects are unexpected for hydrophilic polyurethanes.

It has been discovered that polymers made with about 0.1% to about 15% of PCD preferably from about 0.2% to about 10%, most preferably from about 0.3% to about 7% of the polyether polycarbonate diol having a number average molecular weight of about 900 to about 2000 and about 0.001% to about 0.25% of water in the reaction mixture, preferably about 0.010% to about 0.15%, more preferably from about 0.015% to about 0.07% water have unexpected properties. The polymers thicken aqueous media and form spreadable, low pH, aqueous solutions and also form emulsions in the presence of hydrophobic materials such as oils, vitamins, drugs, and the like. For example, 70 grams of an aqueous solution of about 2% polymer comprising about 5% PCD made with butane diol was mixed with 12 grams of cottonseed oil and 17.5 grams of water and 0.5 gram Germaben to form a creamy emulsion with a flowable viscosity and a pH of 7.0. The cream was readily spread on the hand and formed a tough, water-resistant, breathable, non-greasy film. For example, 70 grams of an aqueous solution of about 2% polymer comprising about 1% PCD made with hexane diol was mixed with 12 grams of cottonseed oil and 17.5 grams of water and 0.5 gram Germaben to form a creamy emulsion with a flowable viscosity of 9200 cps and a pH of 7.0. The cream was readily spread on the hand and formed a tough, water-resistant, breathable, non-greasy film. The polymer formed of 1% PCD at about 2% concentration increased the viscosity of water to 110,000 cps. The polymer can be used to prepare spreadable, breathable face and hand creams, make-up, lotions, and as thickeners for use in paints and polar materials.

Alternatively, the hydrophobic polyoxyalkylene diol in the reaction mixture is a polydimethylsiloxane polyoxyethylenecopolymer (PDMS). The ratio of NCO to OH groups is from about 0.85 to about 0.98.

It has been further discovered that polymers made with about 0.1% to about 15% of PDMS and about 0.01% to about 0.3% water in the reaction mixture form dispersions in water and those made with PDMS having a number average molecular weight of about 500 to about 1500 and 0.01% to about 0.20% form solutions. For example, polymer made with 5% of PDMS having an number average molecular weight of about 800 and 0.03% water dissolved in water and has a viscosity of about 2% concentration of about 6,000 cps and a polymer made with 5% of the same aqueous dispersion PDMS and 0.10% water has a viscosity of about 59,000 cps. For example, polymer comprising about 0.035% water and about 5% polydimethylsiloxane polyoxyethylenecopolymer having a number average molecular weight formed an aqueous disperion of 2440 and has a viscosity of 18 cps in water and 126 cps in 60/40 propylene glycol/water and of polymer comprising about 0.10% water and about 5% of the silicone containing diol formed a dispersion has a viscosity of 165 cps in water and 150 cps in a propylene glycol and water media. Both mixtures were hazy, indicating dispersions were obtained.

For each type of silicone and carbonate comprising polymer, increasing the amount of urea groups in the polymer causes an increase in the viscosity of aqueous solutions. Also the amount and molecular weight of the polyoxyethylene diol and alkylene glycol affect the polymer properties. Alternatively the alkylene glycol can be omitted. The effect of these hydrophobic diols upon the solubility and dispersabilty of hydrophilic polyether polyurethanes is unexpected.

The solutions and dispersions can be used to make hair styling aids, gels, mousse, hair sprays, because of their superior set retention, holding properties, lubricity, ease of combing, and can be used to make a hair conditioner alone and in a shampoo formulation, since the polymer comes out of the dispersion and deposits on the hair. Because of the low viscosity of aqueous solutions and dispersions formed of the polymers, the polymers are especially useful in hair styling aids such as hair sprays and mousse and to coat rubber products such as synthetic and natural rubber gloves. The polymers can be spread on the skin to form a smooth, nongreasy and soft film. The dispersions can be used for coatings, to improve the brushability of paints, and to enhance the lubricity and flow of aqueous media, and for delivery of compounds for cosmetic, medical, and industrial applications.

The polymers can be used for skin care products such as antiperspirants, creams and lotions, medical creams, face and hand creams, make-up, sunscreen creams, sunburn lotions, lipstick, nail polish, paints, lubricants, foams, as coatings of natural and synthetic rubber products, skin care, chemicals, nutrients, disinfectant, fragrance retention and drug delivery systems, coatings of rubber goods, metals, and plastics. The high oxygen transmission rates and softness of these films aid in healing sunburns, cuts and wounds and maintaining a healthy skin.

Because of the water-soluble and dispersion-forming properties of these high slip and water absorptive polymers comprising about 0.1% to about 25% of polydimethylsiloxane copolymers having a number average molecular weight of about 500 to about 3,000 and about 0.01% to about 0.20% water these polymers can be mixed in water without any solvent and coated onto metals, plastics, and rubber goods. For example an about 3% solvent-free aqueous dispersion of the polymer described in Example 44 and 1.5% molecular sieve filler was used to coat rubber gloves and improve their dry and wet donnability. The combination of filler and the polymer of this aspect absorbs moisture at low and high humidities, enhances the rate of donning, and feels lubricious. Preferably, the amount of polymer in the coating system is from 0.1% to about 10%, preferably from about 0.2% to about 5%, and the amount of filler is from about 0.5% to about 50%, preferably from about 1% to about 30%. Spreading a 0.1% to about 10% solution, lotion and cream of the polymer formed with polydimethysiloxane polyoxyethylene copolymers and 0.01% of about 0.20% of water in the reaction mixture on the hands and skin further enhances the donnability of rubber gloves and other rubber products.

The polymers of the fifth aspect can be used to coat rubber products and provide improved lubricity and superior dry, damp and wet donnability of rubber gloves. For example, a one percent aqueous solution was prepared of a polymer of the fifth aspect made with about 5% of PDMS having a molecular weight of about 800 with about 0.15% of water and having an NCO/OH ratio of about 0.92 amd 0.50% Armeen D and 0.10% Darvan L. Rubber gloves were dipped into the solution for five seconds and then placed in the oven after allowing the solvent to evaporate. The gloves have improved dry and damp donnability. Similarly, a hand mold was dipped into a coagulant solution, dried, then dipped into a rubber latex, then dried, allowed to leach for one hour in water, dried, then dipped into the polymer solution. The gloves were baked at an elevated temperature.

For coatings of synthetic and natural rubber products, including exam, surgical, industrial, medical and clean room gloves, the polymers of the fifth aspect are produced from about 0.1% to about 30% of polydimethylsiloxane polyoxyethylenecopolymer, preferably about 0.5% to about 20%, about 0.005% to about 0.4% of water in the reaction mixture, about 50% to about 85% of polyoxyethylene diol having a number average molecular weight of about 3,000 to about 20,000, about 0.1% to about 25% of polyoxyethylene diol having a number average molecular weight of about 200 to about 2,000, preferably about 0.5% to about 20%, and preferably having a number average molecular weight of about 600 to about 2,000, and an NCO/OH value of about 0.88 to about 0.98. The polydimethylsiloxane polyoxyethylenecopolymer has a number average molecular weight of about 500 to about 3,000. For solutions of the polymer in water and in ethanol and water solutions with less than about 50% ethanol, the preferred molecular weight of the PDMS is about 500 to about 1,500.

It has been discovered that polymers made with about 0.1% to about 10% of a hydrophobic diol such as about 0.1% to about 2% of polyether polycarbonate diols, about 0.5% to about 5% of polyoxypropylene diol, polyoxytetramethylene diol, polybutylene oxide, and PDMS having number average molecular weights of about 200 to about 1,500 form solutions in water and in propylene glycol/water for use in cosmetics, and can be used to control the release of different additives such as drugs and fragrances. The compositions comprising the soluble polymers and fragrances can be used in industrial, medical and cosmetic applications such as antiperspirants, skin care, sunscreens and hair care applications. It has been further discovered that an increase of about 0.02% to about 0.05% in the amount of water in the reaction mixture can raise substantially the viscosity of aqueous solutions of the polymer.

Because of the water-thickening properties of hydrophilic polymers comprising hydrophobic diols, the polymers are especially useful in cosmetics, paints, and oil well digging compositions. Because of unique high slip and lubricious properties, the polymers can be used as anti-fogging coatings and as coatings of materials exposed to water, such as umbrellas.

The polymers of this aspect have viscosities at about 3% concentration in a 60/40 propylene glycol/water solution of about 1 cps to insolubility. For some medical, industrial and cosmetic applications, the viscosity is preferably from about 2 cps to about 100,000 cps, more preferably from about 4 cps to about 50,000 cps and most preferably from about 5 cps to about 40,000 cps. The polymer can be insoluble at about 3% concentration in 60/40 propylene glycol/water. The concentration of the polymer capable of forming a solution varies depending on the weight average molecular weight of the polymer and the viscosity of the polymer in aqueous media depends upon polymer variables such as the amount of urea groups and amount and type of diol used in forming the polymer.

The polymers comprising silicone-containing diols impart superior wetting, donnability, foamability, emolliency, lubricity, flow and water repellency properties, and polymers comprising polyetherpolycarbonate diol, preferably PCD comprising hexane diol, impart spreadability, emulsifying properties, donnability, emolliency, clarity, flow, and water-repellency.

The amphiphilic polymers of this aspect formed with the controlled amounts of hydrophilic and hydrophobic polyoxyalkylene diols and very low controlled amounts of water provide coatings, lotions, creams, gels, foams, dispersions, emulsions, and solutions that spread readily over many types of surfaces, including skin, metals, glass, plastics, and elastomers to form soft, hypoallergenic, biocompatible, breathable, non-greasy, protective, and water-resistant films. Because the films have this improved combination of properties, -soft, breathable, water-resistant, infection barrier, and protective, the polymers are useful for cosmetic, industrial and medical applications, such as coatings of catheters, guidewires, and blood collection units.

The polymers can be granulated and pulverized to a powder. A solution of the polymer in water is made by mixing the polymer in water at room temperature and then warming the solution, if needed at about 40° C. to about 80° C. Finer particle size and higher temperatures in closed agitated vessels shorten the time for solution. The concentration of the polymer in the solution will be from about 0.1% to about 10%, preferably from about 0.3% to about 8%, more preferably from about 0.5% to about 6%. To the solution can be added oils, waxes, fragrance, emulsifiers, humectant such as propylene glycol and glycerine, desiccants, high molecular weight alcohols, small amounts of ethanol and isopropanol, alpha-hydroxy acids, preservatives, base, perfume, antibactericides, vitamins, herbs, antifungicides, pain-killers and drugs. The mixture is heated at about 40° C. to about 80° C. for about one minute to several hours to dissolve the ingredients. Ingredients can be added at about 25° C. to about 40° C. to prevent degradation of the additive. An amount of a base selected from, for example, ammonium hydroxide, sodium hydroxide, triethanolamine, aminomethylpropanol, potassium hydroxide, and the like may be added to adjust the pH to the desired value, and to thicken the mixture.

Solutions, lotions, emulsions, foams, creams, gels of the polymer of this aspect have a concentration of about 0.01% to about 15% of the polymer, preferably from about 0.1% to about 10% of the polymer. For use in creams, lotions, barrier solutions, and antiperspirants, hair shampoos and conditioners, gels, mousse, bath products, drug and fragrance delivery systems, deodorants, medical and therapeutic mixtures, to aid in donnability of elastomeric gloves, and as thickeners, the amount of polymer is from about 0.1% to about 6%. For amorphous gels, the amount of polymer is from about 1% to about 10%. A stiff gel can be formed of an amount of polymer from about 5% to about 25%. The stiff gels can be used in cosmetic, medical, and industrial applications.

Waxes which can be used with the polymer of this aspect are selected from beeswax, liquid and solid paraffin, polawax, candelilla wax, multi wax, ceresine, microcrystalline wax, and emulsifiers are selected from cetaaryl alcohol, polysorbate 60, PEG-1 50 stearate and steareth 20 which are produced by Rita Corporation under the tradename of Ritachol 1000, polyoxyethylene (50) lanolin, perhydrosqualene, glycol monostearate, sorbitan monostearate, polyoxyethylene (20), sorbitan monostearate, oleyl alcohol, polyoxyethylene (50), sorbitol polyoxyethylene (2) stearyl ether, PEG 400 dilaurate, POE 4 nonylphenolether, isopropyl palmitate, PEG 15, isopropyl myristate, glyceryl monostearate, triethanol amine stearate, stearamide MEA-stearate, polyglycerol oleate, sodium L glutamate-water, sodium lauryl sulfate, ceteareth 20 petrolatum, stearic acid- triple pressed, cetyl stearoyl lactylate, PEG 200 monolaurate, monoglyceride sulfosuccinate, isopropyl palmitate, PEG 10 soya sterol, and Amerlate, made by American Cholesterol Products, an isopropyl ester of a mixture of normal, branched chain and hydroxy acids of lanolin. Other additives are dimethicone, silicone dimethicone, lanolin, stearic acid, boric acid, lanolin alcohol, disodium ethylene diamine tetraacetate dihydrate, butylated hydroxytoluene, cetyl alcohol and triethanolamine.

Oils are selected from paraffin oil, corn oil, sesame oil, sweet almond oil, hydrogenated vegetable oil, purcellin oil, apricot oil, olive oil, mineral oil, lanolin oil, and the like. Inert powders such as, talc, starch and clays may be dispersed in oils and waxes along with bioactive materials. Other fillers are molecular sieves including Zeolites, Purmol and ZeoChem for moisture absorption, titanium dioxide and zinc oxide.

Other emulsifiers which can be used with the polymer of the present invention are polyglycerol oleate, sodium laurmmoalipropionate, polyglycerol oleates, retinyl palmitate, PEG-100 stearate, caprylic/capric triglyceride, polysorbate 80, octyl methoxycinnamate, sesquistearate, cetyl esters, sorbitan oleates and monoglyceride sorbitol sesquioleate, isomanmide oleate, ethoxylated, propoxylated decanol and ethoxylated propoxylated hexadecanol, and ethoxylated propoxylated hexadecanol esterified with maleic anhydride.

Liposomes can be mixed with the solutions of the polymers and comprise a mixture of a ternary lipid blend of lecithin, dicetyl phosphate and a sterol. Humectants are sodium pyroglutamate, molecular sieves including Zeolites, glycerol, and propylene glycol.

Other ingredients which can be used in the skin and hair products are quaternium 33, ethyl hexane diol, Methocel K 15M premium, preservatives Germaben II (a blend of propylene glycol, diazolidinyl urea, methylparaben, and propylparaben), methyl and propyl paraben, methyl glucose, trisodium ethylenediamine triacetic acid, Carbomer 940, collagen, benzophenone-3, Carbowax 2500, Amerchol L-101, copolymers of N-vinyl pyrrolidone, and of vinyl acetate.

Botanical herbs and vitamins that are advantageous for creams and lotions are sage, lemon, mimosa, willow, comfrey, Tocopherol acetate and linoleate, Vitamin E, Vitamin B, Vitamin C, capsucan, menthol, and panthenol.

Stabilizers that can be used in the reaction mixture are vegetable sterols combined with polyhydroxy oleates and ricinoleate. Creams can be made with the magnesium salt of the half ester of succinic acid and propoxylated fatty alcohols. Calcium, zinc, aluminum, and magnesium lanolate and lanolin alcohol are also useful in making creams.

It will be appreciated that the typical ingredients of cream, lotion, and solution formulations that are known in the art can be used with the amphiphilic polyether polyurethane of this aspect of the invention.

Typical formulations are given in the examples. The creams and lotions can be used to aid in male and female shaving comfort, lubricity, smoothness, pre- and post-shaving preparations and decreasing wrinkles, in flattening scars, and healing scars and reducing their hardness, and can be rubbed on the chest to aid in respiratory illnesses, on fingers and feet to keep them warm during cold weather, under the nose to aid in breathing during respiratory illnesses, on the head to promote a healthy scalp, and on skin to retain sunscreen lotions and creams for longer periods. The polymers comprising about 0.2% to about 10% hydrophobic diols such as polyoxypropylene diols, polyetherpolycarbonate diol using hexane and butane diols, and polydimethysiloxane polyoxyethylene diol having a number average molecular weight of about 250 to about 1500 of this aspect and the fourth aspect can be dissolved in propylene glycol/water mixtures having about 5% to about 50% propylene glycol to retain fragrance in air fresheners, antiperspirants, shaving preparations, hair care and skin care applications.

The films can lengthen the useful period for UV stabilizers, antioxidants, drugs, herbs, vitamins, and reduce the loss through solution in water of drugs, vitamins, and fragrance. The creams and lotions can be used to aid in damp donnability of rubber gloves by absorbing moisture, and improving slip, over small cuts and wounds in combination with first aid creams to provide an hypoallergenic, biocompatible, infection barrier, breathable, water-resistant, oxygen-permeable film which promotes the healing of cuts and wounds with or without gauze.

Gels using the amphiphilic polyether polyurethanes of the fifth aspect can be used in deodorant sticks and antiperspirants, and to provide a healing environment for burns and wounds. The gels can be spread onto a variety of surfaces including skin, metals, glass, and plastic.

The films can aid in acceleration of healing of wounds and cuts in combination with gels and bandages by preventing infection while they allow for the transmission of moisture and oxygen which promote healing, and slow absorption of drugs into the skin. The rate can be accelerated by iontophoresis methods. The films can protect fragile skin from aggressive adhesives. The films can serve to provide a soft low wrinkle feeling to skin. The water-resistant films can be used as sunscreen and retain UV additives for longer periods, and resist rinsing with water. The films can be used to prevent and heal urinary and baby rash, since the films protect the skin and form water-resistant, hypoallergenic, breathable, non-greasy, bacteria and infection barrier. Water-soluble vitamins, hydrophobic materials, growth factors, endothilializers, wound and skin healing molecules drugs, fragrances, perfumes, antibactericides, disinfectants can be added to the solutions, lotions, and creams for use in industrial, medical and skin care creams and lotions.

For certain applications such as to encapsulate fragrances and drugs, high viscosity hydrophilic polymers are preferred, such as those that are insoluble in propylene glycol/water, and for other applications water soluble polymers may be preferred. The degree of water solubility can be adjusted by the amount and type of hydrophobic diol, ratio of isocyanate to hydroxyl groups, the amount of urea groups, and the molecular weight used in the reaction mixture for forming the polymer. Also, the degree of hydrophobicity can regulate the rate of leaching of the water-soluble compound.

A catheter can be formed from polymers of the second aspects of the present invention which can be coextruded with more hydrophilic polymers described in the third, fourth and fifth aspects of this disclosure, depending upon the degree and rate of softening required for the catheter. The coextruded film can range in thickness from about 0.0001 mil to about 0.050 mil. To obtain a tough highly biocompatible catheter with improved slip properties, the polymers of the fourth and fifth aspects can be coextruded over the polymers of the first and second aspects. The high dry and wet strength polymers of the first and second aspects form the core, while the those of the fourth and fifth apsects provide high slip, low cell adhesion and biocompatibility. The polymers can be coextruded over elastomers to form expandable products.

The polymers of the first and second second aspect can be coated over those of the fourth and fifth aspects to decrease the elution rates in aqueous media of drugs, chemicals, enzymes, cells, proteins and the like contained in the more hydrophilic polymers. For example, a protein absorbed in the hydrophilic polymer eluted within two weeks and eluted after four weeks when coated with a hydrophobic coating.

Salts of other metals can be used to catalyze diisocyanates and diols of the above-described polymers, the metals can include magnesium, calcium, potassium, lead, zirconium, zinc and bismuth, including but not limited to bismuth acetate, bismuth octoate, bismuth nonododecanate, potassium octoate, potassium acetate, zinc octoate, zinc acetate and the like. Perferably potassium octoate, zinc octoate, bismuth octoate and bismuth nonadodecante are used to polymerize diisocyanate and diols.

Preferably the catalysts used in the reactions of the above-described polymers are stannous octoate and dibutyl tin dilaurate, manufactured by Air Products and Chemicals as $T_9$ and $T_{12}$ potassium octoate, potassium acetate, zinc octoate, bismuth octoate and bismuth neodecanate. Alternatively, in forming a polyurethane with methylene bis(phenyl-4-isocyanate) MDI the catalyst can be omitted.

It has been discovered that use of about 0.8 cc to about 6 cc of certain catalysts, selected from dibutyl tin dilaurate, stannous octoate, bismuth octoate and bismuth neodecanate, per pound of reactants can produce high molecular weight polymers comprising low levels of urea groups at a concentration of water in the reaction mixture of about 0.001% to about 0.15% and that the molecular weight of the polymer can be controlled by selecting the NCO/OH ratio in addition to the amount of water in the reaction mixture.

Polymers of the above-described aspects, preferably, polymers of aspect two and aspect four can be used to coat metals, plastics, synthetic and natural, woven and nonwoven cloth. Suitable cloths include cloths formed of polyester, acrylics, polyfluoroethylene, polyethylene, polypropylene, silk, wool, cotton, Teflon® and Dacron®. Teflon® and Dacron® are trademarks of Dupont. The coated cloths can be used to suture implants, mechanical heart valves, animal heart valves, and synthetic heart valves to tissue and muscle. The coated cloth can be used as an implant. The coated cloth can be formed into tubing for use as vascular grafts such as synthetic veins and arteries for the arterial and peripheral system.

The coated cloth can be used as a carrier to absorb a drug, cell, enzyme, and short and long chain materials. For example, suitable agents used in the coated cloth include pharmacologically active agent, anticoagulant, antithrobomgenic agent, anticancer drug, cellular growth material, anti-infective agent, and antibiotic. The coated cloth comprising the absorbed material can be used as a medical device and also implanted into the human and animal bodies as a vascular graft. Suitable antithrombogenic agents are prostaglandin, urokinase, streptokinase, tissue plasminogen activator (tPA), coumadin, dicumerol, protamine sulfate, hirudin and heparinoids. Preferred antithrobomgenic agents are sulfonated heparinoids, such as dextran sulfonate, most preferably heparin, albumin or a salt thereof Suitable anticoagulant agents which are antibodies (for example antibodies directed against platelet receptor Gpib or Gpib, against platelet receptor GPib/IIIa, or against von Willebrand Factor (vWF)) and also such agents with vasoactive properties (such as Prostacyclin and Nitric Oxide). Suitable pharmaceutically active agents include growth factor regulators in particular antibodies. Suitable antibodies include antibodies directed against Platelet-derived Growth Factor (PDGF), Fibroblastic Growth Factor (FGF), Transforming Growth Factor beta (TGF), Insulin-like Growth factor (IGF), Interleukins (IL1-8), Endothelin, Trombin, or Endothelial adhesion molecules, for example is ICAM-1. Also suitable are angiotensin converting enzyme (ACE) inhibitors (for example Captopril), and endothelial cell growth factor (ECGF). Also, anti-sense oligonucleotides or antibodies to particular mRNAs can be used, for example anti-sense oligonucleotides to a -myc, PCNA and the like or antibodies to the mRNA molecules encoding for growth factors.

For example, the woven or nonwoven cloth can be formed by dipping the woven or nonwoven cloth into a solution of the polymer in a solvent. The solvent evaporates for about one minute to about sixty minutes at room temperature to form a coated cloth. The coated cloth is heated at an elevated temperature for about 1 minute to about sixty minutes to substantially remove the solvent. The coated cloth is allowed to cool to room temperature. The coated cloth is dipped into a solution comprising the above-described agents and materials to be incorporated into the coating. The coated cloth is allowed to dwell in the solution from about 0.01 second to about one week, preferably about half second to about thirty hours. The coated cloth is removed and the solvent is allowed to evaporate at room temperature and then placed in an oven at about 20° C. to about 120° C. depending upon the nature of the agent or material incorporated into the coating. For example, coated cloth comprising tPA is heated at about 15° C. to about 40° C., but not above 40° C.

Preferably, a coated cloth comprising tPA can be used as a vascular graft and to suture an implant and heart valve to tissue and muscle. The polymers of the above-described aspects can also be used to coat implants and medical devices such as stents, valves, oxygenators, needles, tubing, gaskets, infusion therapy, urinary and cardiovascular catheters and guidewires, and other devices. The catheters and guidewires can be coated with the polymers of this aspect to facilitate the insertion and withdrawal of the devices. The agent or material to be incorporated into the coating depends upon the specific purpose of the medical device. For example, a stainless steel stent to be inserted into an artery can be coated with the high slip and high absorptive polymers of aspect four and five described above, preferably polymers of aspect four and then the coated stent can be dipped into a solution of tPA as an anticoagulent. After drying the coated stent at low temperatures, the stent can be sterilized and implanted into a human; the coated stent reduces the body's tendency to form clots due to a foreign object.

Coated materials will release additives in the substrate such as drugs, pharmaceutically active agents, fragrances, and hydrophilic polymers such as PVP and Polyox at a lower rate in an aqueous media due to the coating. This property enhances their use in products including but not limited to medical devices, cosmetics and shaving applications. It has been found that the materials can be absorbed in a short period of time, for example, from about 0.01 minute to about 48 hours, and can remain captured within the hydrated hydrophilic and amphiphilic polymer helix for a much longer period, for example from about one minute to about four months, and can retain its activity for an extended period, for as long as one year. The materials can also be incorporated into the substrate prior to as well as after coating with the amphiphilic polymers of above-described aspects one, two and three, and the more hydrophilic polymers of aspects four and five.

Polymers of the above-described aspects can be coated over one another to form a two layer or multi-layer system having more than two layers. Preferably, polymers of the above-described second aspect can be coated over a layer of the fourth aspect, and polymers of the fourth aspect can be coated over polymers of the second aspect to provide a two layer system. Polymers of the second and fourth aspect or a hydrophilic polymer can be coated over the two layer systems to provide a triple-layer system. The first layer of the amphiphilic polymer on the substrate has a different abosptivity than the second layer of amphiphilic polymer coated over the first layer. Preferably, the first layer is a polymer of aspect four having a water absorptivity of at least about 70%, more preferably at least about 80% and the second layer is an amphiphilic polymer of aspect two having a water absorptivity of less than 35%. Alternatively, for certain applications polymers of the first and third aspect can be used with and in place of the polymers in the second aspect in the two layer and three layer system, and those of the fifth aspect can be used with and in place of the polymers of the fourth aspect.

The elution rate of the additives can be controlled by using amphiphilic and hydrophilic polymers of different water absorptivities. Polymers with low absorptivity absorb less material and also exhibit lower elution rates and polymers with higher absorptivity absorb more material and have higher elution rates. By using combinations of both types, large amounts of an additive can be obtained and the elution rate can be controlled by using the polymer with the requisite water absorptivity selected from aspects one, two and three. The combination can be coated with a hydrophilic polymer to obtain an improved biocompatible surface.

For vascular grafts, implants, mechanical and synthetic heart valves, the preferred polymers of aspect four are those made with about 65% to about 96% of polyoxyethylene diol having a number average molecular weight of about 3,000 to about 20,000, 0.01% to about 0.30% water in the reaction mixture, preferably from about 0.02% to about 0.25% water, most preferably about 0.03% to about 0.20% and to an NCO/OH value of about 0.88 to about 0.99.

The polymers of the above-described aspects one, two and three having an amount water in the reaction mixture of about 0.01% to about 0.40% by weight of the reaction mixture can be blended and coextruded with hydrophobic polymers and elastomers to form a blended polymer, the blended polymer can be used in expandable sealants, moldings, toys, gaskets, medical devices and industrial products. The amphiphilic polymer of aspects one, two and three can be generally represented as the reaction product of a hydrophilic diol having a number average molecular weight of about 400 to about 10,000 in an amount of about 1% to 50%, at least one hydrophobic diol selected from the group consisting of polyoxytetramethylene diol having a number average molecular weight of from about 250 to about 3,000, polyoxypropylene diol having a number average molecular weight of from about 400 to about 2,500, a polyether polycarbonate diol having a number average molecular weight of about 1,000 to about 2,000, and a polydimethylsiloxane polyoxyalkylene copolymer having a number average molecular weight of about 500 to about 3,000, wherein the polyoxyalkylene is selected from the group consisting of polyoxyethylene and polyoxypropylene, the amount by weight of the hydrophobic diol in the reaction mixture being from about 20% to about 50%. Preferably, the hydrophobic diol for aspect 3 is from about 5 to about 15%.

The blended polymer can include an alkylene glycol selected from the group consisting of ethylene glycol, propylene glycol, 2-ethyl-1,3-hexanediol, tripropylene glycol, 1,6-hexane diol, 1,4-butene diol, triethylene glycol, 2,-4-pentane diol, 2, ethyl-1,3 hexanediol, 2-methyl-1,3-propanediol, 2,-methyl-1,3- pentanediol, cyclohexanediol, diethylene glycol, cyclohexanedimethanol, dipropylene glycol, and mixtures thereof, an organic diisocyanate, and water in an amount by weight of about 0.01% to about 0.4% of the reaction mixture, the ratio of NCO to OH of the diols, the alkylene glycol and the water being from about 0.80 to about 1.2, For example, the hydrophobic polymers can include polystyrene, polyvinylchloride, polyethylene, polypropylene, polyurethanes, ethylene-1-octene, ethylene-1-butene, ethylene-alpha olefins, and the saturated and unsaturated elastomers can include ethylene/propylene copolymers, butadiene/styrene copolymers and terpolymers, natural and butyl rubber, polyisoprene, and the like. Compatibilizers such as maleated polypropylene, maleated ethylene-propylene copolymers, and ethylene/acrylate copolymers and hydrophobic polyurethanes comprising small amounts of hydrophilic polymer can be used in the blended polymer. For example, a polymer of this aspect formed from about 15% of polyoxytetramethylene and about 15% of polyoxypropylene diols and water in an amount of about 0.15% of the reaction mixture can be coextruded over and blended with hydrophobic elastomers. The blended polymer has improved expansion properties.

Preferably for blends of the polymer with hydrophobic elastomers and polymers and additives in antiperspirants, shaving preps, hair care and skin care mixtures, the alkylene glycol can be selected from higher molecular weight alkylene glycols such as dipropylene glycol, diethylene glycol, ethyl hexyldiol, 1,6-hexane diol, 1,4-butane diol, tripropylene glycol, 2-ethyl-1,3-hexanediol, tripropylene glycol, triethylene glycol, 2,-4-pentane diol, 2-methyl-1,3-propanediol, 2,-methyl-1,3- pentanediol, cyclohexanediol, and cyclohexanedimethanol, and preferably the hydrophobic polyoxyalkylene diols are selected from polyoxypropylene, polyetherpolycarbonate, and polyoxytetramethylene diols, butylene oxide and polydimethylsiloxane polyoxyethylenecopolymers having a number average molecular weight of about 200 to about 3,000, preferably from about 200 to about 2,500.

Preferably for the use of the polymers in blends of hydrophobic polymers and elastomers, and as coextrusions over elastomers and plastics, the amount by weight of water in the reaction mixture is in the range of from about 0.03% to about 0.30%, more preferably from about 0.08% to about 0.25%. Preferably polymers of aspects one and three having water absorption of about 30% to about 55% can be used in the blends with hydrophobic polymers and elastomers.

The polymers of aspects four and five especially those polymers which are made with about 0.01% to about 0.20% water in the reaction mixture in an NCO/OH ratio of about 0.80 to about 0.98 and using about 0.10% to about 10% of a hydrophobic diol selected from polyoxypropylene, polyetherpolycarbonate, and polyoxytetramethylene diols, butylene oxide and polydimethylsiloxane polyoxyethylenecopolymers having a number average molecular weight of about 200 to about 3,000, preferably from about 200 to about 2,500 are water soluble can be used to control the release from the skin of fragrance and additives in antiperspirants, shaving preps, hair care and skin care mixtures. Alternatively, the alkylene glycol can be omitted from the reaction mixture. Preferably, the catalyst is selected from from dibutyl tin diluarate, stannous octoate, bismuth neo-decanate and bismuth octoate.

It has been found that the addition to polymers formed from aspects four and five of about 0.1% to about 60% of desiccant fillers such as ZeoChem, Zeolites, molecular sieves, glycerine, barytes, and calcium sulfate in the primer and topcoats of coatings of rubber products reduce tack and increases water absorptivity at low humidity levels. It has also been found that the use of about 0.5% to about 50% of filler, based upon polymer solids, unexpectedly improves the excellent dry, damp and wet donnability of rubber latex gloves. Preferred fillers added to the polymer are cornstarch, zeolites, barytes, and high slip hydrophilic polymers such as polyvinylpyrrolidone (PVP) and polyoxyethylene oxide (Polyox). Preferably about 0.5% to about 40% of filler is added, preferably Zeolite Type 5A, PVP, and Polyox. Silicones, fatty acid amines, polyoxyalkylene diamines and diglycoldiamines can be added as anti-blocking agents and to improve donnability in combination with the polymer and as a postdip. These materials can include polyether diamines based on propylene oxide and ethylene oxide such as triethylene glycol diamine made by Huntsman Corporation under the tradenames of EDR-148 and Jeffamine ED-600, ED-900, D-230, D400, and ED-2001, and ethanolamines such as monoethanolamine, diethanolamine, triethanolamine, and fatty acid amines as hexadecyldimethylamine, octadecyl-dimethylamine and dodecyl-dimethylamine and surfactants such as dimethylpolysiloxanes made by GE Silicones under the tradenames of SM2140 and 2153, and other surfactants such as ammonium salts of allyl phosphate made by Vanderbilt company under the tradename of Darvan L.

Elastomers can include butadiene/styrene copolymers, hydrogenated and nonhydrogenated styrene/butadiene/styrene, butadiene/acrylonitrile/carboxylic acid nitrile and carboxylic acid containing elastomers, isoprene/styrene copolymers and terpolymers, silicone rubbers, butadiene/styrene/acrylonitrile, butyl and latex rubbers, polyisoprene, polybutadiene, ethylene/propylene copolymers, ethylene and propylene-alpha-olefins polymers, polychlorobutadiene, and chlorinated elastomers. Preferably, solutions used for coating rubber products contain about 0.10% to about 10% of polymer comprising about 1% to about 15% of polydimethylsiloxone polyoxyethylene copolymer (PDMS). The coating mixture has the advantage of simplifying the coating system since the coating can be applied on-line at any stage of the dipping process without curing or cross-linking the polymers and without leaving any residual odor on the hands due to some lubricants. Small amounts of commercial anti-oxidants can also be added to prevent oxidation during the curing of the rubber. The coating mixture can be dissolved in water and ethanol and water mixtures and applied during formation of a glove by dipping and spraying methods. Alternatively, polymers of this aspect of the present invention comprising polydimethylsiloxane polyoxyethylenecopolymers having a number average molecular weight of about 500 to about 3000 can be used in aqueous dispersions and solutions or blended with other hydrophilic polymers and the solution and dispersion can be used to coat rubber products. The polymers can also be used to coat suture needles, sutures, needles, scalpels and metals.

EXAMPLES

The following examples will serve to further typify the nature of this invention but should not be construed as a limitation of the scope thereof.

PREPARATION OF AMPHIPHILIC POLYURETHANES

Example 1

To 307 grams of polyoxyethylene diol having a number average molecular weight of 1450 was added 307 grams of polyoxyethylene diol having an average molecular weight of 4500, 179 grams of polyoxytetramethylene diol having an average molecular weight of 2000, 146 grams of polyoxytetramethylene diol having an average molecular weight of 1000, 45 grams of polyoxypropylene diol having an average molecular weight of 2025, 61 grams of polyoxypropylene diol having an average molecular weight of 1025, and 500 grams of ethylene glycol. The mixture was analyzed for water and water was added to bring the total to 7.3 grams. Then 663 grams of methylene bis(cyclohexyl-4-isocyanate) were added. The ratio of NCO to OH groups was 0.95. The mixture was heated to 50° C. and 2.7 cc of stannous octoate was added. The mixture was allowed to exotherm and was then heated in oven for one hour at 100° C.

The polymer was granulated and extruded in a lab extruder. The extruded polymer was granulated, and had a water content of 40% and an expansion of 21% after 24 hours in water. The extruded and thermopressed polymer had dry and wet Shore A hardness values of 85 and 75, dry and wet tensile strengths of 4330 psi and 2530 psi, dry and wet elongations of 520% and 370%, and dry and wet tear strengths of 280 and 240 pounds per inch. The polymer was extruded into a tough expandable catheter with superior dry and wet strength for urinary and biliary stents, catheters, accessories and components for cardiovascular, infusion therapy, and dialysis, and for medical devices. The polymer can be coated and coextruded over plastics and metals, and can serve as a primer for hydrophobic materials.

Example 2

To 307 grams of polyoxyethylene diol having a number average molecular weight of 1450 was added 307 grams of polyoxyethylene diol having an average molecular weight of 4500, 179 grams of polyoxytetramethylene diol having an average molecular weight of 2000, 146 grams of polyoxytetramethylene diol having an average molecular weight of 1000, 45 grams of polyoxypropylene diol with the trademark of Acclaim 2200, having an average molecular weight of 2000, 61 grams of polyoxypropylene diol having an average molecular weight of 1025, and 100 grams of ethylene glycol. The mixture was analyzed for water and water was added to bring the total to 7.3 grams. Then 663 grams of methylene bis(cyclohexyl-4-isocyanate) were added. The ratio of NCO to OH groups was 0.95. The mixture was heated to 54° C. and 2.7 cc of stannous octoate was added. The mixture was allowed to exotherm and then was heated in oven for one hour at 100° C.

The polymer was cut into strips, granulated and extruded in laboratory Killian extruder. The extruded polymer was granulated. The polymer had a water content of 40% and an expansion of 21% after 24 hours in water. The ground extruded polymer was pressed into plaques for hardness and stress-strain testing. The Shore A hardness of dry polymer was 77 and that of wet polymer was 75. The dry strength properties were a tensile strength of 4180 and an elongation of 450%, and a tear strength of 320 pounds per inch, and wet strength properties of 1790 pounds per square inch, an elongation of 320%, and a tear strength of 200 pounds per inch. The polymer was extruded into a tough and flexible expandable catheter with superior dry and wet strength for use in urinary and biliary stents, cardiovascular catheters infusion therapy, dialysis catheters, and in accessories and components used in medical devices. The polymers can be used to coat and coextrude metals and plastics, and to prime hydrophobic materials.

Example 3

To 91 grams of polyoxyethylene diol having a number average molecular weight of 1450 was added 414 grams of polypropylene diol with the tradename of Acclaim 2200 having an average molecular weight of 2000, and 53 grams of ethylene glycol. The mixture was analyzed for water and water was added to bring the total to 3.85 grams. Then, 346 grams of methylene bis(cyclohexyl-4-isocyanate) were added. The ratio of NCO to OH groups was 0.98. The mixture was heated to 45° C. and 2.7 cc of stannous octoate was added. The mixture was allowed to exotherm and then was heated in oven for one hour at 100° C.

The polymer was cut into strips, granulated and extruded in laboratory Kifflan extruder The extruded polymer was granulated. The polymer had a water content of 4.4% and an expansion of 1.3% after 24 hours in water. The granulated extruded polymer was pressed into plaques for hardness and stress-strain testing. The Shore A hardness of dry polymer was 89 and that of wet polymer was 77. The dry strength properties were a tensile strength of 3250 and an elongation of 400%, and a tear strength of 430 pounds per inch, and wet strength properties of 2060 pounds per square inch, an elongation of 430%, and a tear strength of 320 pounds per inch. The polymer can be used for accessories, components and catheters for infusion therapy, dialysis, and cardiovascular catheters, in shaving systems, and to coat and coextrude metals and plastics. The polymer can be molded for medical devices.

Example 4

To 611 grams of polyoxyethylene diol having a number average molecular weight of 8000 was added 54 grams of polyoxyethylene diol having an average molecular weight of 1450, 104 grams of polyoxypropylene diol having an average molecular weight of 1025, 77 grams of polyoxypropylene diol under the trademark of Acclaim 2200 having an average molecular weight of 2000, and 218 grams of diethylene glycol. The mixture was analyzed for water and water was added to bring the total to 10.3 grams. Then, 746 grams of methylene bis(cyclohexyl-4-isocyanate) were added. The ratio of NCO to OH groups was 0.98. The mixture was heated to 50° C. and 2.7 cc of stannous octoate was added. The mixture was allowed to exotherm and then was heated in oven for one hour at 100° C.

The polymer was cut into strips, granulated and extruded in laboratory Killian extruder. The extruded polymer was granulated. The polymer had a water content of 50% and an expansion of 24% after 24 hours in water. The granulated extruded polymer was pressed into plaques for hardness and stress-strain testing. The Shore A hardness of dry polymer was 98 and that of the wet polymer was 80. The polymer had dry strength properties of a tensile strength of 3840 and an elongation of 140%, and a tear strength of 700 pounds per inch, and wet strength properties of 1260 pounds per square inch, an elongation of 190%, and a tear strength of 120 pounds per inch. The polymer can be used for accessories, components and catheters for infusion therapy, dialysis, and cardiovascular catheters, in shaving systems, and to coat and coextrude onto metals and plastics. The polymer can be molded for medical devices including electrophoresis sorting devices.

Example 5

To 275 grams of polyoxyethylene diol having a number average molecular weight of 1450 was added 141 grams of polyoxyethylene diol having an average molecular weight of 1000, 84 grams of polyoxyethylene diol having an average molecular weight of 600, 57 grams of polyoxyethylene diol having an average molecular weight of 400, 275 grams of polyoxypropylene diol with trademark of Acclaim 2200, having an average molecular weight of 2000, and 136 grams of ethylene glycol. The mixture was analyzed for water and water was added to bring the total to 7.3 grams. To the mixture was added 841 grams of methylene bis (cyclohexyl4-isocyanate). The mixture was heated to 50° C. and 2.7 cc of stannous octoate was added. The mixture was allowed to exotherm and then was heated in oven for one hour at 100° C.

The polymer was cut into strips, granulated and extruded in laboratory Killian extruder. The extruded polymer was granulated. The polymer had a water content of 29% and an expansion of 11% after 24 hours in water. The granulated extruded polymer was thermopressed into plaques for hardness and stress-strain testing. The Shore A hardness of dry polymer was 98, Shore D Hardness of 54 and that for the wet polymer was 86A. The dry strength properties were a tensile strength of 4880 and an elongation of 380%, and a tear strength of 560 pounds per inch, and wet strength properties of 2680 pounds per square inch, an elongation of 350% and a tear strength of 320 pounds per inch. The polymer was dissolved in 95/5 ethanol/water solution at a concentration of 2.5% and 2.5% of Sparwite W, based on the polymer, was suspended in the solution. Then, clean butadiene/nitrile/acid gloves were dipped into the solution. The gloves were baked at about 80° C. to bake off the solvent. The gloves had improved dry and wet donnability. The same procedure can be used for other synthetic rubber and latex rubber gloves and products including but not limited to styrene/butadiene/styrene terpolymers, and thermoplastics. Also, the gloves can be topcoated with a solution of polymer from Examples 22 and 23 containing about 2.5% of ZeoChem 4 micron filler to improve donnability.

Example 6

To 310 grams of polyoxyethylene diol having a number average molecular weight of 1450 was added 310 grams of polyoxyethylene diol having an average molecular weight of 4500, 186 grams of polyoxypropylene diol having an average molecular weight of 2025, 252 grams of polyoxypropylene diol having an average molecular weight of 1025, and 97 grams of ethylene glycol. The mixture was analyzed for water. Water was added to bring the total to 7.6 grams, and 654 grams of methylene bis(cyclohexyl-4-isocyanate) was added. The NCO/OH ratio was 0.95. The mixture was heated to 50° C. and 2.7 cc of stannous octoate was added. The mixture was allowed to exotherm and then was heated in oven for one hour at 100° C.

The polymer was cut into strips, granulated and extruded in laboratory Killian extruder. The extruded polymer was granulated. The polymer had a water content of 45% and an expansion of 23% after 24 hours in water. The granulated extruded polymer was pressed into plaques for hardness and stress-strain testing. The Shore A hardness of dry polymer was 77, and that for the wet polymer was 64. The dry strength properties were a tensile strength of 3890 and an elongation of 550%, and a tear strength of 290 pounds per inch, and wet strength properties of 2240 pounds per square inch, an elongation of 390% and a tear strength of 190 pounds per inch.

Example 7

To 296 grams of polyoxyethylene diol having a number average molecular weight of 1450 was added 297 grams of polyoxyethylene diol having an average molecular weight of 4500, 102 grams of polyoxytetramethylene diol having an average molecular weight of 2000, 125 grams of polyoxytetramethylene diol having an average molecular weight of 1000, 43 grams of polyoxypropylene diol with the trademark of Acclaim 2200, having an average molecular weight of 2000, 193 grams of polyoxypropylene diol having an average molecular weight of 1025, and 97 grams of ethylene glycol. The mixture was analyzed for water, water was added to bring the total to 7.0 grams, and 733 grams of methylene bis(cyclohexyl-4-isocyanate) was added. The ratio of NCO to OH groups to 0.95. The mixture was heated to 54° C. and 2.7 cc of stannous octoate was added. The mixture was allowed to exothern and then was heated in oven for one hour at 100° C. The polymer was cut into strips, granulated and extruded in laboratory Killian extruder. The extruded polymer was granulated. The polymer had a water content of 42% and an expansion of 22% after 24 hours in water. The granulated extruded polymer was pressed into plaques for hardness and stress-strain testing. The Shore A hardness of dry polymer was 65 and that of wet polymer was 65. The dry strength properties were a tensile strength of 2210 and an elongation of 450%, and a tear strength of 220 pounds per inch, and wet strength properties of 2120 pounds per square inch, an elongation of 320%, and a tear strength of 210 pounds per inch. The polymer was made with 30% barium sulfate and extruded into a tough tubing for use in biliary and urinary stents. The polymer can be extruded into tubing for use in accessories and components and infusion therapy catheters, dialysis catheters, urinary catheters and stents, and cardiovascular catheters.

Example 8

To 91 grams of polyoxyethylene diol having a number average molecular weight of 1450 was added 414 grams of Acclaim 2200, polyoxypropylene diol having an average molecular weight of 2000, and 53 grams of ethylene glycol. The mixture was analyzed for water. Water was added to bring the total to 5.66 grams, and 372 grams of methylene bis(cyclohexyl-4-isocyanate) was added. The ratio of NCO to OH groups was 0.98. The mixture was heated to 50° C. and 1.36 cc of stannous octoate was added. The mixture was allowed to exotherm and then was heated in oven for one hour at 100° C.

The polymer was cut into strips, granulated and extruded in laboratory Killian extruder. The extruded polymer was granulated. The polymer had a water content of 5.0% and an expansion of 1.5% after 24 hours in water. The granulated extruded polymer was pressed into plaques for hardness and stress-strain testing. The Shore A hardness of dry polymer was 90 and that of wet polymer was 80. The dry strength properties were a tensile strength of 2630 and an elongation of3 10%, and a tear strength of 410 pounds per inch, and wet strength properties of 1490 pounds per square inch, an elongation of 270%, and a tear strength of 320 pounds per inch. The polymer can be used for accessories, components and catheters for infusion therapy, dialysis, and cardiovascular catheters, in shaving systems, and to coat and coextrude onto metals and plastics. The polymer can be molded for medical devices including electrophoresis sorting devices.

Example 9

To 35.6 grams of polyoxyethylene diol having a number average molecular weight of 1450 was added 35.6 grams of polyoxyethylene diol having a number average molecular weight of 600, 17.8 grams of polyoxyethylene diol having a number average molecular weight of 400, 406 grams of polypropylene diol having the trademark of Acclaim 2200 and having an average molecular weight of 2000, and 52 grams of ethylene glycol. The mixture was analyzed for water. Water was added to bring the total to 3.78 grams, and 357 parts of methylene bis(cyclohexyl-4-isocyanate) were added. The ratio of NCO to OH groups was 0.98. The mixture was heated to 54° C. and 1.36 cc of stannous octoate was added. The mixture was allowed to exotherm and then was heated in oven for one hour at 100° C.

The polymer was cut into strips, granulated and extruded in laboratory Killian extruder. The extruded polymer was granulated. The polymer had a water content of 3.8% and an expansion of 0.9% after 24 hours in water. The granulated extruded polymer was pressed into plaques for hardness and stress-strain testing. The Shore A hardness of dry polymer was 89 and that of wet polymer was 78. The dry strength properties were a tensile strength of 2520 and an elongation of 330%, and a tear strength of 370 pounds per inch, and wet strength properties of 2100 pounds per square inch, an elongation of 400%, and a tear strength of 220 pounds per inch. The polymer can be used for accessories, components and catheters for infusion therapy, dialysis, and cardiovascular catheters, in shaving systems, and to coat and coextrude onto metals and plastics. The polymer can be molded for medical devices including electrophoresis sorting devices.

Example 10

To 182 grams of polyoxyethylene diol having a number average molecular weight of 1450 was added 16 grams of polyoxyethylene diol having a number average molecular weight of 4500, 68 grams of polyoxypropylene diol with the trademark of Acclaim 2200 and having an average molecular weight of 2000, 140 grams of polyoxytetramethylene diol made under the trademark of Terathane 2000 and having a number average molecular weight of 2000, and 171 grams of polyoxytetramethylene diol made under the trademark of Terathane 1000, 113 grams of polyoxypropylene diol having a number average molecular weight of 1025. and 117 grams of ethylene glycol. The mixture was analyzed for water. Water was added to bring the total to 7.27 grams, and 722 parts of methylene bis(cyclohexyl-4-isocyanate) were added. The ratio of NCO to OH groups was 0.95. The mixture was heated to 52° C. and 2.7 cc of stannous octoate was added. The mixture was allowed to exotherm and then was heated in oven for one hour at 100° C.

The polymer was cut into strips, granulated and extruded in laboratory Killian extruder. The extruded polymer was granulated. The polymer had a water content of 35% and an expansion of 18% after 24 hours in water. The extruded polymer was pressed into plaques for hardness and stress-strain testing. The Shore A hardness of dry polymer was 84 and that of wet polymer was 80. The dry strength properties were a tensile strength of 3090 and an elongation of 410%, and a tear strength of 370 pounds per inch, and wet strength properties of a tensile strength of 1800 pounds per square inch, an elongation of 300%, and a tear strength of 300 pounds per inch. The polymer can be used for accessories and components, stents, and catheters used in the medical device field.

The polymer was dissolved in 95/5 ethanol/water solution at a concentration of 2.5% and 2.5% of Sparwite W, based on the polymer, was suspended in the solution. Then, clean butadiene/nitrile/acid gloves were dipped into the solution. The gloves were baked at about 80° C. to bake off the solvent. The gloves had improved dry and wet donnability. The same procedure can be used for other synthetic rubber gloves latex rubber gloves and products including but not limited to styrene/butadiene/styrene terpolymers, and thermoplastics. Also, the gloves can be topcoated with a solution of polymer from Examples 22 and 23 containing about 2.5% of ZeoChem 4 micron filler to improve donnability.

Example 11

To 627 grams of polyoxyethylene diol having a number average molecular weight of 4500 was added 46 grams of polyoxypropylene diol having a number average molecular weight of 2025, 149 grams of polyoxytetramethylene diol made under the trademark of Terathane 2000 and having a number average molecular weight of 2000, and 183 grams of polyoxytetramethylene diol made under the trademark of Terathane 1000, 62 grams of polyoxypropylene diol having a number average molecular weight of 1025. and 102 grams of ethylene glycol. The mixture was analyzed for water. Water was added to bring the total to 7.46 grams, and 639 parts of methylene bis(cyclohexyl-4-isocyanate) were added. The ratio of NCO to OH groups was 0.95. The mixture was heated to 54° C. and 3.4 cc of stannous octoate was added. The mixture was allowed to exotherm and then was heated in oven for one hour at 100° C.

The polymer was cut into strips, granulated and extruded in laboratory Killian extruder. The extruded polymer had a water content of 4.3% and an expansion of 2.4% after 24 hours in water. The granulated extruded polymer was pressed into plaques for hardness and stress-strain testing. The Shore A hardness of dry polymer was 84 and that of wet polymer was 77. The dry strength properties were a tensile strength of 4400 psi and an elongation of 480%, and a tear strength of 320 pounds per inch, and wet strength properties of 1880 pounds per square inch, an elongation of 310%, and a tear strength of 220 pounds per inch. The polymer can be used for accessories and components, stents, and catheters used in the medical device field.

Example 12

To 196 grams of polyoxyethylene diol having a number average molecular weight of 1450 was added 255 grams of polyoxyethylene diol having a number average molecular weight of 4500, 94 grams of polyoxypropylene diol having a number average molecular weight of 1025, 57 grams of polypropylene diol having the trademark of Acclaim 2200 and having an average molecular weight of 2000, and 121 grams of polyoxytetramethylene diol having a number average molecular weight of 2000, 148 grams of polyoxytetramethylene diol having a number average molecular weight of 1000, 10.9 grams of diglycolamine, and 146 grams of ethylene glycol. The mixture was analyzed for water. Water was added to bring the total to 2.73 grams, and 785 grams of methylene bis(cyclohexyl-4-isocyanate) were added. The ratio of NCO to OH groups was 0.98. The mixture was heated to about 54° C. and 2.7 cc of stannous octoate was added. The mixture was allowed to exotherm and then was heated in oven for one hour at 100° C.

The polymer was cut into strips, granulated and extruded in laboratory Killian extruder. The extruded polymer was granulated. The polymer had a water content of 36% and an expansion of 18% after 24 hours in water. The granulated extruded polymer was pressed into plaques for hardness and stress-strain testing. The Shore A hardness of dry polymer was 93 and that of wet polymer was 89. The dry strength properties were a tensile strength of 2520 and an elongation of 330%, and a tear strength of 370 pounds per inch, and wet strength properties of 2100 pounds per square inch, an elongation of 400%, and a tear strength of 220 pounds per inch.

Example 13

To 284 grams of polyoxyethylene diol having a number average molecular weight of 1450 was added 284 grams of polyoxypropylene diol having a number average molecular weight of 1025, 57 grams of polypropylene diol having the trademark of Acclaim 2200 and having an average molecular weight of 2000, 131 grams of polyoxytetramethylene diol having a number average molecular weight of 2000, 160 grams of polyoxytetramethylene diol having a number average molecular weight of 1000, and 140 grams of ethylene glycol. The mixture was analyzed for water. Water was added to bring the total to 7.34 grams, and 810 grams of methylene bis(cyclohexyl-4-isocyanate) were added. The ratio of NCO to OH groups was 0.95. The mixture was heated to about 54° C. and 2.7 cc of stannous octoate was added. The mixture was allowed to exotherm and then was heated in oven for one hour at 54° C.

The polymer was cut into strips, granulated and extruded in laboratory Killian extruder. The extruded polymer was granulated. The polymer had a water content of 13% and an expansion of 5% after 24 hours in water. The granulated extruded polymer was pressed into plaques for hardness and stress-strain testing. The Shore A hardness of dry polymer was 94 and that of wet polymer was 95. The dry strength properties were a tensile strength of 2520 and an elongation of 330%, and a tear strength of 370 pounds per inch, and wet strength properties of 2100 pounds per square inch, an elongation of 400%, and a tear strength of 220 pounds per inch.

Example 14

To 696 grams of polyoxyethylene diol having a number average molecular weight of 8000 was added 50 grams of polyoxyethylene diol having an average molecular weight of 1450, and 25 grams of tripropylene glycol. The mixture was heated under vacuum to reduce the water content to 0.026% and 0.08 gram of water was added to bring the total to .30 gram. Then, 91 parts of methylene bis(cyclohexyl-4-isocyanate) were added. The ratio of NCO to OH groups was 0.92. The mixture was heated to 62° C. and 1.36 cc of stannous octoate was added. The mixture was allowed to exotherm and then was heated in oven for one hour at 100° C.

The polymer was cut into strips and granulated. The polymer was dissolved in water to give a viscosity of about. The polymer can be blended with emulsifiers, oils and vitamins to produce breathable, water-resistant, spreadable creams, lotions, skin barrier and rash-prevention lotions.

Example 15

To 309 grams of polyoxyethylene diol having a number average molecular weight of 8000 was added 22 grams of polyoxyethylene diol having an average molecular weight of 1450, and 21 grams of polyoxypropylene diol having a number average molecular weight of 425 and made under the trademark of PPG 425. The mixture was heated under vacuum to reduce the water content to 0.021% and 0.059 gram of water was added to bring the total to 0.13 gram. Then, 27 parts of methylene bis(cyclohexyl-4-isocyanate)

were added. The ratio of NCO to OH groups was 0.92. The mixture was heated to at 64° C. and 0.68 cc of stannous octoate was added. The mixture was allowed to exotherm and then was heated in oven for one hour at 100° C.

The polymer was cut into strips and granulated. The polymer was soluble in water and provided a low viscosity solution. The polymer can be blended with emulsifiers, oils and vitamins to produce breathable, water-resistant, spreadable creams, lotions, skin barrier and rash-prevention lotions. In one formulation, 97.5 grams of a 2% solution of polymer in water was blended with 1.00 gram of Vitamin E, 1.0 gram of Comfrey, 0.5 gram of Germaben. The mixture was heated up to about 65 C. and mixed for 15–20 minutes at 65° C. Then, it was cooled to at 45° C. and the Germaben was mixed and cooled to room temperature. The mixture is spreadable and forms a water-resistant, breathable film that is useful in pre- and post-shaving preparations, healing cuts and wounds, as a barrier and protective film, for rashes, and to protect fragile skin during medical treatment and testing.

The polymer was dissolved in water at a concentration of 2% of polymer. The thickened aqueous solution was used to cover a cut which had been made with a razor blade. The cut was covered with a Band-Aid. The cut healed within 24 hours, and no whitening of the area around the cut was noted. The cut did not require any further treatment.

To 97.5 grams of the 2% solution of this example was blended 1.0- gram of Vitamin E, 1.0 gram of Lemon (botanical), and 0.5 gram Germaben II. The procedure was heat the solution to 70 C., mix for 30 minutes at 70–73 C., cool to 50 C., and add the Germaben, and cool to room temperature. To prepare a hydrogel cream from this polymer to 20.00 grams of the 2% solution of the polymer was added 2.0 gram of Emersol, 2.5 grams of propylene glycol, 5.00 grams of polawax N.F. made by Croda, 3.00 gram of apricot oil, 2.0 gram of ritachol 1000, 2.00 gram of avocadian, 1.00 gram of lanolin oil, 1.00 gram of pure olive oil, 0.20 gram of sodium hydroxide at 18%, 60.80 gram of distilled water and 0.50 gram of Germaben II. Two drops of fragrance were added after the mixture was made.

The polymer solution and the cream can be used to hasten the healing of cuts and wounds, to enhance donnability of natural and synthetic rubber gloves, and other rubber products, such as condoms, and to lower friction during insertion of needles.

The solutions and creams containing the polymer of this example can be used as medical creams by incorporating different drugs into the lotion after the temperature has been lowered to 40° C. or lower. Drug delivery can be adjusted by the use of oils and other amphiphilic polymers described in this invention.

Example 21

To 398 grams of polyoxyethylene diol having a number average molecular weight of 8000 was added 11 grams of diethylene glycol. The mixture was heated under vacuum to reduce the water content to 0.014% and 0.64 gram of water was added to bring the total to 0.70 gram. Then, 49 grams of methylene bis(cyclohexyl-4-isocyanate) were added. The ratio of NCO to OH groups was 0.96. The mixture was heated to about 63° C. and 0.68 cc of stannous octoate was added. The mixture was allowed to exotherm and then was heated in oven for one hour at 100° C.

The polymer was cut into strips and granulated. The polymer had a viscosity of 950,000 cps at 3% concentration in 60/40 propylene glycol/water. The polymer can be used to coat blood collection containers, metals, plastics including latex gloves, polyurethane, treated nylon and brass, silicon, stainless steel, bronze, copper, polyurethane, treated polyolefins, nonwoven and synthetic fibers. The polymer can be used to modify the surface characteristics of the metals and plastics and increase the slip and biocompatabiltiy of the materials. The polymer was used to modify the surface characteristics of electrophoresis sorting devices, by coating the silicon metal.

A 5% solution of the polymer of Example 21 was prepared in water. The solution can be applied as a solution, lotion and cream to the skin to aid in donnability of rubber products such as gloves and condoms, to rubber and plastic products to enhance their slip and to form a thin layer on the surface of metal, plastic and rubber products. The polymers can be used for rubber gloves to aid donnability, as coatings on razors and strips to aid in reducing friction during shaving. An ethanol solution can be used over the skin to sterilize and also to form a friction reducing surface over the skin.

Example 22

To 398 grams of polyoxyethylene diol having a number average molecular weight of 8000 was added 11 grams of diethylene glycol. The mixture was heated under vacuum to reduce the water content to 0.014% and 0.64 gram of water was added to bring the total to 0.70 gram. The ratio of NCO to OH groups was 0.98. Then, 50 grams of methylene bis(cyclohexyl-4-isocyanate) were added. The mixture was heated to 63° C. and 0.68 cc of stannous octoate was added. The mixture was allowed to exotherm and then was heated in oven for one hour at 100° C.

The polymer was cut into strips and granulated. The polymer had a viscosity of over 2,000,000 cps at 3% in 60/40 propylene glycol/water.

The polymer can be used to coat blood collection containers, metals, plastics including latex gloves, polyurethane, treated nylon and brass, silicon, stainless steel, bronze, copper, polyurethane, treated polyolefins, nonwoven and synthetic fibers. The polymer can be used to modify the surface characteristics of the metals and plastics and increase the slip and biocompatabiltiy of the materials.

Example 23

To 399 grams of polyoxyethylene diol having a number average molecular weight of 8000 was added 11 grams of cyclohexanedimethanol. The mixture was heated under vacuum to reduce the water content to 0.014% and 0.34 gram of water was added to bring the total to 0.39 gram. Then, 38 grams of methylene bis(cyclohexyl-4-isocyanate) were added. The ratio of NCO to OH groups was 0.96. The mixture was heated to 63° C. and 0.68 cc of stannous octoate was added. The mixture was allowed to exotherm and then was heated in oven for one hour at 63° C.

The polymer was cut into strips and granulated. The polymer was insoluble at 3% in 60/40 propylene glycol/water. The polymer can be used to coat metals, plastics including latex gloves, polyurethane, blood collection containers, treated nylon and brass, silicon, stainless steel, bronze, copper, polyurethane, treated polyolefins, nonwoven and synthetic fibers. The polymer can be used to modify the surface characteristics of the metals and plastics and increase the slip and biocompatabiltiy of the materials.

Example 24

To 398 grams of polyoxyethylene diol having a number average molecular weight of 8000 was added 11 grams of diethylene glycol. The mixture was heated under vacuum to reduce the water content to 0.079% and 0.37 gram of water was added to bring the total to 0.70 gram. Then, 49 grams of methylene bis(cyclohexyl-4-isocyanate) were added. The ratio of NCO to OH groups was 0.96. The mixture was heated to 63° C. and 0.68 cc of stannous octoate was added. The mixture was allowed to exotherm and then was heated in oven for one hour at 100° C.

The polymer was cut into strips and granulated. The polymer had viscosities of 62000 cps at 3% in 60/40 propylene glycol/water.

The polymer was dissolved at 2% in 95/5 ethanol/water, and then further diluted with ethanol to about .5% concentration. The solution can be used to coat silicon chips for use in sorting devices. The polymer can be used to coat metals, plastics including latex gloves, polyurethane, treated nylon and brass, silicon, stainless steel, bronze, copper, polyurethane, treated polyolefins, nonwoven and synthetic fibers. The polymer can be used to modify the surface characteristics of the metals and plastics and increase the slip and biocompatabiltiy of the materials.

A 1% solution of this example was prepared in 95/5 ethanol/water. The solution can be applied to rubber and plastic products to enhance their slip and to form a thin layer on the surface of metal, plastic and rubber products. The polymers can be used for rubber gloves and aided donnability, and to coat razors and strips. The coated strip had improved slip. An ethanol solution can be used over the skin to sterilize and also to form a friction reducing surface over the skin. The solution can be applied to hands to lower skin friction prior to insertion of needles. Anti-bactericides and can be blended into the solution to enhance its use in medical device applications and drug delivery. Also, other compounds can be blended into the solution so that the polymer compound coats needles and syringes, permitting their use several times after the initial use in an emergency, or where cost of the needles and syringe is a factor, without fear of contamination. The anti-batcteria and anti-virus compound would remain in the coating and slowly elute out from the coating.

Example 25

To 91 grams of polyoxyethylene diol having a number average molecular weight of 1450 was added 556 grams of polyoxypropylene diol made under the trademark of Acclaim 2200 and having an average molecular weight of 2000, 163 grams of polyoxytetramethylene diol having an average molecular weight of 2000, 200 grams of polyoxytetramethylene diol having an average molecular weight of 1000, and 106 grams of ethylene glycol. The mixture was analyzed for water and water was added to bring the total to 7.7 grams. Then 693 grams of methylene bis(cyclohexyl-4-isocyanate) were added. The ratio of NCO to OH groups was 0.95. The mixture was heated to 50° C. and 2.7 cc of stannous octoate was added. The mixture was allowed to exotherm and then was heated in oven for one hour at 100° C.

The polymer was cut into strips, granulated and extruded in laboratory Killian extruder. The extruded polymer was granulated. The polymer had a water content of 4.8% and an expansion of 2.6% after 24 hours in water. The granulated extruded polymer was pressed into plaques for hardness and stress-strain testing. The Shore A hardness of dry polymer was 87 and 78 for wet polymer. The dry strength properties were a tensile strength of 4330 and an elongation of 520%, and a tear strength of 280 pounds per inch, and wet strength properties of 2530 pounds per square inch, an elongation of 370%, and a tear strength of 240 pounds per inch. The polymer was extruded into a tough and flexible tubing with superior dry and wet strength for use in stents, ports, introducers, infusion therapy, dialysis catheters, cardiovascular catheters, and in accessories and components used in medical devices. The polymers can be used to coat and coextrude metals and plastics. The polymer can also be used in shaving strips, and as primers over hydrophobic substrates. The polymer can be molded into low expansion electrophoresis sorting devices.

Example 26

To 181 grams of polyoxyethylene diol having a number average molecular weight of 1450 was added 284 grams of polyoxypropylene diol made under the trademark of Acclaim 2200 and having an average molecular weight of 2000, 203 grams of polyoxytetramethylene diol having an average molecular weight of 2000, 248 grams of polyoxytetramethylene diol having an average molecular weight of 1000, and 105 grams of ethylene glycol. The mixture was analyzed for water and water was added to bring the total to 7.6 grams. Then 699 grams of methylene bis(cyclohexyl4-isocyanate) were added. The ratio of NCO to OH groups was 0.95. The mixture was heated to 50° C. and 2.7 cc of stannous octoate was added. The mixture was allowed to exotherm and then was heated in oven for one hour at 100° C.

The polymer was cut into strips, granulated and extruded in laboratory Killian extruder. The extruded polymer was granulated. The polymer had a water content of 8% and an expansion of 2.6% after 24 hours in water. The granulated extruded polymer was thermopressed into plaques for hardness and stress-strain testing. The Shore A hardness of dry polymer was 86 and 81 for wet polymer. The dry strength properties were a tensile strength of 3330 pounds per square inch, an elongation of 420%, and a tear strength of 320 pounds per inch, and wet strength properties of 1840 pounds per square inch, an elongation of 380%, and a tear strength of 320 pounds per inch.

The polymer was extruded into a tough, flexible low expandable catheter with superior dry and wet strength for use in infusion therapy, dialysis catheters, cardiovascular catheters, and in accessories and components used in medical devices. The polymers can be used to coat and coextrude metals and plastics. The polymer can also be used in shaving strips, and as primers over hydrophobic substrates, including polyurethanes, latex rubber, synthetic rubber, polyolefins, silicone rubber. The polymer can be used to coat nonwoven cloth, cotton, silk, and polyester. The polymer can be used as a primer for treated and untreated nylon type products, including polyamides, and polyether polyamides. The polymer can be molded into low expansion electrophoresis sorting devices.

Example 27

To 104 grams of polyoxyethylene diol having a number average molecular weight of 1450 was added 220 grams of polyoxypropylene diol made under the trademark of Acclaim 2200 and having an average molecular weight of 2000, 207 grams of polydimethylsiloxanepolyoxyethylene copolymer having a number average molecular weight of about 2400, 186 grams of polyoxytetramethylene diol having an average molecular weight of 2000, 228 grams of polyoxytetramethylene diol having an average molecular weight of 1000, and 121 grams of ethylene glycol. The mixture was analyzed for water and water was added to bring the total to 7.7 grams. Then 744 grams of methylene bis(cyclohexyl-4-isocyanate) were added. The ratio of NCO to OH groups was 0.95. The mixture was heated to 45° C. and 2.7 cc of stannous octoate was added. The mixture was allowed to exotherm and then was heated in oven for one hour at 100° C.

The polymer was cut into strips, granulated and extruded in laboratory Killian extruder. The extruded polymer was granulated. The polymer had a water content of 5.4% and an expansion of 1.3% after 24 hours in water. The granulated extruded polymer was thermopressed into plaques for hardness and stress-strain testing. The Shore A hardness of dry polymer was 97 and 92 for wet polymer. The dry strength properties were a tensile strength of 3430 pounds per square inch, an elongation of 380%, and a tear strength of 410 pounds per inch, and wet strength properties of 2350 pounds per square inch, an elongation of 400%, and a tear strength of 370 pounds per inch The polymer was extruded at about 320° F. into a low-blocking, low tack, tough, flexible low expandable catheter with superior dry and wet strength for use in infusion therapy, dialysis catheters, cardiovascular catheters, and in accessories and components used in medical devices. The polymers can be used to coat and coextrude metals and plastics. Plaques and tubing of the polymer did not stick to each other. The polymer can also be used in shaving strips, and as primers over hydrophobic substrates, including polyurethanes, latex rubber, synthetic rubber, polyolefins, silicone rubber. The polymer can be used to coat nonwoven cloth, cotton, silk, and polyester. The polymer can be used as a primer for treated and untreated nylon type products, including polyamides, and polyether polyamides. The polymer can be molded into low expansion electrophoresis sorting devices.

Example 28

To 92 grams of polyoxyethylene diol having a number average molecular weight of 1450 was added 164 grams of polyoxytetramethylene diol having an average molecular weight of 2000, 201 grams of polyoxytetramethylene diol having an average molecular weight of 1000, 559 grams of polydimethylsiloxanepolyoxyethylene copolymer having a number average molecular weight of about 2400 and 106 grams of ethylene glycol. The mixture was analyzed for water and water was added to bring the total to 7.7 grams. Then 685 grams of methylene bis(cyclohexyl-4-isocyanate) were added. The ratio of NCO to OH groups was 0.95. The mixture was heated to 45° C. and 2.7 cc of stannous octoate was added. The mixture was allowed to exotherm and then was heated in oven for one hour at 100° C.

The polymer was cut into strips, granulated and extruded in laboratory Killian extruder. The extruded polymer was granulated. The polymer had a water content of 20% and an expansion of 7.9% after 24 hours in water. The granulated extruded polymer was thermopressed into plaques for hardness and stress-strain testing. The Shore A hardness of dry polymer was 92 and 84 for wet polymer. The dry strength properties were a tensile strength of 750 pounds per square inch, an elongation of 260%, and a tear strength of 200 pounds per inch, and wet strength properties of 870 pounds per square inch, an elongation of 250%, and a tear strength of 190 pounds per inch.

The polymer was extruded at about 250° F. into a tough, low blocking, low tack, flexible low expandable catheter with superior dry and wet strength for use in infusion therapy, dialysis catheters, cardiovascular catheters, and in accessories and components used in medical devices. The polymers can be used to coat and coextrude metals and plastics. Plaques and tubing of the polymer did not stick to each other. The polymer can also be used in shaving strips, and as primers over hydrophobic substrates, including polyurethanes, latex rubber, synthetic rubber, polyolefins, silicone rubber. The polymer can be used to coat nonwoven cloth, cotton, silk, and polyester. The polymer can be used as a primer for treated and untreated nylon type products, including polyamides, and polyether polyamides. The polymer can be molded into low expansion electrophoresis sorting devices.

Example 29

To 91 grams of polyoxyethylene diol having a number average molecular weight of 1450 was added 556 grams of polyether polycarbonate diol made under the trademark of Poly THF-CD having an average molecular weight of 2000, 163 grams of polyoxytetramethylene diol having an average molecular weight of 2000, 199 grams of polyoxytetramethylene diol having an average molecular weight of 1000, and 106 grams of ethylene glycol. The mixture was analyzed for water and water was added to bring the total to 7.7 grams. Then 693 grams of methylene bis(cyclohexyl-4-isocyanate) were added. The ratio of NCO to OH groups was 0.95. The mixture was heated to 45° C. and 2.7 cc of stannous octoate was added. The mixture was allowed to exotherm and then was heated in oven for one hour at 100° C.

The polymer was cut into strips, granulated and extruded at about 330° F. in laboratory Killian extruder. The extruded polymer was granulated. The polymer had a water content of 3.4% and an expansion of 0.0% after 24 hours in water. The granulated extruded polymer was thermopressed into plaques for hardness and stress-strain testing. The Shore A hardness of dry polymer was 94 and 88 for wet polymer. The dry strength properties were a tensile strength of 4020 pounds per square inch, an elongation of 380%, and a tear strength of 410 pounds per inch, and wet strength properties of 2100 pounds per square inch, an elongation of 340%, and a tear strength of 450 pounds per inch.

The polymer was extruded into a tough, low blocking, flexible low expandable catheter with superior dry and wet strength for use in infusion therapy, dialysis catheters, cardiovascular catheters, and in accessories and components used in medical devices. Plaques of the polymer did not stick to each other. The polymers can be used to coat and coextrude metals and plastics. The polymer can also be used in shaving strips, and as primers over hydrophobic substrates, including polyurethanes, latex rubber, synthetic rubber, polyolefins, silicone rubber. The polymer can be used to coat nonwoven cloth, cotton, silk, and polyester. The polymer can be used as a primer for treated and untreated nylon type products, including polyamides, and polyether polyamides. The polymer can be molded into low expansion electrophoresis sorting devices.

Example 30

To 91 grams of polyoxyethylene diol having a number average molecular weight of 1450 was added 374 grams of polyoxypropylene diol made under the trademark of Acclaim 2200 and having an average molecular weight of 2000, 163 grams of polyoxytetramethylene diol having an average molecular weight of 2000, 200 grams of polyoxytetramethylene diol having an average molecular weight of 1000, 182 grams of polyether polycarbonatediol made under the trademark of Poly THF-CD2000 having an average molecular weight of 2000, and 106 grams of ethylene glycol. The mixture was analyzed for water and water was added to bring the total to 7.7 grams. Then 693 grams of methylene bis(cyclohexyl-4-isocyanate) were added. The ratio of NCO to OH groups was 0.95. The mixture was heated to 45° C. and 2.7 cc of stannous octoate was added. The mixture was allowed to exotherm and then was heated in oven for one hour at 100° C.

The polymer was cut into strips, granulated and extruded about 345° F. in laboratory Killian extruder. The extruded polymer was granulated. The polymer had a water content of 15% and an expansion of 5.3% after 24 hours in water. The granulated extruded polymer was thermopressed into plaques for hardness and stress-strain testing. The Shore D hardness of dry polymer was 52 and 39 for wet polymer. The dry strength properties were a tensile strength of 4450 pounds per square inch, an elongation of 370%, and a tear strength of 500 pounds per inch, and wet strength properties of 3090 pounds per square inch, an elongation of 380%, and a tear strength of 320 pounds per inch.

The polymer was extruded into a tough, flexible, low blocking, low expandable catheter with superior dry and wet strength for use in infusion therapy, dialysis catheters, cardiovascular catheters, and in accessories and components used in medical devices. Plaques of the polymer did not stick to each other. The polymers can be used to coat and coextrude metals and plastics. The polymer can also be used in shaving strips, and as primers over hydrophobic substrates, including polyurethanes, latex rubber, synthetic rubber, polyolefins, silicone rubber. The polymer can be used to coat nonwoven cloth, cotton, silk, and polyester. The polymer can be used as a primer for treated and untreated nylon type products, including polyamides, and polyether polyamides. The polymer can be molded into low expansion electrophoresis sorting devices.

Example 31

To 510 grams of polyoxyethylene diol having a number average molecular weight of 4500 was added 101 grams of polydimethylsiloxane polyoxyethylenecopolymer diol made under the trademark of Q4-3667 and having an average molecular weight of 2400, 140 grams of polyoxytetramethylene diol having an average molecular weight of 2000, 171 grams of polyoxytetramethylene diol having an average molecular weight of 1000, and 136 grams of ethylene glycol. The mixture was analyzed for water and water was added to bring the total to 7.0 grams. Then 748 grams of methylene bis(cyclohexyl-4-isocyanate) were added. The ratio of NCO to OH groups was 0.95. The mixture was heated to 45° C. and 2.7 cc of stannous octoate was added. The mixture was allowed to exotherm and then was heated in oven for one hour at 100° C.

The polymer was cut into strips, granulated and extruded about 310° F. in laboratory Killian extruder. The extruded polymer was granulated. The polymer had a water content of 39% and an expansion of 17% after 24 hours in water. The granulated extruded polymer was thermopressed into plaques for hardness and stress-strain testing. The Shore D hardness of dry polymer was 46 and 32 for wet polymer. The dry strength properties were a tensile strength of 3870 pounds per square inch, an elongation of 470%, and a tear strength of 440 pounds per inch, and wet strength properties of 1790 pounds per square inch, an elongation of 230%, and a tear strength of 270 pounds per inch.

The polymer was extruded at about 310° F. into a low blocking, tough, flexible moderate expandable catheter with superior dry and wet strength for use in infusion therapy, dialysis catheters, cardiovascular catheters, and in accessories and components used in medical devices. The polymers can be used to coat and coextrude metals and plastics. The polymer can also be used in shaving strips, and as primers over hydrophobic substrates, including polyurethanes, latex rubber, synthetic rubber, polyolefins, silicone rubber. The polymer can be used to coat nonwoven cloth, cotton, sil, and polyester. The polymer can be used as a primer for treated and untreated nylon type products, including polyamides, and polyether polyamides. The polymer can be molded into low expansion electrophoresis sorting devices.

Example 32

To 730 grams of polyoxyethylene diol having a number average molecular weight of 8000 was added 52 grams of polyoxyethylene diol having an average molecular weight of 1450. and 46 grams of polyether polycarbonatediol with a number average molecular weight of 250. The mixture was heated under vacuum to reduce the water content to 0.0355% and 0.035 gram of water was added to bring the total to 0.31 gram. Then, 80 grams of methylene bis (cyclohexyl-4-isocyanate) were added. The ratio of NCO to OH groups was 0.92. The mixture was heated to about 65° C. and 1.36 cc of stannous octoate was added. The mixture was allowed to exotherm and then was heated in oven for one hour at 100° C.

The polymer was cut into strips and granulated. The polymer formed a clear solution in water. The solution had a viscosity of 93 cps at 2% concentration in water and a viscosity of 47 cps at 3% concentration in 60/40 propylene glycol/water. The polymer can be used to form skin creams and lotions, hair conditioners, urinary and baby rash creams, and can be used to coat metals, plastics including synthetic and latex rubber gloves, polyurethane, treated nylon and brass, silicon, stainless steel, bronze, copper, polyurethane, treated polyolefins, nonwoven and synthetic fibers. The polymer can be used to modify the surface characteristics of the metals and plastics and increase the slip and biocompatabiltiy of the materials. The polymer was used to modify the surface characteristics of electrophoresis sorting devices, by coating the silicon metal.

The polymer can be dissolved in a solution of 35% propylene glycol, 37% water, 3% polymer and about 25% aluminum chorohydrate. The mixture was used to form an antiperspirant. The polymer extended the period during which fragrance was detected from the film. The polymer can be used in skin and hair care formulations to extend the period of detection of the fragrance.

Example 33

To 792 grams of polyoxyethylene diol having a number average molecular weight of 8000 was added 57 grams of polyoxyethylene diol having an average molecular weight of 1450 and 18.5 grams of polyether polycarbonatediol made by BASF under the tradename of PolyTHFCD1000 with a number average molecular weight of 1000. The mixture was heated under vacuum to reduce the water content to 0.0355% and 0.019 gram of water was added to bring the total to 0.32 gram. Then, 43 grams of methylene bis (cyclohexyl-4-isocyanate) were added. The ratio of NCO to OH groups was 0.92. The mixture was heated to about 65° C. and 1.36 cc of stannous octoate was added. The mixture was allowed to exotherm and then was heated in oven for one hour at 100° C.

The polymer was cut into strips and granulated. The polymer formed a clear solution in water with a viscosity of 870 cps at 2% in water and 275 cps at 3% concentration in 60/40 propylene glycol/water. The polymer can be used to form skin creams and lotions, hair conditioners, urinary and baby rash creams, and can be used to coat metals, plastics including synthetic and latex rubber gloves, polyurethane, treated nylon and brass, silicon, stainless steel bronze, copper, polyurethane, treated polyolefins, nonwoven and synthetic fibers. The polymer can be used to modify the surface characteristics of the metals and plastics and increase the slip and biocompatabiltiy of the materials. The polymer was used to modify the surface characteristics of electrophoresis sorting devices, by coating the silicon metal. The polymer was added at a concentration of 2% to water to form a thin, soft, breathable, nongreasy water-resistant solutions. Higher concentrations form spreadable tough gel that can be used in medical, industrial, and cosmetic applications including but not limited to creams and lotions, shaving preparations, shaving foams, mousse, hair conditioners, antiperspirants, hair styling aids, burn and wound care dressings, as coatings of gloves to ease donnability, and for hands to ease donning of rubber products, and for baby and urinary rashes, Example 34

To 732 grams of polyoxyethylene diol having a number average molecular weight of 8000 was added 57 grams of polyoxyethylene diol having an average molecular weight of 1450. and 9 grams of polyoxypropylene diol having a number average molecular weight of 425. The mixture was heated under vacuum to reduce the water content to 0.014% and 0.202 gram of water was added to bring the total to 0.32 gram. Then, 43 grams of methylene bis(cyclohexyl-4-isocyanate) were added. The ratio of NCO to OH groups was 0.92. The mixture was heated to about 65° C. and 1.36 cc of stannous octoate was added. The mixture was allowed to exotherm and then was heated in oven for one hour at 100° C.

The polymer was cut into strips and granulated. The polymer formed a clear solution in water with a viscosity of 70 cps at 2% in water and 465 cps at 3% concentration in 60/40 propylene glycol/water. The polymer can be used to form skin creams and lotions, hair conditioners, urinary and baby rash creams, and can be used to coat metals, plastics including synthetic and latex rubber gloves, polyurethane, treated nylon and brass, silicon, stainless steel, bronze, copper, polyurethane, treated polyolefins, nonwoven and synthetic fibers. The polymer can be used to modify the surface characteristics of the metals and plastics and increase the slip and biocompatabiltiy of the materials. The polymer was used to modify the surface characteristics of electrophoresis sorting devices, by coating the silicon metal.

The polymer can be dissolved in a solution of 35% propylene glycol, 37% water, 3% polymer and about 25% aluminum chorohydrate. The mixture was used to form an antiperspirant. The polymer extended the period during which fragrance was detected from the film. The polymer can be used in skin and hair care formulations to extend the period of detection of the fragrance.

Example 35

To 792 grams of polyoxyethylene diol having a number average molecular weight of 8000 was added 57 grams of polyoxyethylene diol having an average molecular weight of 1450. and 47 grams of polydimethylsiloxane polyoxyethylene copolymer having a number average molecular weight of 2400. The mixture was heated under vacuum to reduce the water content to 0.0355% and 0.019 gram of water was added to bring the total to 0.32 gram. Then, 43 grams of methylene bis(cyclohexyl-4-isocyanate) were added. The ratio of NCO to OH groups was 0.92. The mixture was heated to about 65° C. and 1.36 cc of stannous octoate was added. The mixture was allowed to exotherm and then was heated in oven for one hour at 100° C.

The polymer was cut into strips and granulated. The polymer had a viscosity of 7 cps at 2% in water and 51 cps at 3% concentration in 60/40 propylene glycol/water. The latter solution had a slight haze and there was foam.

To 47.60 grams of a 10% solution of 154-74 was added 28 grams of ammonium laureth sulfate, 6.90 gram of ammonium lauryl sulfate, Sipoll 22 2.5 gram of cocamide DEA, 10 grams of Seamollient 1115, 0.50 gram of glycol stearate, 9.50 gram cocamidopropyl betain, 0.10 gram of citric acid, 0.10 gram vitamin A palmitate, 0.10 gram of evening primrose, 0.109 gram of vitamin E acetate, 1 0 gram of rosemary, 0.50 gram of collagen, 0.50 gram of protein. The blend was mixed for 20 minutes at 50° C., and 2.50 gram of butylene glycol and methylparaben was added. The mixture was allowed to cool to room temperature. The shampoo was used to wash hair and also as a conditioner. The hair retained its set, was readily combed, and had a nice shine.

To a 35.8 grams of a 10% solution of 154-74 was added 34 gram of ammonium lauryl sulfate, 9.25 grams of 9.25 gram of ammonium laureth sulfate and 0.10 gram of elder flower and camomile, evening primrose. To the solution was added 0.50 rosemary and royal jelly, 0.5 gram of vitamin E acetate. Another solution was made by mixing at 60° C. for 10 minutes 0.75 gram of hydroxyethylcellulose, 3.50 gram of cocamide DEA, 15 gram of water, 0.10 gram of EDTA, 0.40 gram of Germaben II. The solution was added to the first solution. When the mixture cooled to 40° C., 0.20 gram of fragrance was added.

To 30.0 grams of a solution of 10% polymer in water was added 30.0 grams of ammonium lauryl sulfate and 5.00 grams of sodium laureth sulfate. The mixture was heated slowly to 55°–60° C. and kept at this temperature for 20 minutes. To the solution was added 2.5 grams of distilled water and 0.30 gram of hydroxyethyl cellulose over a period of 20 minutes. Then 2.50 grams of cocoamidopropyl betain, 2.00 grams of cetearyl alcohol PEG-150 stearate 1.00 gram of Tween 20, 1.00 gram of Rosemary, 0.50 gram of Panthenol DC, 0.10 gram comfrey, elder flower, evening primrose, camomile, wheat protein, 0.60 gram of vitamin E acetate, 0.30 gram of sodium EDTA, and 0.40 gram of methyl paraben and propyl paraben or the mixture was added to the polymer solution.

In another experiment, 28.000 grams of Acylglutamate CT-12, 8.30 grams of sodium laurylether sulfate, 8.30 grams coconut fatty acid diethanol amide, 7.0 gram citric acid, 10.0 gram of the 10% aqueous polymer solution, 1.00 gram Ajidew N-50, 37.4 gram water and 0.20 gram methyl paraben was heated and mixed at 60° to 65° C. and added to the polymer solution with sulfates. The solution was cooled to 45° C. and perfume was added.

Both solutions were used as shampoo and conditioner and were very good. The hair was readily combed and had a good feel even after three days after washing. The solutions gave good shines and fullness. The hair did not grease up over night. The shampoos were used for two weeks with good results. The shampooed hair remained soft after swimming in chlorinated water.

The polymer can be used to form skin creams and lotions, hair conditioners, urinary and baby rash creams, and can be used to coat metals, plastics including synthetic and latex rubber gloves, polyurethane, treated nylon and brass, silicon, stainless steel, bronze, copper, polyurethane, treated polyolefins, nonwoven and synthetic fibers. The polymer be used to coat cloth to obtain breathability and water repellency, and can be used to modify the surface characteristics of the metals and plastics and increase the slip and biocompatabiltiy of the materials. The polymer was used to modify the surface characteristics of electrophoresis sorting devices, by coating the silicon metal.

A 5% dispersion of the polymer of this example was prepared in water. The solution was applied to the hands after wetting the hands and patting on a paper towel. Donnability was enhanced because of the slip of the polymer and its high water absorptivity. The solution can be applied to hands to lower skin friction prior to insertion of needles.

Example 36

To 212 grams of polyoxyethylene diol having a number average molecular weight of 1450 was added 271 grams of polyoxypropylene diol made under the trademark of Acclaim 2200 and having an average molecular weight of 2000, 279 grams of polyoxytetramethylene diol having an average molecular weight of 1450, and 164 grams of ethylene glycol. The mixture was analyzed for water and water was added to bring the total to 7.2 grams. Then 882 grams of methylene bis(cyclohexyl-4-isocyanate) were added. The ratio of NCO to OH groups was 0.95. The mixture was heated to 51° C. and 2.7 cc of stannous octoate was added. The mixture was allowed to exotherm and then was heated in oven for one hour at 100° C.

The polymer was cut into strips, granulated and extruded in laboratory Killian extruder. The extruded polymer was granulated. The polymer had a water content of 2.7% and an expansion of 0.0% after 24 hours in water. The granulated extruded polymer was pressed into plaques for hardness and stress-strain testing. The Shore D hardness of dry polymer was 59 and 59 for wet polymer. The dry strength properties were a tensile strength of 3320 and an elongation of 260%, and a tear strength of 410 pounds per inch, and wet strength properties of 2460 pounds per square inch, an elongation of 280%, and a tear strength of 530 pounds per inch. The polymer was extruded into a tough and flexible tubing with superior dry and wet strength for use in stents, ports, introducers, infusion therapy, dialysis catheters, cardiovascular catheters, and in accessories and components used in medical devices. The polymers can be used to coat and coextrude metals and plastics. The polymer can also be used in shaving strips, and as primers over hydrophobic substrates. The polymer can be molded into low expansion electrophoresis sorting devices.

The natural rubber gloves were dipped into 75/25 tetrahydrofuran/ethanol solution for five seconds. The solution contained 4% the polymer of this example, 10% Purmol 5A, 10% Armeen 16D, and 10% polyvinylpyrrolidone, based upon polymer solids. The gloves were allowed to dry for 30 minutes and heated at 100° C. for seven minutes. The gloves were allowed to cool at room temperature. The gloves had damp and wet donnability, comparable to those without the Armeen 16D.

Example 37

To 792 grams of polyoxyethylene diol having a number average molecular weight of 8000 was added 57 grams of polyoxyethylene diol having an average molecular weight of 1450. and 19 grams of polydimethylsiloxane polyoxyethylene copolymer having a number average molecular weight of 2400. The mixture was heated under vacuum to reduce the water content to 0.0355% and 0.019 gram of water was added to bring the total to 0.32 gram. Then, 43 grams of methylene bis(cyclohexyl-4-isocyanate) were added. The ratio of NCO to OH groups was 0.92. The mixture was heated to about 65° C. and 1.36 cc of stannous octoate was added. The mixture was allowed to exotherm and then was heated in oven for one hour at 100° C.

The polymer was cut into strips and granulated. The polymer had a viscosity of 10 cps at 2% in water and 91 cps at 3% concentration in 60/40 propylene glycol/water. The latter solution was slightly hazy and foamy. The polymer can be used to form skin creams and lotions, hair conditioners, urinary and baby rash creams, and can be used to coat metals, plastics including synthetic and latex rubber gloves, polyurethane, treated nylon and brass, silicon, stainless steel, bronze, copper, polyurethane, treated polyolefins, nonwoven and synthetic fibers. The polymer be used to coat cloth to obtain breathability and water repellency, and can be used to modify the surface characteristics of the metals and plastics and increase the slip and biocompatabiltiy of the materials. The polymer can be used to modify the surface characteristics of electrophoresis sorting devices, by coating the silicon metal.

Example 38

To 721 grams of polyoxyethylene diol having a number average molecular weight of 8000 was added 51 grams of polyoxyethylene diol having an average molecular weight of 1450. and 64 grams of polyoxypropylene diol having a number average molecular weight of 425. The mixture was heated under vacuum to reduce the water content to 0.014% and 0.21 gram of water was added to bring the total to 0.32 gram. Then, 72 grams of methylene bis(cyclohexyl-4-isocyanate) were added. The ratio of NCO to OH groups was 0.92. The mixture was heated to about 65° C. and 1.36 cc of stannous octoate was added. The mixture was allowed to exotherm and then was heated in oven for one hour at 100° C.

The polymer was cut into strips and granulated. The polymer had a viscosity of 800 cps at 2% in water and 310 cps at 3% concentration in 60/40 propylene glycol/water. The solutions were clear. The polymer can be used to form skin creams and lotions, hair conditioners, urinary and baby rash creams, and can be used to coat metals, plastics including synthetic and latex rubber gloves, polyurethane, treated nylon and brass, silicon, stainless steel, bronze, copper, polyurethane, treated polyolefins, nonwoven and synthetic fibers. The polymer be used to coat cloth to obtain breathability and water repellency, and can be used to modify the surface characteristics of the metals and plastics and increase the slip and biocompatabiltiy of the materials. The polymer can be used to modify the surface characteristics of electrophoresis sorting devices, by coating the silicon metal.

Example 39

To 792 grams of polyoxyethylene diol having a number average molecular weight of 8000 was added 57 grams of polyoxyethylene diol having an average molecular weight of 1450 and 18.5 grams of polyoxypropylene diol having a number average molecular weight of 1025. The mixture was heated under vacuum to reduce the water content to 0.036% and 0.019 gram of water was added to bring the total to 0.32 gram. Then, 42 grams of methylene bis(cyclohexyl-4- isocyanate) were added. The ratio of NCO to OH groups was 0.92. The mixture was heated to about 65° C. and 1.36 cc of stannous octoate was added. The mixture was allowed to exotherm and then was heated in oven for one hour at 100° C.

The polymer was cut into strips and granulated. The polymer had a viscosity of 12 cps at 2% in water and 156 cps at 3% concentration in 60/40 propylene glycol/water. The solutions were clear, and the latter solution was foamy. The polymer can be used to form skin creams and lotions, hair conditioners, urinary and baby rash creams, and can be used to coat metals, plastics including synthetic and latex rubber gloves, polyurethane, treated nylon and brass, silicon, stainless steel, bronze, copper, polyurethane, treated polyolefins, nonwoven and synthetic fibers. The polymer can be used to coat cloth to obtain breathability and water repellency, and can be used to modify the surface characteristics of the metals and plastics and increase the slip and biocompatabiltiy of the materials. The polymer can be used to modify the surface characteristics of electrophoresis sorting devices, by coating the silicon metal.

The polymer can be dissolved in a solution of 35% propylene glycol, 37% water, 3% polymer, and about 25% aluminum chorohydrate. The polymer extended the perior during which fragrance was detected from the film.

The polymer can be dissolved in a solution of 35% propylene glycol, 37% water, 3% polymer and about 25% aluminum chorohydrate. The mixture was used to form an antiperspirant. The polymer extended the period during which fragrance was detected from the film. The polymer can be used in skin and hair care formulations to extend the period of detection ofthe fragrance.

Example 40

To 768 grams of polyoxyethylene diol having a number average molecular weight of 8000 was added 54 grams of polyoxyethylene diol having an average molecular weight of 1450. and 46 grams of polyether polycarbonatediol made under the tradename of PolyTHF CD1000 and having a number average molecular weight of 1000. The mixture was heated under vacuum to reduce the water content to 0.0355% and 0.017 gram of water was added to bring the total to 0.31 gram. Then, 48 grams of methylene bis (cyclohexyl-4-isocyanate) were added. The ratio of NCO to OH groups was 0.92. The mixture was heated to about 65° C. and 1.36 cc of stannous octoate was added. The mixture was allowed to exotherm and then was heated in oven for one hour at 100° C.

The polymer was cut into strips and granulated. The polymer formed a clear gel in water with a viscosity of 870 cps at 2% in water and 1120 cps at 3% concentration in 60/40 propylene glycol/water. The polymer can be used to form skin creams and lotions, hair conditioners, urinary and baby rash creams, and can be used to coat metals, plastics including synthetic and latex rubber gloves, polyurethane, treated nylon and brass, silicon, stainless steel, bronze, copper, polyurethane, treated polyolefins, nonwoven and synthetic fibers. The polymer can be used to modify the surface characteristics of the metals and plastics and increase the slip and biocompatabiltiy of the materials. The polymer was used to modify the surface characteristics of electrophoresis sorting devices, by coating the silicon metal.

The polymer was added at a concentration of 2% to water and formed a clear gel with a viscosity of 196,000 cps. The gel was readily spread over the hand to form a thin, soft, breathable, nongreasy, water-resistant tough gel. The gel had a pH of 3.5.

The polymer was blended at 2% in water with 10% cottonseed oil to form a creamy spreadable emulsion. The cream was readily spread over the hand to form a thin, soft, tough, breathable, water-repellant, non-greasy film.

Twenty grams of a 2% solution of the polymer in water was mixed with 10 grams of mineral oil and 70 grams of water. The lotion had a viscosity of 455 cps. and a pH of 3.5 at room temperature. Seventy grams of a 2% solution of the polymer in water was added to 12 grams of oil, 17.5 grams of water and 0.5 gram of Germaben. The cream had a viscosity of 9,200 cps and a pH of 3.5 at room temperature. The creams, lotions, and solution can be used in medical, industrial, and cosmetic applications including but not limited to creams and lotions, shaving foams, pre- and post-shaving preparations, skin cleansers, hair conditioners, antiperspirants, hair styling aids, burn and wound care dressings, coatings of gloves to facilitate donnability, coatings of hands for donnability of rubber products, and for baby and urinary rashes.

To 60 grams of a 2% solution of the polymer of this example was added 10 grams of mineral oil, 2 grams of Lexol GT, 1 gram of Lexol 1-M, 4 grams of wax, 22 grams of distilled water, 0.5 gram of Ajidew 50, and 0.5 gram of Germaben II. To prepare a collagen gel, to 98.0 grams of a 2% solution of the polymer of this example was added 0.5 gram of Germaben, 1.0 gram of collagen and 0.5 gram of Ajidew 50. Both mixtures can be used as medical creams in drug delivery systems, to aid in healing and to apply to the skin to aid in donnability of rubber products, and to decrease friction during needle applications.

To 60 grams of a 2% solution of the polymer of this example can be added 10 grams of mineral oil, 2 grams of Lexol GT, 1 gram of Lexol 1-M, 4 grams of wax, 22 grams of distilled water, 0.5 gram of Ajidew 50, and 0.5 gram of Germaben II. To prepare a collagen gel, to 98.0 grams of a 2% solution of the polymer of this example can be added 0.5 gram of Germaben, 1.0 gram of collagen and 0.5 gram of Ajidew 50. Both mixtures can be used as medical creams in drug delivery systems, to aid in healing and to apply to the skin to aid in donnability of rubber products, and to decrease friction during needle applications.

Example 41

To 851 grams of polyoxypropylene diol made under the trademark of Acclaim 2200 and having an average molecular weight of 2000 was added 187 grams of polyoxyethylene diol having an average molecular weight of 8000, and 109 grams of ethylene glycol. The mixture was analyzed for water and water was added to bring the total to 7.7 grams. Then 662 grams of methylene bis(cyclohexyl4-isocyanate) was added. The ratio of NCO to OH groups was 0.95. The mixture was heated to 50° C. and 2.7 cc of stannous octoate was added. The mixture was allowed to exotherm and then was heated in oven for one hour at 100° C.

The polymer was cut into strips, granulated and extruded in laboratory Killian extruder. The extruded polymer was granulated. The polymer had a water content of 13% and an expansion of 5% after 24 hours in water. The granulated extruded polymer was pressed into plaques for hardness and stress-strain testing. The Shore A hardness of dry polymer was 80 and 70 for wet polymer. The dry strength properties were a tensile strength of 2390 and an elongation of 450%, and a tear strength of 310 pounds per inch, and wet strength properties of 1480 pounds per square inch, an elongation of 380%, and a tear strength of 230 pounds per inch. The polymer was extruded into a tough and flexible tubing with superior dry and wet strength for use in stents, ports, introducers, infusion therapy, dialysis catheters, cardiovascular catheters, and in accessories and components used in medical devices. The polymers can be used to coat and coextrude metals and plastics. The polymer can also be used in shaving strips, and as primers over hydrophobic substrates. The polymer can be molded into low expansion electrophoresis sorting devices.

Example 42

To 801 grams of polyoxyethylene diol having a number average molecular weight of 8000 was added 57 grams of polyoxyethylene diol having an average molecular weight of 1450 and 9.1 grams of polyether polycarbonatediol made by Nippolly America under the tradename of Nippollan 981 and having a number average molecular weight of 1000. The mixture was heated under vacuum to reduce the water content and 0.053 gram of water was added to bring the total to 0.321gram. Then, 42 grams of methylene bis(cyclohexyl-4-isocyanate) were added. The ratio of NCO to OH groups was 0.92. The mixture was heated to about 68° C. and 1.4 cc of stannous octoate was added. The mixture was allowed to exotherm and then was heated in oven for one hour at 100° C.

The polymer was granulated and mixed with water at a 2% concentration. The clear solution had a viscosity of 110,000 cps, and a clear solution of 5% polymer in 60/40 propylene glycol/water had a viscosity of 36,000 cps at 3%.

The aqueous gel was readily spread over the hand to form a thin, soft, breathable, nongreasy, water-resistant tough gel. The gel had a pH of 7.0.

To 1.76 grams of polymer was added at about 80° C. with 12 grams of cottonseed oil and 87.5 grams of water. To the blend was added 0.5 gram of Germaben at a lower temperature. The blend formed a creamy spreadable emulsion. The cream was readily spread over the hand to form a thin, soft, tough, breathable, water-repellant, non-greasy film.

Face make-up solutions were made using the polymer of this example. The polymer was mixed with 10.00 grams of cyclomethicone, 12.00 grams of propylene glycol, 2.00 grams of the polymer of this example, and 76.00 grams of water. In a second solution 5.00 grams of cyclomethicone, 15.00 grams of propylene glycol, 2.00 grams of the polymer of this example, and 678 grams of water were mixed together. For a third solution, 10.00 grams of cyclomethicone, 12.00 grams of propylene glycol, 3.00 grams of Ex. 43, and 77.00 grams of water were mixed together.

Another mixture for make-up was made using 87.45 grams of a 2% solution of Example 43 in water, 10.00 grams of Silicone SM2101, 0.50 gram Germaben, and 0.05 gram of Quaternium-7. Thirty grams of Solution Nol 3 was mixed with 39.30 grams of talc, 5.00 grams of titanium D, 25.00 grams of chroma lite bronze, 0.50 grams of Germaben II-E, 0.30 gram of octyl dimethyl PABA. The mix formed a spreadable wet make-up.

The polymer of this example was dissolved in water and can be used to cover cuts after stopping the bleeding with some first aid cream and a shaving stick without using any Band-Aid. The film forms a breathable, oxygen transmitting, bacteria protection film which hastens the healing process.

To the solution can be added zinc oxide to form an antiseptic environment which further hastens the healing process, and which film may not require the protection of a Band-Aid. Further the area around the cut remains free of any whitening or possible pus formation. The lotion can be used as after medical professionals wash their hands to enhance the donnability of gloves. The film absorbs water rapidly and forms a slippery film that aids in donning. The lotion can be applied to the skin prior to insertion of a needle to enhance insertion and reduce skin friction. The creams can be used as medical creams by incorporating different drugs into the lotion after the temperature has been lowered to 40° C. or lower. Drug delivery can be adjusted by the use of oils and other amphiphilic polymers described in this invention.

The polymer can be dissolved in a solution of 35% propylene glycol, 37% water, 3% polymer and about 25% aluminum chorohydrate. The mixture was used to form an antiperspirant. The polymer extended the period during which fragrance was detected from the film. The polymer can be used in skin and hair care formulations to extend the period of detection of the fragrance.

Example 43

To 752 grams of polyoxyethylene diol having a number average molecular weight of 8000 was added 54 grams of polyoxyethylene diol having an average molecular weight of 1450 and 46 grams of polydimethylsiloxane polyoxyethylene copolymer made by Dow Corning under the trade name of Q4-3667 and having a number average molecular weight of 2440. The mixture was heated under vacuum to reduce the water content and 1.2 gram of water was added to bring the total to 1.4 gram. Then, 56 grams of methylene bis (cyclohexyl-4-isocyanate) were added. The ratio of NCO to OH groups was 0.92. The mixture was heated to about 68° C. and 1.4 cc of stannous octoate was added. The mixture was allowed to exotherm and then was heated in an oven for one hour at 100° C.

The polymer was cut into strips and granulated. The polymer formed a slightly hazy dispersion at 2% in water with a viscosity of 870 cps and at 3% in 60/40 propylene glycol/water with a viscosity of 130 cps. The polymer can be used for cosmetic, pharmaceutical and industrial applications, and as coatings and in skin and hair care formulations.

A 5% solution of the polymer of this example was prepared in water. The solution can be applied as a solution, lotion and cream to the skin to aid in donnability of rubber products such as gloves and condoms, to rubber and plastic products to enhance their slip and to form a thin layer on the surface of metal, plastic and rubber products. The solution was applied to the hands after wetting the hands and patting on a paper towel. Donnability of coated and uncoated rubber gloves was enhanced because of the slip of the polymer and its high water absorptivity. The solution can be applied to hands to lower skin friction prior to insertion of needles. The polymers can be used to coat rubber gloves to aid donnability, as coatings on razors and strips to aid in reducing friction during shaving. An ethanol solution can be used to sterilize and also to form a low friction surface on the skin.

Example 44

To 764 grams of polyoxyethylene diol having a number average molecular weight of 8000 was added 55 grams of polyoxyethylene diol having an average molecular weight of 1450 and 45 grams of polydimethylsiloxane polyoxyethylene copolymer made by Dow Corning under the trade name of Q4-3667 and having a number average molecular weight of 2440. The mixture was heated under vacuum to reduce the water content and 0.032 gram of water was added to bring the total to 0.31 gram. Then, 44 grams of methylene bis (cyclohexyl-4-isocyanate) were added. The ratio of NCO to OH groups was 0.98. The mixture was heated to about 73° C. and 1.3 cc of stannous octoate was added. The mixture was allowed to exotherm and then was heated in an oven for one hour at 100° C.

The polymer was cut into strips and granulated. The polymer formed slightly hazy dispersions at 2% in water with a viscosity of 23 cps and at 3% in 60/40 propylene glycol/water with a viscosity of 136 cps. The polymer can be be used for cosmetic, pharmaceutical and industrial applications, and as coatings and in skin and hair care formulations.

Example 45

To 762 grams of polyoxyethylene diol having a number average molecular weight of 8000 was added 54 grams of polyoxyethylene diol having an average molecular weight of 1450. and 45 grams of polydimethylsiloxane polyoxyethylene copolymer made by GE under the tradename of GE Silicone 1161 with a number average molecular weight of 1170 were mixed together. The mixture was heated under vacuum to reduce the water content and 0.10 gram of water was added to bring the total to 0.31 gram. Then, 46 grams of methylene bis(cyclohexyl-4-isocyanate) were added. The ratio of NCO to OH groups was 0.92. The mixture was heated to about 75° C. and 1.3 cc of stannous octoate was added. The mixture was allowed to exotherm and then was heated in oven for one hour at 100° C.

The polymer was granulated and mixed at 2% concentration in water to form a dispersion having a viscosity of 130 cps and mixed with 60/40 propylene glycovwater at 3% to form a clear solution with a viscosity of 290 cps. The polymer can be used for hair and skin care.

Example 46

To 354 grams of polyether polycarbonatediol made by Nippolly America under the tradename of Nippollan 980 and having an average molecular weight of 2000 was added 354 grams of polyoxyethylene diol having an average molecular weight of 1450, 164 grams of polyoxytetramethylene diol having a number average molecular weight of 2000, 200 grams of polyoxytetramethylene diol having a number average molecular weight of 1000 and 175 grams of ethylene glycol. The mixture was analyzed for water and water was added to bring the total to 9.2 grams. Then 1013 grams of methylene bis(cyclohexyl-4-isocyanate) was added. The ratio of NCO to OH groups was 0.95. The mixture was heated to 45° C. and 3.4 cc of stannous octoate was added. The mixture was allowed to exotherm and then was heated in oven for one hour at 100° C.

The polymer was cut into strips, granulated and extruded at a die temperature of 340° F. in laboratory Killian extruder. The extruded polymer was granulated. The polymer had a water content of 5% and an expansion of 2.6% after 24 hours in water. The granulated extruded polymer was pressed into plaques for hardness and stress-strain testing. The Shore D hardness of dry polymer was 62 and 49 for wet polymer. The dry strength properties were a tensile strength of 4560 and an elongation of 300%, and a tear strength of 650 pounds per inch, and wet strength properties of 3800 pounds per square inch, an elongation of 340%, and a tear strength of 460 pounds per inch. The polymer was extruded into a tough and flexible tubing with superior dry and wet strength for use in stents, ports, introducers, infusion therapy, dialysis catheters, cardiovascular catheters, and in accessories and components used in medical devices. The polymers can be used to coat and coextrude metals and plastics. The polymer can also be used in shaving strips, and as primers over hydrophobic substrates. The polymer can be molded into low expansion electrophoresis sorting devices.

Example 47

To 354 grams of polyoxypropylene diol made under the trademark of Acclaim 2200 and having an average molecular weight of 2000 was added 354 grams of polyoxyethylene diol having an average molecular weight of 1450, 164 grams of polyether polycarbonatediol made by Nippolly America under the tradename of Nippollan 980 having a number average molecular weight of 2000, 200 grams of polyether polycarbonatediol made by Nippolly America under the tradename of Nippollan 981 having a number average molecular weight of 1000, and 175 grams of ethylene glycol. The mixture was analyzed for water and water was added to bring the total to 9.2 grams. Then 1013 grams of methylene bis(cyclohexyl-4-isocyanate) was added. The ratio of NCO to OH groups was 0.95. The mixture was heated to 50° C. and 3.4 cc of stannous octoate was added. The mixture was allowed to exotherm and then was heated in oven for one hour at 100° C.

The polymer was cut into strips, granulated and extruded at a die temperature of 310° F. in laboratory Killian extruder. The extruded polymer was granulated. The polymer had a water content of 7% and an expansion of 2.6% after 24 hours in water. The granulated extruded polymer was pressed into plaques for hardness and stress-strain testing. The Shore D hardness of dry polymer was 58 and 45 for wet polymer. The dry strength properties were a tensile strength of 4060 and an elongation of 320%, and a tear strength of 720 pounds per inch, and wet strength properties of 2590 pounds per square inch, an elongation of 310%, and a tear strength of 460 pounds per inch. The polymer was extruded into a tough and flexible tubing with superior dry and wet strength for use in stents, ports, introducers, infusion therapy, dialysis catheters, cardiovascular catheters, and in accessories and components used in medical devices. The polymers can be used to coat and coextrude metals and plastics. The polymer can also be used in shaving strips, and as primers over hydrophobic substrates. The polymer can be molded into low expansion electrophoresis sorting devices.

Example 48

To 765 grams of polyoxyethylene diol having a number average molecular weight of 8000 was added 55 grams of polyoxyethylene diol having an average molecular weight of 1450 and 36 grams of polydimethylsiloxane polyoxyethylene copolymer made by Dow Corning under the trade name of Q4-3667 and having a number average molecular weight of 2440, and 9.1 grams of polyether polycarbonatediol made with hexane diol and made by Nippoly America under the tradename of Nippollan 981 and having a number average molecular weight of 1000. The mixture was heated under vacuum to reduce the water content and water was added to bring the total to 0.31 gram. Then, 43 grams of methylene bis(cyclohexyl-4-isocyanate) were added. The ratio of NCO to OH groups was 0.92. The mixture was heated to about 69° C. and 1.4 cc of stannous octoate was added. The mixture was allowed to exotherm and then was heated in an oven for one hour at 100° C.

The polymer was cut into strips and granulated. The polymer formed slightly hazy dispersion and some foam at 2% in water with a viscosity of 2080 cps and a clear foamy solution at 3% in 60/40 propylene glycol/water with a viscosity of 5700 cps. The polymer can be be used for cosmetic, pharmaceutical and industrial applications, and as coatings and in skin and hair care formulations.

Example 49

To 801 grams of polyoxyethylene diol having a number average molecular weight of 8000 was added 57 grams of polyoxyethylene diol having an average molecular weight of 1450 and 9.1 grams of polyether polycarbonatediol made by Nippoly America under the trade name of Nippollan 981 and having a number average molecular weight of 1000. The mixture was heated under vacuum to reduce the water content and water was added to bring the total to 0.32 gram. Then, 41 grams of methylene bis(cyclohexyl-4-isocyanate) were added. The ratio of NCO to OH groups was 0.92. The mixture was heated to about 73° C. and 1.3 cc of dibutyl tin dilaurate was added. The mixture was allowed to exotherm and then was heated in an oven for one hour at 100° C.

The polymer was cut into strips and granulated. The polymer was mixed with water at a solids of 2% to obtain a solution with some insolubles and a viscosity of 9800 cps and at 3% in 60/40 propylene glycol/water to obtain a viscosity of 1920 cps. The polymer can be used for cosmetic, pharmaceutical and industrial applications, and as coatings and in skin and hair care formulations.

Example 50

To 1541 grams of polyoxyethylene diol made under the trademark of Carbowax 8000 and having an average molecular weight of 8000 was added 43 grams of diethylene glycol. The mixture was analyzed for water and water was added to bring the total to 6.0 grams. Then 226 grams of methylene bis(cyclohexyl-4-isocyanate) was added. The ratio of NCO to OH groups was 0.90. The mixture was heated to 60° C. and 2.7 cc of dibutyl tin dilaurate was added. The mixture was allowed to exotherm and then was heated in oven for one hour at 100° C.

The polymer was cut into strips, granulated and extruded in laboratory Killian extruder. The extruded polymer was granulated. The hydrophilic polymer was extruded into a tough and flexible high slip biocompatible tubing with superior dry and wet strength for use in stents, ports, introducers, infusion therapy, dialysis catheters, cardiovascular catheters, and in accessories and components used in medical devices. The polymers can be used to coat metals and plastics and can be coextruded over metals and plastics. The polymer can be coextruded for use in shaving strips, catheters, valves and the polymer can be used as coatings of rubber products, medical devices, catheters, sorting and drug analysis devices, and heart valves. The polymers have superior biocompatibiltiy, low cell and protein adhesion.

Example 51

To 1532 grams of polyoxyethylene diol made under the trademark of Carbowax 8000 and having an average molecular weight of 8000 was added 43 grams of diethylene glycol. The mixture was analyzed for water and water was added to bring the total to 7.8 grams. Then 260 grams of methylene bis(cyclohexyl-4-isocyanate) was added. The ratio of NCO to OH groups was 0.95. The mixture was heated to 60° C. and 2.7 cc of dibutyl tin dilaurate was added. The mixture was allowed to exotherm and then was heated in oven for one hour at 100° C.

The polymer was cut into strips, granulated and extruded in laboratory Killian extruder. The extruded polymer was granulated. The hydrophilic polymer was extruded into a tough and flexible tubing with superior dry and wet strength for use in stents, ports, introducers, infusion therapy, dialysis catheters, cardiovascular catheters, and in accessories and components used in medical devices. The polymers can be used to coat metals and plastics and can be coextruded over metals and plastics. The polymer can be coextruded for use in shaving strips, catheters, valves and the polymer can be used as coatings of rubber products, medical devices, catheters, sorting and drug analysis devices, and heart valves. The polymers have superior biocompatibiltiy, low cell and protein adhesion.

Example 52

To 781 grams of polyoxyethylene diol having a number average molecular weight of 8000 was added 22 grams of diethylene glycol and 18 grams of polydimethylsiloxane polyoxyethylene copolymer made by Dow Corning under the trade name of Q4-3667 and having a number average molecular weight of 2440. The mixture was heated under vacuum to reduce the water content and 0.57 gram of water was added to bring the total to 0.77 gram. Then, 86 grams of methylene bis(cyclohexyl-4-isocyanate) were added. The ratio of NCO to OH groups was 0.92. The mixture was heated to about 70° C. and 1.4 cc of dibutyl tin dilaurate was added. The mixture was allowed to exotherm and then was heated in an oven for one hour at 100° C.

The polymer was cut into strips and granulated. The polymer dissolved at 3% in 60/40 propylene glycol/water to obtain foamy solution with a viscosity of 130 cps. A blend of 19% polymer in 20/80 propylene glycol/water gave a tough gel for use in wound care dressings, cosmetic and industrial applications. The polymer can be used for cosmetic, pharmaceutical and industrial applications, and as coatings and in skin and hair care and hair conditioner formulations. To 290 grams of 95/5 ethanol solution was added 8.62 grams of the polymers of this example, 1.45 gram of this example, 2.53 grams of Purmol 5A. The natural rubber gloves were dipped into the solution for 10 seconds, allowed to dry for 30 minutes and heated at 80° C for 10 minutes. The gloves were allowed to cool at room temperature. The gloves had good dry, damp and wet donnability.

Example 53

To 740 grams of polyoxyethylene diol having a number average molecular weight of 8000 was added 21 grams of diethylene glycol and 45 grams of polydimethylsiloxane polyoxyethylene copolymer made by Dow Corning under the trade name of Q4-3667 and having a number average molecular weight of 2440. The mixture was heated under vacuum to reduce the water content and 1.65 gram of water was added to bring the total to 1.8 gram. Then, 100 grams of methylene bis(cyclohexyl-4-isocyanate) were added. The ratio of NCO to OH groups was 0.92. The mixture was heated to about 68° C. and 1.4 cc of dibutyl tin dilaurate was added. The mixture was allowed to exotherm and then was heated in an oven for one hour at 100° C.

The polymer was cut into strips and granulated. The polymer dissolved at 3% in 60/40 propylene glycol/water to obtain a hazy, foamy dispersion with a viscosity of 700 cps. A blend of 19% polymer in 20/80 propylene glycol/water gave a tough gel for use in wound care dressings, cosmetic and industrial applications. The polymer can be used for cosmetic, pharmaceutical and industrial applications, and as coatings and in skin care formulations.

Example 54

To 750 grams of polyoxyethylene diol having a number average molecular weight of 8000 was added 21 grams of diethylene glycol and 46 grams of polydimethylsiloxane polyoxyethylene copolymer made by GE Silicones under the trade name of GE 1161 and having a number average molecular weight of 1 170. The mixture was heated under vacuum to reduce the water content and 0.62 gram of water was added to bring the total to 0.77 gram. Then, 91 grams of methylene bis(cyclohexyl4-isocyanate) were added. The ratio of NCO to OH groups was 0.92. The mixture was heated to about 70° C. and 1.4 dibutyl tin dilaurate was added. The mixture was allowed to exotherm and then was heated in an oven for one hour at 100° C.

The polymer was cut into strips and granulated. The polymer dissolved at 3% in 60/40 propylene glycol/water obtain a foamy, hazy dispersion with a viscosity of 104 cps. A blend of 19% polymer in 20/80 propylene glycol/water gave a tough gel for use in wound care dressings, cosmetic and industrial applications. The polymer can be used for cosmetic, pharmaceutical and industrial applications, and as coatings and in skin and hair care formulations.

Example 55

To 793 grams of polyoxyethylene diol having a number average molecular weight of 8000, was added 57grams of polyoxyethylene diol having an average molecular weight of 1450 and 47 rams of polydimethylsiloxane polyoxyethylenecopolymer made by Dow Corning under the tradename of Q4-3667 and having a number average molecular weight of 2440. The mixture was heated under vacuum to reduce the water content and 0.02 am of water was added to bring the total to 0.31 gram. Then, 41 grams of methylene bis(cyclohexyl-4-isocyanate) were added. The ratio of NCO to OH groups was 0.92. The mixture was heated to about 68° C. and 1.4 cc of stannous octoate was added. The mixture was allowed to exotherm and then was heated in an oven for one hour at 100° C.

The polymer was cut into strips and granulated. The polymer formed a slightly hazy dispersion at 2% in water with a viscosity of 18 cps and at 3% in 60/40 propylene glycol/water with a viscosity of 130 cps. The polymer was used to prepare skin and face creams, to coat rubber latex gloves, to form shampoos, mousse, baby rash creams.

A solution of polymer was made in 95/5 ethanol/water containing 3% of D-6/40, 0.5% of Example 36, and 25% of Zeochem 5A. The solution and dispersion was used to coat synthetic rubber gloves. The gloves had improved donnability for dry, wet, and damp hands compared to standard gloves.

To 312 grams of 95/5 ethanoVwater was added 9.35 grams of Example 56, 1.55 grams of Example 36 and 2.72 grams of Zeochem 5A. The uncoated synthetic nitrile carboxylic acid gloves were dipped into the solution for 10 seconds and allowed to dry at room temperature for 30 minutes and then heated at 80° C. for ten minutes.

The polymer was dissolved at a concentration of 1.5% in 25/75 ethanol/water. To the solution was added 10% polyvinylpyrrolidone and 10% Purmol 5A based on polymer solids. Nonchlorinated latex rubber gloves were dipped into the solution for about five seconds, and then after twenty minutes at room temperature the gloves were placed in an oven at 80° C. for twenty minutes. The gloves were removed and allowed to cool to room temperature. The gloves had excellent dry, damp and wet donnability.

Example 56

To 1427 grams of polyoxyethylene diol having a number average molecular weight of 8000, was added 40 grams of diethylene glycol and 92 grams of polydimethylsiloxane polyoxyethylenecopolymer made by Dow Corning under the tradename of Q4-3667 and having a number average molecular weight of 2440. The mixture was heated under vacuum to reduce the water content and 7.1 gram of water was added to bring the total to 7.7 grams. Then, 249 grams of methylene bis(cyclohexyl-4-isocyanate) were added. The ratio of NCO to OH groups was 0.90. The mixture was heated to about 64° C. and 2.7 cc of dibutyl tin dilaurate was added. The mixture was allowed to exotherm and then was heated in an oven for one hour at 100° C.

The polymer formed a fine foam which was cut into strips and granulated. The polymer was molded into plaques. The plaques had a water absorption of 85% and an expansion of 105% after 24 hours in water. The polymers had dry tensile strengths of 3730, elongation of 660%, and a tear strength of 600 pounds per inch. Corresponding wet properties were 600 psi, 130%, and 230 lb/in. Natural rubber latex catheters coated with the polymer had a coefficient of friction of 0.055.

To 312 grams of 95/5 ethanol solution was added 9.35 grams of the polymers of this example, 1.55 grams of the polymers of this example, and 2.72 grams of Purmol 5A. The nitrile carboxylic acid synthetic rubber gloves were dipped into the solution for 10 seconds, allowed to dry for 30 minutes and heated at 80° C. for 10 minutes. The gloves were allowed to cool at room temperature. The gloves had good dry, damp and wet donnability.

Example 57

To 792 grams of polyoxyethylene diol having a number average molecular weight of 8000, was added 57 grams of polyoxyethylene diol having a number average molecular weight of 1450, and 48 grams of polyoxytetramethylene diol made by DuPont under the tradename of Terathane 650 and having a number average molecular weight of 650. The mixture was heated under vacuum to reduce the water content and 0.06 gram of water was added to bring the total to 0.3 grams. Then, 56 grams of methylene bis(cyclohexyl-4-isocyanate) were added. The ratio of NCO to OH groups was 0.92. The mixture was heated to about 65° C. and 1.4 cc of stannous octoate was added. The mixture was allowed to exotherm and then was heated in an oven for one hour at 100° C.

The polymer was cut into strips and granulated. The polymer had a viscosity of 1390 cps in water, and a viscosity of 88 cps at 3% in 60/40 propylene glycol/water. The polymer can be used for skin care creams and lotions, and can be coated onto rubber products to enhance lubricity and water absorption.

Example 58

To 805 grams of polyoxyethylene diol having a number average molecular weight of 8000, was added 22 grams of diethylene glycol. The mixture was heated under vacuum to reduce the water content and 0.11 gram of water was added to bring the total to 0.3 gram. Then, 72 grams of methylene bis(phenyl-4-isocyanate) (MDI) were added. The ratio of NCO to OH groups was 0.88. The mixture was heated to about 60° C. and 1.4 cc of stannous octoate was added. The mixture was allowed to exotherm and then was heated in an oven for one hour at 100° C.

The polymer was cut into strips and granulated. The polymer was dissolved in 75/25 tetrahydrofuran/ethanol solution at 3% concentration. Natural rubber latex catheters were dipped into the solution and then dried at 100° C. The catheters had a coefficient of friction of 0.050.

Example 59

To 730 grams of polyoxyethylene diol having a number average molecular weight of 8000, was added 51 grams of polyoxyethylene diol having a number average molecular weight of 1450, and 47 grams of polyoxytetramethylene diol made by Nippoloy America under the tradename of CD 250 and having a number average molecular weight of 250. The mixture was heated under vacuum to reduce the water content and 0.04 gram of water was added to bring the total to 0.3 gram. Then, 80 grams of methylene bis(cyclohexyl-4-isocyanate) were added. The ratio of NCO to OH groups was 0.92. The mixture was heated to about 65° C. and 1.4 cc of stannous octoate was added. The mixture was allowed to exotherm and then was heated in an oven for one hour at 100° C.

The polymer was cut into strips and granulated. The polymer had a viscosity of 93 cps in water, and a viscosity of 47 cps at 3% in 60/40 propylene glycol/water. The polymer can be used for skin care creams and lotions, and can be coated onto rubber products to enhance lubricity and water absorption.

Example 60

To 792 grams of polyoxyethylene diol having a number average molecular weight of 8000, was added 57 grams of polyoxyethylene diol having a number average molecular weight of 1450, and 18 grams of polyoxybutylene oxide made by Dow Chemical Company under the tradename of XS1096 and having a number average molecular weight of 2000. The mixture was heated under vacuum to reduce the water content and 0.20 gram of water was added to bring the total to 0.32 gram. Then, 40 grams of methylene bis (cyclohexyl-4-isocyanate) were added. The ratio of NCO to OH groups was 0.92. The mixture was heated to about 65° C. and 1.4 cc of stannous octoate was added. The mixture was allowed to exotherm and then was heated in an oven for one hour at 100° C.

The polymer was cut into strips and granulated. At 2% in water, the polymer had a viscosity of 35 cps in water, and a viscosity of 450 cps at 3% in 60/40 propylene glycol/water. Both solutions were hazy and foamy, indicating that the polymer had formed a dispersion in water. The polymer can be used for hair care, skin and face care creams and lotions, and can be coated onto rubber products to enhance lubricity and water absorption.

Example 61

To 765 grams of polyoxyethylene diol having a number average molecular weight of 8000, was added 55 grams of polyoxyethylene diol having a number average molecular weight of 1450, and 46 grams of polybutylene oxide made by Dow Chemical Company under the tradename of XS1096 and having a number average molecular weight of 2000. The mixture was heated under vacuum to reduce the water content and 0.20 gram of water was added to bring the total to 0.31 gram. Then, 42 grams of methylene bis (cyclohexyl-4-isocyanate) were added. The ratio of NCO to OH groups was 0.92. The mixture was heated to about 65° C. and 1.4 cc of stannous octoate was added. The mixture was allowed to exotherm and then was heated in an oven for one hour at 100° C.

The polymer was cut into strips and granulated. At 2% in water, the polymer had a viscosity of 33 cps in water, and a viscosity of 400 cps at 3% in 60/40 propylene glycol/water. Both solutions were hazy and foamy, indicating that the polymer had formed a dispersion in water. The polymer can be used for hair care, skin and face care creams and lotions, and can be coated onto rubber products to enhance lubricity and water absorption.

Example 62

A batch of 24862 parts of polyoxyethylene diol of 8000 molecular weight and 698 parts of diethylene glycol were added to a five gallon electrically heated reactor. The mixture was heated to 105° C. in order to melt the ingredients. The mixture was allowed to cool to about 175° F. and the water analyzed as 0.094%. Then 174 grams of water was added.

A separate reactor had 3753 parts of methylene bis (cyclohexyl-4-isocyanate). To the diols was added 44 cc of dibutyl tin dilaurate. Then the isocyanate was heated to about 100° F. and the liquids were forced out under nitrogen pressure at about 0.146 ratio. The NCOIOH ratio was 0.58.

The polymer was collected in polypropylene tubs and post polymerized for one hour at 100° C. The polymer was dissolved at 4% in tetrahydrofuran to give a viscosity of 9 cps. Foley catheters coated with the polymer had coefficient of friction of 0.058. A pressed film sample had a water absorption of 91 and a linear expansion of 34%. The polymers was used to coat suture needles and silk sutures, and to coat synthetic and rubber latex gloves. The polymer was dissolved in 60/40 propylene glycol/water at 3% concentration to give a viscosity of about 166 cps, and the polymer formed a tough exceptionally clear gel at 19% concentration in 20/80 propylene glycol/water with improved adhesion for use in bum and wound care dressings, pre- and post-shaving preparations. Gels containing lower concentrations of polymer can be used to keep wounds and bums moist during the healing process. The polymer can be used as a high slip coating for guidewires, razors, catheters, knives, silicon computer chips, and wires for pacers and bone healing electrical units. The polymers can be used in as coatings of metals, plastics, elastomers, including polyolefins, polystyrene, silicone rubber, polyurethane, steel, brass, bronze to enhance slip, adhesion and biocompatibility. The coatings are useful in industrial applications and in medical devices and elastomeric and plastic electrophoresis sorting devices.

To 312 grams of 95/5 ethanol solution was added 9.35 grams of the polymer of this example, and 2.72 grams of Purmol 5A. The natural rubber latex gloves were dipped into the solution for 10 seconds, allowed to dry for 30 minutes and heated at 80° C. for 10 minutes to drive off the solvents. The gloves were allowed to cool at room temperature. The gloves had good dry, damp and wet donnability.

The nitrile carboxylic acid synthetic rubber gloves were dipped for 10 seconds into 90/10 tetrahydrofuran/ethanol of 4% to the polymer of this example, 50% Purmol 5A, and 10% polyvinylpyrrolidone K-90 type, based upon polymer solids. The gloves were allowed to dry for 30 minutes and heated at 80° C. for 10 minutes to drive off the solvents. The gloves were allowed to cool at room temperature. The gloves had good dry, damp and wet donnability.

The nitrile carboxylic acid synthetic rubber gloves were dipped for 10 seconds into 95/5 ethanol/solution of 3% to the polymer of this example, 0.5% of to the polymer of Example 57 and 25% Purmol 5A based upon polymer solids. The gloves were allowed to dry for 30 minutes and heated at 80° C. for 10 minutes to drive off the solvents. The gloves were allowed to cool at room temperature. The gloves had good dry, damp and wet donnability.

The nitrile carboxylic acid synthetic rubber gloves were dipped for 10 seconds into 90/10 tetrahydrofuran/ethanol of 3.2% to the polymer of this example, 50% Purmol 5A, and 10% polyvinylpyrrolidone K-90 type, based upon polymer solids. The gloves were allowed to dry for 30 minutes and heated at 80° C. for 10 minutes. The gloves were allowed to cool at room temperature. The gloves had good dry, damp and wet donnability.

To 290 grams of 95/5 ethanol/water was added 8.6 grams of to the polymer of this example, 1.45 gram of to the polymer of Example 36, and 25% of Purmol 5A, based upon polymer solids. The nitrile carboxylic acid synthetic rubber gloves were dipped for 10 seconds into the solution and then the gloves were removed and allowed to dry for thirty minutes at room temperature. The gloves were heated at an elevated temperature to drive off the solvents. The gloves had much improved donnability for dry, wet, and damp hands compared to standard gloves.

Uncoated silk sutures were dipped into a 75/25 tetrahydrofuran/ethanol solution of 3.2% to the polymer of this example for 20 seconds. The sutures were withdrawn slowly, and allowed to dry overnight at room temperature. The sutures were very slippery.

Suture needles were dipped into a precoat comprising 50 grams of ethyl acetate, 50 grams of Bayer Desmophen 670A-801, and a curing agent of 37 grams of BL3175, 0.02 cc of dibutyltin dilaurate. The needles were allowed to dry at room temperature and then cured for 30 minutes at 140° C. The needles were cooled for 15 minutes at room temperature.

The needles were dipped in a 75/25 tetrahydrofuran/ethanol solution containing 3.2% of the polymer of this example. The needles remained in the solution for 20 seconds, and were removed. The needles were allowed to dry for 15 minutes at room temperature and then heated for 8.5 minutes at 100° C. The needles were removed and allowed to cool overnight. The top coating remained on the base coat, and the base coat adhered to the needle.

The same procedure can be used with to the polymer of this example to coat syringe needles, collectors, scalpels, knives and syringes, other medical devices, stainless steel, other metals, and plastics for use in industrial and other industries. When syringes are coated with this system, anti-bactericides and other anti-bacteria and anti-virus compounds can be incorporated into the coating, permitting their use several times after the initial use in an emergency, or where cost of the needles and syringe is a factor, without fear of contamination. The anti-bacteria and anti-virus compound would remain in the coating and slowly elute out from the coating.

Example 63

To 800 grams of polyoxyethylene diol having a number average molecular weight of 8000, was added 22 grams of diethylene glycol. The mixture was heated under vacuum to reduce the water content and 0.24 gram of water was added to bring the total to 0.55 gram. Then, 85 grams of methylene bis(cyclohexyl-4-isocyanate) were added. The ratio of NCO to OH groups was 0.94. The mixture was heated to about 68° C. and 1.4 cc of dibutyl tin dilaurate was added. The mixture was allowed to exotherm and then was heated in an oven for one hour at 100° C.

The polymer was cut into strips and granulated. The polymer dissolved in water at a 2% concentration. The polymer was used to prepare skin and face creams, to coat rubber latex gloves, to form shampoos, mousse, baby rash creams.

Another make up was made using 5.00 grams of a mixture of 10% cyclomethicone and 90% of 2% of the polymer of this example in water, 0.0125 gram of Germaben II-E, 10.00 gram of talc, 2.00 gram of chroma -Lite brown, 2.00 gram of chroma-Bronze, 0.10 gram of escalol 507 (PABA), 2.00 gram of pearl -gold, 1.00 gram of 10% cyclomethicone, and 90% of 2% emulsion of 2% the polymer of this example in water, and 0.50 gram of propylene glycol. The make-up mixture had good spread and exhibited long lasting cover on the skin. To 96 grams of a 3% solution of the polymer of this example can be added 1 gram of Vitamin E, 1 gram of propylene glycol, 0.50 gram of Ajidew N-50, 1 gram of Comfrey, and 0.50 gram of Germaben II.

Mixture of 10% cyclomethicone and 90% of a 2% solution of the polymer of this example formed an emulsion, that could be readily spread on the skin, forming a breathable, smooth film. Mixture of 10% castor oil and 90% of a 2% solution of the polymer of the example formed an emulsion, that could be readily spread on the skin, forming a breathable, soft and smooth film.

Example 64

To 801 grams of polyoxyethylene diol having a number average molecular weight of 8000, was added 22 grams of diethylene glycol. The mixture was heated under vacuum to reduce the water content and 0.64 gram of water was added to bring the total to 0.78 gram. Then, 79 grams of methylene bis(phenyl-4-isocyanate) were added. The ratio of NCO to OH groups was 0.88. The mixture was heated to about 61° C. The mixture was allowed to exotherm and then was heated in an oven for one hour at 100° C.

The polymer was cut into strips and granulated. Latex rubber catheters were dipped into a 3% solution of polymer in 75/25 tetrahydrofuran/ethanol solution, dried at room temperature, and then heated for about 10 minutes at 100° C. The catheters had a coefficient of friction of 0.038.

Example 65

To 758 grams of polyoxyethylene diol having a number average molecular weight of 8000, was added 54 grams of polyoxyethylene diol having an average molecular weight of 1450, and 45 grams of Q4-3667 made by Dow Corning and having a number average molecular weight of 2440. The mixture was heated under vacuum to reduce the water content and water was added to bring the total to 0.90 gram. Then, 49 grams of methylene bis(cyclohexyl-4-isocyanate) were added. The ratio of NCO to OH groups was 0.92. The mixture was heated to about 70° C. and 1.4 cc of stannous octoate was added. The mixture was allowed to exotherm and then was heated in an oven for one hour at 100° C.

The polymer was cut into strips and granulated. The polymer was dispersed in water at a 2% concentration to obtain a viscosity of 165 cps. A dispersion of the polymer at 3% in 60/40 propylene glycol/water had a viscosity of 150 cps. The polymer was used to prepare skin and face creams, to coat rubber latex gloves, to form shampoos, mousse, baby rash creams. The polymer can be used to coat catheters, rubber products, metals, plastics, skin, hair, and other materials. The polymer can be use in paints as a thickener and to improve brushability.

A 5% dispersion of the polymer of this example was prepared in water. The solution was applied to the hands after wetting the hands and patting on a paper towel. Donnability of coated and uncoated rubber gloves was enhanced because of the slip of the polymer and its high water absorptivity. The polymer can be blended with oils, emollients, fragrances and other materials for application as a lotion and cream. The solution can be applied to hands to lower skin friction prior to insertion of needles. Antibactericides and can be blended into the solution to enhance its use in medical device applications and drug delivery. Also, other compounds can be blended into the solution so that the polymer compound coats needles and syringes, permitting their use several times after the initial use in an emergency, or where cost of the needles and syringe is a factor, without fear of contamination. The anti-batcteria and anti-virus compound would remain in the coating and slowly elute out from the coating.

To 312 grams of 95/5 ethano/water can be added 9.35 grams of the polymers of Example 57, 1.55 grams of the polymers of Example 36 and 2.72 grams of Purmol 5A. Uncoated synthetic nitrile carboxylic acid gloves were dipped into the solution for ten seconds and allowed to dry at room temperature for 30 minutes and then heated at 80° C. for ten minutes. The gloves had improved donnability for dry, wet, and damp hands compared to standard gloves. The polymers can be dispersed in water and added on-line in the preparation of synthetic and natural rubber gloves. The polymers do not require any vulcanization or curing. A cream and lotion made with the polymers formed in Example 66 can be rubbed on the hands after washing and rinsing with water to absorb some of the excess water and to improve damp and dry donnability.

Example 66

To 799 grams of polyoxyethylene diol having a number average molecular weight of 8000, 57 grams of polyoxyethylene diol having an average molecular weight of 1450 and 14 grams of polyether polycarbonate diol made using hexane diol by Nippoloy America, Inc. under the tradename of Nippoloy 981 and having a number average molecular weight of 1000. The mixture was heated under vacuum to reduce the water content and bring the total to 1.4 gram. Then, 39 grams of methylene bis(cyclohexyl4-isocyanate) were added. The ratio of NCO to OH groups was 0.88. The mixture was heated to about 66° C. and 1.4 cc of stannous octoate was added. The mixture was allowed to exotherm and then was heated in an oven for one hour at 100° C.

The polymer was cut into strips and granulated. The polymer dissolved in water a5 2% concentration to obtain a viscosity of 72,000 cps and at 3% in 60/40 propylene glycol/water to obtain a viscosity of 720 cps. The polymer thickened both aqueous media. The polymers forms emulsions in oil and water. The polymer can be used in hair care formulations and to form skin creams, lotions, hair conditioners, shampoos, urinary and baby rash creams and to coat catheters and guidewires.

A 2% solution of the polymers of this example had a viscosity of 72,000 cps and a mixture of 90% of the 2% solution and 10% of cyclomethicone had a viscosity of 1700 cps. A mixture of 95% of the 2% solution of polymer and 5% cyclomethicone had a viscosity of 2400 cps. The mixtures of aqueous solutions of polymer and cyclomethicone were emulsions. The thickening and emulsifying properties of the polymer are shown by these results. The emulsions had good spread, were low in tack, and the films were smooth. The particle was readily reduced using a high shear mixer. The emulsions can be used in skin care and make-up formulations, coatings of metal, hair, skin, and plastics. The polymers can be used as thickening agents for a variety of materials such as lubricants, oils, paints, aqueous and polar media.

Example 67

To 768 grams of polyoxyethylene diol having a number average molecular weight of 8000, 55 grams of polyoxyethylene diol having an average molecular weight of 1450 and 41 grams of polyether polycarbonate diol made using butane diol by Nippoloy America, Inc. under the tradename of Nippoloy CX4010 and having a number average molecular weight of 1000. The mixture was heated under vacuum to reduce the water content and bring the total to 0.24 gram. Then, 44 grams of methylene bis(cyclohexyl-4-isocyanate) were added. The ratio of NCO to OH groups was 0.88. The mixture was heated to about 65° C. and 1.4 cc of stannous octoate was added. The mixture was allowed to exotherm and then was heated in an oven for one hour at 100° C.

The polymer was cut into strips and granulated. The polymer dissolved at 2% in water to obtain a thickened solution with a viscosity of 3,400 cps and at 3% in 60/40 propylene glycol/water with a viscosity of 530 cps. The polymer can be used in hair care formulations and to form skin creams, lotions, hair conditioners, shampoos, urinary and baby rash creams and to coat catheters and guidewires.

Mixture of 10% cyclomethicone and 90% of a 2% solution of the polymer of this example had a viscosity of 47,500 cps. The mixture was an emulsion, that could be readily spread on the skin, forming a breathable, smooth film.

Example 68

A batch of 22582 parts of polyoxyethylene diol of 8000 molecular weight and 745 parts of diethylene glycol were added to a five gallon electrically heated reactor. The mixture was heated to 105° C. in order to melt the ingredients. The mixture was allowed to cool to about 175° F. and the water was analyzed. Then 122 grams of water was added. A separate reactor had 3761 parts of methylene bis(cyclohexyl-4-isocyanate). To the diols was added 41 cc of dibutyl tin dilaurate. Then the isocyanate was heated to about 100° F. and the liquids were forced out under nitrogen pressure at about 0.160 ratio. The NCO/OH ratio was 0.72.

The polymer was collected in polypropylene tubs and post polymerized for one hour at 100° C. The polymer was dissolved at 4% in tetrahydrofuran to give a viscosity of 12.0 cps. Foley catheters coated with the polymer had coefficient of friction of 0.060. The pressed film had water content of 85% and a linear expansion of 96% after 24 hours immersion in water.

The polymer can be used to coat silk and plastic sutures, suture needles, syringe needles, syringe barrells, and synthetic and natural rubber latex gloves. The polymer can be dissolved in 95/5 ethanoVwater and rubber gloves can be dipped into the solution.

Example 69

A batch of 23042 parts of polyoxyethylene diol of 8000 molecular weight and 646 parts of diethylene glycol were added to a five gallon electrically heated reactor. The mixture was heated to about 105° C. in order to melt the ingredients. The mixture was allowed to cool to about 175° F. and the water was analyzed. Then 170 grams of water was added. A separate reactor had 3344 parts of methylene bis(cyclohexyl-4-isocyanate). To the diols was added 41 cc of dibutyl tin dilaurate. Then the isocyanate was heated to about 100° F. and the liquids were forced out under nitrogen pressure at about 0.139 ratio. The NCO/OH ratio was 0.46.

The polymer was collected in polypropylene tubs and post polymerized for one hour at 100° C. The polymer was dissolved at 4% in tetrahydrofuran to give a viscosity of 5.2 cps. The polymer had a water absorption of 92% and a linear expansion of 137% after 24 hours immersion in water. Foley catheters coated with the polymer had a coefficient of friction of 0.040. The polymer can be used to coat silk and plastic sutures, suture needles and synthetic and natural rubber latex gloves, condoms, and other rubber products. The polymer can be dissolved in 95/5 ethanol/water and rubber gloves can be dipped into the solution.

Example 70

A batch of 22533 parts of polyoxyethylene diol of 8000 molecular weight and 744 parts of diethylene glycol were added to a five gallon electrically heated reactor. The mixture was heated to about 105° C. in order to melt the ingredients. The mixture was allowed to cool to about 175° F. and the water was analyzed. Then 169 grams of water was added. A separate reactor had 3753 parts of methylene bis(cyclohexyl-4-isocyanate). To the diols was added 41 cc of dibutyl tin dilaurate. Then the isocyanate was heated to about 100° F. and the liquids were forced out under nitrogen pressure at about 0.161 ratio. The NCO/OH ratio was 0.54.

The polymer was collected in polypropylene tubs and post polymerized for one hour at 100° C. The polymer was dissolved at 4% in tetrahydrofuran to give a viscosity of 6.0 cps. The polymer had a water absorption of 89% and a linear expansion of 116% after 24 hours immersion in water. Foley catheters coated with the polymer had coefficient of friction of 0.050. The polymer can be used to coat silk and plastic sutures, suture and syringe needles and synthetic and natural rubber latex gloves. The polymer can be dissolved in 95/5 ethanol/water and rubber gloves can be dipped into the solution.

Example 71

To 721 grams of polyoxyethylene diol having a number average molecular weight of 8000, was added 51 grams of polyoxyethylene diol having a number average molecular weight of 1450, and 91 grams of Q4-3667, a polydimethylsiloxane polyoxyethylene copolymer a polydimethylsiloxane polyoxyethylene copolymer made by Dow Corning with a polyoxyethylene having a number average molecular weight between about 200 to about 1000 and one to ten dimethylsiloxane groups. The mixture was heated under vacuum to reduce the water content and is 0.08 gram of water was added to bring the total to 0.31 gram. Then, 44 grams of methylene bis(cyclohexyl-4-isocyanate) were added. The ratio of NCO to OH groups was 0.92. The mixture was heated to about 70° C. and 1.4 cc of stannous octoate was added. The mixture was allowed to exotherm and then was heated in an oven for one hour at 100° C.

The polymer was cut into strips and granulated. The polymer was dissolved in water at a 2% concentration to obtain a dispersion with a viscosity of 7 cps and at 3% in 60/40 propylene glycol/water to obtain a dispersion with a viscosity of 51 cps. The polymer can be used to prepare skin and face creams, to coat rubber latex gloves, to form shampoos, mousse, baby rash creams and for medical devices and industrial applications.

To a 95/5 ethanol/water solution was added 1.5% the polymer of Example 22, 1.5% of the polymer of Example 57, and 25% Purmol 5A, based on polymer solids. Uncoated natural rubber gloves were dipped into the solution for 10–15 seconds, allowed to dry at room temperature for 30 minutes and then heated at 85° C. for ten minutes. The gloves had improved donnability for dry, wet, and damp hands compared to standard gloves. The polymers can be dispersed in water and added on-line in the preparation of synthetic and natural rubber gloves. The polymers do not require any vulcanization or curing. Creams and lotions made with the polymer of Example 72 and the polymer of Example 66 can be rubbed on the hands after washing and rinsing with water to absorb some of the excess water and to improve damp and dry donnability.

Nitrile carboxylic acid synthetic rubber gloves were dipped for 10–15 seconds into a 75/25 tetrahydrofuran/ethanol solution containing 3% of the polymer of Example 57 and 50% Purmol 5A, based upon polymer solids. The gloves were allowed to dry for 30 minutes and heated at 85° C. for ten minutes.. The gloves were allowed to cool at room temperautre. The gloves had good dry, damp and wet donnability.

Natural rubber gloves were dipped for 5–7 seconds into a 75/25 tetrahydrofuran/ethanol solution containing 3% of the polymer of Example 57 and 10% cyclomethicone and 50% Purmol 5A, based upon polymer solids. The gloves were allowed to dry for 30 minutes and heated at 100° C. for five minutes.. The gloves were allowed to cool at room temperautre. The gloves had good dry, damp and wet donnability.

Nitrile carboxylic acid synthetic rubber gloves were dipped for 10–15 seconds into an aqueous dispersion of 3% the polymer of Example 66 and 50% Purmol 5A, based upon polymer solids. The gloves were allowed to dry for 30 minutes and heated at 85° C. for ten minutes to drive off the water. The gloves were allowed to cool at room temperature. The gloves had good dry, damp and wet donnability. The polymer of Example 36 and the polymer of Example 56 can be dispersed in water with a filler, and the rubber products can be dipped into the dispersions, dried at room temperature and baked at an elevated temperature to obtain high slip, biocompatible coatings. Dispersions, creams and lotions made with the polymer of Example 72 and the polymer of Example 66 can be rubbed on the hands after washing and rinsing with water to absorb some of the excess water, enhance slip and to improve damp and dry donnability.

Example 72

To 761 grams of polyoxyethylene diol having a number average molecular weight of 8000, was added 54 grams of polyoxyethylene diol having a number average molecular weight of 1450 and 46 grams of GE1161-11-925, a polydimethylsiloxane polyoxyethylene copolymer made by GE Silicones with a polyoxyethylene having a number average molecular weight between about 200 to about 1000 and about one to about ten dimethylsiloxane groups. The mixture was heated under vacuum to reduce the water content to bring the total to 0.33 gram. Then, 46 grams of methylene bis(cyclohexyl-4-isocyanate) were added. The ratio of NCO to OH groups was 0.92. The mixture was heated to about 67° C. and 1.4 cc of stannous octoate was added. The mixture was allowed to exotherm and then was heated in an oven for one hour at 100° C.

The polymer was cut into strips and granulated. The polymer was dissolved in water at a 2% concentration to obtain a dispersion with a viscosity of 17 cps and at 3% in 60/40 propylene glycol/water to obtain a dispersion with a viscosity of 73 cps. The polymer can be used to prepare skin and face creams, to coat rubber latex gloves, to form shampoos, mousse, baby rash creams, and for medical devices and industrial applications.

Example 73

To 711 grams of polyoxyethylene diol having a number average molecular weight of 8000, was added 45 grams of polyoxyethylene diol having a number average molecular weight of 1450, 45 grams of GE1032, a polydimethylsiloxane polyoxyethylene copolymer made by GE Silicones with a polyoxyethylene having a number average molecular weight between about 200 to about 1000 and about one to about ten dimethylsiloxane groups and 20 grams of diethylene glycol. The mixture was heated under vacuum to reduce the water content and 0.09 gram was added to bring the total to 0.32 gram. Then, 86 grams of methylene bis (cyclohexyl4-isocyanate) were added. The ratio of NCO to OH groups was 0.92. The mixture was heated to about 68° C. and 1.4 cc of stannous octoate was added. The mixture was allowed to exotherm and then was heated in an oven for one hour at 100° C.

The polymer was cut into strips and granulated. The polymer can be dissolved in water at a 2% concentration. The polymer can be used to prepare skin and face creams, to coat rubber latex gloves, to form shampoos, mousse, baby rash creams.

Example 74

To 792 grams of polyoxyethylene diol having a number average molecular weight of 8,000, can be added 57 grams of polyoxyethylene diol having an average number molecular weight of 1450, and 48 grams of Silicone 88017 made by GE Silicones and having a number average molecular weight of 700. The mixture can be heated under vacuum to reduce the water content and water can be added to bring the total to 0.32 gram. Then, 55 grams of methylene bis (cyclohexyl-4-isocyanate) can be added. The ratio of NCO to OH groups was 0.92. The mixture can be heated to about 70° C. and 1.4 cc of stannous octoate added. The mixture can be allowed to exotherm and then heated in an oven for about one hour at 100° C.

The polymer can be cut into strips and granulated. The polymer can be dispersed in water at a 2% concentration to obtain a flowable, spreadable aqueous solution. The polymer can be used to prepare skin and face creams, to coat rubber latex gloves, to form shampoos, mousse, baby rash creams. The polymer can be used to coat catheters, rubber products, metals, plastics, skin, hair, and other materials. The polymer can be used in paints as a thickener and to improve brushability.

Example 75

To 319 grams of polyoxyethylene diol having a number average molecular weight of 1450 was added 550 grams of polyoxypropylene diol having a number average molecular weight of 1025 and 407 grams of polyoxypropylene diol having a number average molecular weight of 2025, 212 parts of ethylene glycol and 8.9 parts of water. The mixture was heated with stirring until a homogeneous melt was obtained. Then, 1861 parts of methylene bis-cyclohexyl-4-4'-diisocyanate was added. The NCOIOH ratio was 0.95. When the temperature reached about 50° C., 3.4 ml of stannous octoate (T$_9$) was added, and the mass was allowed to exotherm. The mass was heated at 100° C. for about one hour to complete formation of the polymer. The polymer had a water content of 23% and an expansion of 9% after twenty-four hours in water at room temperature. The polymer was granulated and extruded and pressed into plaques for hardness and stress-strain testing. The shore a hardness of dry polymer was 94 and that of wet polymer was 95. The dry strength properties were a tensile strength of 2520 psi and an elongation of 330%, and a tear strength of 370 pounds per inch, and corresponding wet properties were 2100 psi 400%, and 220 pounds per inch.

The polymer was dissolved in 75/25 tetrahydrofuran/ ethanol solution at a concentration of 7%. Nonwoven tetrafluoroethylene cloth was dipped into the solution for about ten seconds and the cloth was allowed to dry for about fifteen minutes at room temperature then it was heated in an oven at about 100° C. for ten minutes to drive off the solvents. The cloth was allowed to cool to room temperature and then it was placed into a solution of one mg/ml of tissue plasminagen activator in water for about two hours. The coated cloth was placed overnight in an oven at about 35° C. to drive off the water. The cloth can be sterilized with ethylene oxide.

The coated cloth can be used an implant, to suture heart valves to heart and muscle tissue, is and can be used in vascular implants. The polymer can be used to coat catheters and to blend with hydrophobic elastomers. Tubes comprising the coated cloth containing tPA can be used as vascular grafts of carotid arteries. The elution rates for the tPA is significantly lower than that for tPA coated onto bare cloth.

Example 76

To 756 grams of polyoxyethylene diol (PED) having a number average molecular weight of 8000 was added 45 grams of polydimethylsiloxane polyoxyethylenecopolymer having a number average molecular weight of about 780 and 55 grams of polyoxyethylene diol (PED) having a number average molecular weight of 1450. The mixture was heated under vacuum, analyzed for water, and water was added to bring the total to 0.27 gram. Then, 51 grams of methylene bis(cyclohexyl-4-isocyanate) was added at about 70° C. The ratio of NCO to OH groups was 0.92. To the mixture was added 1.4 cc of stannous octoate. The mixture was allowed to exotherm and then was heated in an oven for one hour at 100° C.

The polymers was cut into strips and granulated. The polymer had a viscosity of 5700 cps in water. The polymer can be used as high slip coating for rubber goods such as gloves and condoms, medical products and can be used in absorbents, as gels in wound dressings and to prepare skin and face creams, to form shampoos, mousse, and baby rash creams.

A 2% solution of the polymer in 30/70 ethanol/water was mixed with 25% Purmol A, based on polymer solids. Latex rubber gloves were dipped into the solution, allowed to dry at room temperature and heated at 85° C. for about ten minutes. The coated gloves were very lubricious with wet hands.

The polymer can be dissolved in a solution of 35% propylene glycol, 37% water, 3% polymer and about 25% aluminum chorohydrate. The mixture was used to form an antiperspirant. The polymer extended the period during which fragrance was detected from the film. The polymer can be used in skin and hair care formulations to extend the period of detection of the fragrance.

Example 77

To 747 grams of polyoxyethylene diol (PED) having a number average molecular weight of 8000 was added 45 grams of polydimethylsiloxane polyoxyethylenecopolymer having a number average molecular weight of about 780 and 55 grams of polyoxyethylene diol (PED) having a number average molecular weight of 1450. The mixture was heated under vacuum, analyzed for water, and water was added to bring the total to 0.91 gram. Then, 60 grams of methylene bis(cyclohexyl4-isocyanate) was added at about 70° C. The ratio of NCO to OH groups was 0.92. To the mixture was added 1.4 cc of stannous octoate. The mixture was allowed to exotherm and then was heated in an oven for one hour at 100° C.

The polymers was cut into strips and granulated. The polymer had a viscosity of 59,000 cps in water. The polymer can be used as high slip coating for rubber goods such as gloves and condoms, medical products and can be used in absorbents, as gels in wound dressings and to prepare skin and face creams, to form shampoos, mousse, and baby rash creams.

A 1% solution of the polymer in 30/70 ethanol/water was mixed with 25% Purmol A and 10% PVP, based on polymer solids. Latex rubber gloves were dipped into the solution, allowed to dry at room temperature and heated at 85° C. for about ten minutes. The coated gloves had improved donnability. The polymer can be used to coat razors. The polymer of this example can be used to coat synthetic and natural rubber gloves on-line. A 1% solution of the polymer in 30/70 ethanol/water can be mixed with 50% Purmol A, 0.5% Armeen D, 1% Silicone 2128, and 1% Darvan L, based on polymer solids. Latex rubber gloves can be dipped into the solution, allowed to dry at room temperature and heated at 85° C. for about ten minutes. The coated gloves had improved donnability. The polymers can be used to coat uncured synthetic and natural latex rubber gloves on-line due to solubility of the polymer in water. The gloves have excellent damp, dry and wet donnability and low blocking properties.

Example 78

To 728 grams of polyoxyethylene diol (PED) having a number average molecular weight of 8000 was added 45 grams of polydimethylsiloxane polyoxyethylenecopolymer having a number average molecular weight of about 780 and 55 grams of polyoxyethylene diol (PED) having a number average molecular weight of 1450. The mixture was heated under vacuum, analyzed for water, and water was added to bring the total to 2.27 gram. Then, 78 grams of methylene bis(cyclohexyl-4-isocyanate) was added at about 70° C. The ratio of NCO to OH groups was 0.92. To the mixture was added 1.4 cc of stannous octoate. The mixture was allowed to exotherm and then was heated in an oven for one hour at 100° C.

The polymers was cut into strips and granulated. The polymer was insoluble in water. The polymer can be used as high slip coating for rubber goods such as gloves and condoms, medical products and can be used in absorbents, as gels in wound dressings and to prepare skin and face creams, to form shampoos, mousse, and baby rash creams.

The polymer was dissolved at a concentration of 1% with 0.25% of Example 77 in 25/75 ethanol/water. To the solution was added 0.5% Armeen 16D, a hexadecyldimethylamine made by Akzo Nobel, and 25% Purmol 5A based on polymer solids. Nonchlorinated latex rubber gloves were dipped into the solution for about five seconds, and then after twenty minutes at room temperature the gloves were placed in an oven at 80° C. for twenty minutes. The gloves were removed and allowed to cool to room temperature. The gloves had excellent dry, damp and wet donnability.

Example 79

To 398 grams of polyoxyethylene diol (PED) having a number average molecular weight of 8000 was added 11 grams of diethylene glycol. The mixture was heated under vacuum, analyzed for water, and 0.33 gram of water was added to bring the total to 0.39 gram. Then, 46 grams of methylene bis(cyclohexyl-4-isocyanate) was added. The ratio of NCO to OH groups was 0.98. To the mixture at 66° C. was added 0.68 cc of dibutyl tin dilaurate. The mixture was allowed to exotherm and then was heated in an oven for one hour at 100° C.

The polymers was cut into strips and granulated. A 3% solution of the polymer in 60/40 propylene glycol/water had a viscosity of 45,000 cps. The polymer was dissolved at 2% in 95/5 ethanol/water and then further diluted with 95/5 ethanol/water to about 0.5% concentration. The solution can be used to coat silicon chips for use in sorting devices. The polymer can be used as high slip coating for rubber goods such as gloves and condoms, medical products and can be used in absorbents, as gels in wound dressings and to prepare skin and face creams, to form shampoos, mousse, and baby rash creams.

A 1% solution of this polymer was prepared in 95/5 ethanol/water. The solution can be applied to rubber gloves to and aid dry, damp and wet donnability, to razors and strips to aid slip. The polymer was dissolved in 95/5 ethanol/water at 3% concentration of polymer. Then polyester and polytetrafluoroethylene cloth was dipped into the solution for about ten seconds, and then the cloth was removed. After about ten minutes at room temperature, the cloth was heated at 100° C. for 20 minutes. The cloth was removed and the coated cloth was immersed for about thirty minutes in a solution of about 1 mg/ml of tissue plasminagen activator (tPA) in water. The cloth was then placed overnight in an oven at about 35° C. to evaporate the water. The coated cloth can be sterilized with ethylene oxide, and implanted into the carotid arteries of pigs for evaluation. The cloth can be used to suture synthetic, mechanical and animal heart valves to heart muscle and tissue. The polymer made in Example 76 can be coated over the polymer of this example prior to immersion in water. Also, the polymer made in this example can then be coated over both coatings to further modify the biocompatibility, absorption and elution properties of the coating. It is anticipated that the multi-layer coating would have excellent biocompatibility, and allow the tPA to elute from the coating over a period of at least two weeks, more likely at least four weeks. Also, a portion of the long chain tPA remains trapped in the hydrated helices of the polymers.

Example 80

To 239 grams of polyoxyethylene diol having a number average molecular weight of 1450 was added 70 grams of polyoxypropylene diol made under the trademark of Acclaim 2200 and having a number average molecular weight of 2000, 114 grams of polyoxypropylene diol having a number average molecular weight of 1025, 148 grams of polyoxytetramethylene diol having a number average molecular weight of 2000, 182 grams of polyoxytetramethylene diol having a number average molecular weight of 1000, 11 grams of diglycolamine, 102 grams of ethylene glycol and 2.8 grams of water. The mixture was heated with stirring until a homogeneous melt was obtained. Then, 636 grams of methylene bis-cyclohexyl-4-4'-diisocyanate was added. The NCO/OH ratio was 0.95. When the temperature reached about 50° C., 2.7 ml of stannous octoate ($T_9$) was added, and the mass was allowed to exotherm. The mass was heated at 100° C. for about one hour to complete formation of the polymer. The polymer had a water content of 47% and an expansion of 26% after twenty-four hours in water at room temperature. The polymer was granulated and extruded and pressed into plaques for hardness testing. The shore a hardness of dry polymer was 65 and that of wet polymer was 56. The polymer can be blended with hydrophobic elastomers and thermoplastic polymers, and coextruded over rubber products for use as expandable sealants and moldings.

Example 81

To 734 grams of polyoxyethylene diol (PED) having a number average molecular weight of 8000 was added 45 grams of polydimethylsiloxane polyoxyethylenecopolymer having a number average molecular weight of about 780 and 55 grams of polyoxyethylene diol (PED) having a number average molecular weight of 1450. The mixture was heated under vacuum, analyzed for water, and water was added to bring the total to 1.8 gram. Then, 72 grams of methylene bis(cyclohexyl-4-isocyanate) was added at about 68° C. The ratio of NCO to OH groups was 0.92. To the mixture was added 1.4 cc of stannous octoate. The mixture was allowed to exotherm and then was heated in an oven for one hour at 100° C.

The polymers was cut into strips and granulated. The polymer was insoluble in water. The polymer can be used as high slip coating for rubber goods such as gloves and condoms, medical products and can be used in absorbents, as gels in wound dressings and to prepare skin and face creams, to form shampoos, mousse, and baby rash creams.

A 1% solution of the polymer in 30/70 ethanol/water can be mixed with 50% Purmol A, 0.5% Armeen D and 1% Darvan L, based on polymer solids. Latex rubber gloves can be dipped into the solution, allowed to dry at room temperature and heated at 85° C. for about ten minutes. The coated gloves had improved dry and damp donnability. The polymer can be used to coat razors. The polymer of this example can be used to coat synthetic and natural rubber gloves on-line. A 1% solution of the polymer in 30/70 ethanol/water can be mixed with 50% Purmol A, 0.5% Armeen D, 1% Silicone 2128, and 1% Darvan L, based on polymer solids. Latex rubber gloves can be dipped into the solution, allowed to dry at room temperature and heated at 85° C. for about ten minutes. The coated gloves had improved donnability.

The polymer was dissolved at a concentration of 1% with 0.25% of example 77 in 20/80 ethanol/water. To the solution was added 0.10% Darvan L, a surfactant made by Vanderbilt Corporation, and 50% Purmol 5A based on polymer solids. Chlorinated latex rubber gloves were dipped into the solution for about five seconds, and then after fifteen minutes at room temperature the gloves were placed in an oven at 90° C. for six minutes. The gloves were removed and allowed to cool to room temperature. The gloves had excellent dry, damp and wet donnability.

The polymer can be used to coat razors. The polymer of this example can be used to coat synthetic and natural rubber gloves on-line.

Example 82

To 140 grams of polyoxyethylene diol having a number average molecular weight of 1450 was added 41 grams of polyoxypropylene diol made under the trademark of Acclaim 2200 and having a number average molecular weight of 2000, 167 grams of polyoxypropylene diol having a number average molecular weight of 1025, 87 grams of polyoxytetramethylene diol having a number average molecular weight of 2000, 107 grams of polyoxytetramethylene diol having a number average molecular weight of 1000, 52 grams of 1,6-hexane diol and 1.8 grams of water. The mixture was heated with stirring until a homogeneous melt was obtained. Then, 229 grams of methylene bis-cyclohexyl-4-4'-diisocyanate was added. The NCO/OH ratio was 0.95. When the temperature reached about 60° C., 1.5 ml of stannous octoate (Tg) was added, and the mass was allowed to exotherm. The mass was heated at 100° C. for about one hour to complete formation of the polymer. The polymer had a water content of % and an expansion of % after twenty-four hours in water at room temperature. The polymer was granulated and extruded and pressed into plaques for hardness testing. The shore a hardness of dry polymer was and that of wet polymer was . The polymer can be blended with hydrophobic elastomers and thermoplastic polymers, and coextruded over rubber products for use as expandable sealants and moldings.

Example 83

To 143 grams of polyoxyethylene diol having a number average molecular weight of 1450 was added 42 grams of polyoxypropylene diol made under the trademark of Acclaim 2200 and having a number average molecular weight of 2000, 68 grams of polyoxypropylene diol having a number average molecular weight of 1025, 89 grams of polyoxytetramethylene diol having a number average molecular weight of 2000, 108 grams of polyoxytetramethylene diol having a number average molecular weight of 1000, 52 grams of dipropylene glycol and 1.8 grams of water. The mixture was heated with stirring until a homogeneous melt was obtained. Then, 218 grams of methylene bis-cyclohexyl-4'-diisocyanate was added. The NCO/OH ratio was 0.95. When the temperature reached about 60° C., 1.5 ml of stannous octoate ($T_9$) was added, and the mass was allowed to exotherm. The mass was heated at 100° C. for about one hour to complete formation of the polymer. The polymer had a water content of % and an expansion of % after twenty-four hours in water at room temperature. The polymer was granulated and extruded and pressed into plaques for hardness testing. The shore a hardness of dry polymer was and that of wet polymer was. The polymer can be blended with hydrophobic elastomers and thermoplastic polymers, and coextruded over rubber products for use as expandable sealants and moldings.

Example 84

To 803 grams of polyoxyethylene diol (PED) having a number average molecular weight of 8000 was added 9.9 grams of polyetherpolycarbonate diol made by Nippoloy America under the tradename of NiP 981 and having a molecular weight of about 1000, and 57 grams of polyoxyethylene diol (PED) having a number average molecular weight of 1450. The mixture was heated under vacuum, analyzed for water, and water was added to bring the total to 0.22 gram. Then, 38 grams of methylene bis(cyclohexyl-4-isocyanate) was added at about 70° C. The ratio of NCO to OH groups was 0.88. To the mixture was added 1.4 cc of stannous octoate. The mixture was allowed to exotherm and then was heated in an oven for one hour at 100° C.

The polymers was cut into strips and granulated. The polymer had a viscosity of 5700 cps in water. The polymer can be used as high slip coating for rubber goods such as gloves and condoms, medical products and can be used in absorbents, as gels in wound dressings and to prepare skin and face creams, to form shampoos, mousse, and baby rash creams.

A 2% solution of the polymer in 30/70 ethanol/water can be mixed with 25% Purmol A, based on polymer solids. Latex rubber gloves can be dipped into the solution, allowed to dry at room temperature and heated at 85° C. for about ten minutes. The coated gloves are lubricious with wet hands.

The polymer was dissolved in a solution of 35% propylene glycol, 37% water, 3% polymer, and about 25% aluminum chorohydrate. The polymer extended the perior during which fragrance was detected from the film.

Example 85

To 809 grams of polyoxyethylene diol (PED) having a number average molecular weight of 8000 was added 45 grams of polydimethylsiloxane polyoxyethylenecopolymer having a number average molecular weight of about 800. The mixture was heated under vacuum, analyzed for water, and water was added to bring the total to 0.91 gram. Then, 52 grams of methylene bis(cyclohexyl-4-isocyanate) was added at about 67° C. The ratio of NCO to OH groups was 0.92. To the mixture was added 1.4 cc of stannous octoate. The mixture was allowed to exotherm and then was heated in an oven for one hour at 100° C.

The polymers was cut into strips and granulated. The polymer was dissolved in water and had a viscosity of 1300 cps at 2% concentration. The polymer had a viscosity 9f 100 cps at 3% concentration in 60/40 propylene glycol/water. The polymer can be used as a high slip coating for rubber goods such as gloves and condoms, medical products and can be used in absorbents, as gels in wound dressings and to prepare skin and face creams, to form shampoos, mousse, and baby rash creams.

A 1% solution of the polymer in 30/70 ethanol/water can be mixed with 50% Purmol A, 0.5% Armeen D and 1% Darvan L, based on polymer solids. Latex rubber gloves can be dipped into the solution, allowed to dry at room temperature and heated at 85° C. for about ten minutes. The coated gloves had improved dry and damp donnability. The polymer can be used to coat razors. The polymer of this example can be used to coat synthetic and natural rubber gloves on-line.

Example 86

To 813 grams of polyoxyethylene diol (PED) having a number average molecular weight of 8000 was added 45 grams of polydimethylsiloxane polyoxyethylenecopolymer having a number average molecular weight of about 2440. The mixture was heated under vacuum, analyzed for water, and water was added to bring the total to 1.4 gram. Then, 48 grams of methylene bis(cyclohexyl-4-isocyanate) was added at about 68° C. The ratio of NCO to OH groups was 0.92. To the mixture was added 1.4 cc of dibutyl tin dilaurate. The mixture was allowed to exotherm and then was heated in an oven for one hour at 100° C.

The polymers was cut into strips and granulated. The polymer can be used as high slip coating for rubber goods such as gloves and condoms, medical products and can be used in absorbents, as gels in wound dressings and to prepare skin and face creams, to form shampoos, mousse, and baby rash creams.

A 1% solution of the polymer in 30/70 ethanol/water can be mixed with 50% Purmol A, 0.5% Armeen D and 1% Darvan L, based on polymer solids. Latex rubber gloves can be dipped into the solution, allowed to dry at room temperature and heated at 85° C. for about ten minutes. The coated gloves had improved dry and damp donnability. The polymer can be used to coat razors. The polymer of this example can be used to coat synthetic and natural rubber gloves on-line.

It is to be understood that the above-described embodiments are illustrative of only a few of the many possible specific embodiments which can represent applications of the principles of the invention. Numerous and varied other arrangements can be readily devised in accordance with these principles by those skilled in the art without departing from the spirit and scope of the invention.

We claim:

1. An article of manufacture comprising:
   a substrate carrying a layer of an amphiphilic polyether polyurethane, said polyurethane comprising the reaction product of a mixture of:
   a hydrophilic diol of polyoxyethlene diol having a number average molecular weight of about 400 to about 20,000, the amount by weight of the hydrophilic diol in the reaction mixture being from about 1% to about 40%;
   a hydrophobic diol of a polyether polycarbonate diol having a number average molecular weight of about 1,000 to about 2,400, and optionally one or more hydrophobic diols selected from the group consisting of polyoxytetramethylene diol having a number average molecular weight of from about 400 to about 3,000, polyoxypropylene diol having a number average molecular weight of from about 400 to about 3,000, polybutylene oxide having a number average molecular weight of about 1,000 to about 2,200, and a polydimethylsiloxane polyoxyalkylene copolymer having a number average molecular weight of about 500 to about 3,800, wherein the polyoxyalkylene is selected from the group consisting of polyoxyethylene and polyoxypropylene, the amount by weight of the hydrophobic diol in the reaction mixture being from about 5% to about 70%;
   an alkylene glycol selected from the group consisting of ethylene glycol, propylene glycol, 2-ethyl-1,3-hexanediol, tripropylene glycol, triethylene glycol, 2,4-pentane diol, 2methyl-1,3-propanediol, 2,-methyl-1,3-pentanediol, cyclohexanediol, diethylene glycol, cyclohexanedimethanol, dipropylene glycol, and mixtures thereof,
   an organic diisocyanate; and
   water in an amount by weight of about 0.10% to about 0.50% of the reaction mixture, the ratio of NCO to OH of the diols, the alkylene glycol and the water being from about 0.90 to about 0.99, and
   an active agent added to said polyurethane, said active agent selected from a pharmacologically active agent, antithrombogenic agent, anticancer agent, cellular growth agent and anticoagulant agent,
   wherein said active agent is entrapped for a period of time in said polyurethane.

2. The article of manufacture of claim 1 wherein the substrate is selected from the group consisting of an elastomer, plastic, woven cloth, nonwoven cloth and metal.

3. The article of manufacture of claim 2 wherein the substrate is selected from polypropylene, latex rubber, polystyrene, polyurethane, polyester, polyethylene, polytetrafluoroethylene, acrylic and silk.

4. A body implant comprising the article of manufacture of claim 1 selected from a suture, venous graft, vascular graft, arterial graft, synthetic vein and synthetic artery.

5. The body implant of claim 4 comprising an antithrombogenic agent selected from the group consisting of prostaglandin, urokinase, streptokinase, tissue plasminogen activator and heparinoid.

6. An article of manufacture comprising:
   a substrate carrying a first layer of a hydrophilic polyether polyurethane, said polyurethane comprising the reaction product of a hydrophilic diol of at least about 60% by weight of the reaction mixture of polyoxyethylene diol having a number average molecular weight of from about 400 to about 20,000;

a catalyst:

an organic diisocyanate; and water in an amount by weight of from about 0.03% to about 0.45% of the reaction mixture, the ratio of NCO to OH of the diols, and water being from about 0.88 to about 0.99; and an active agent added to said polyurethane, said active agent selected from a pharmacologically active agent, an antithrombogenic agent, anticancer agent, cellular growth agent and an anticoagulant agent, wherein said active agent is entrapped for a period of time in said polyurethane.

7. The article of manufacture of claim 6 further comprising:

an alkylene glycol selected from ethylene glycol, propylene glycol, 2-ethyl-1,3-hexane diol, tripropylene glycol, triethylene glycol, 2,-4-pentane diol, 2-methyl-1,3-propanediol, cyclohexanediol, cyclohexanedimethanol, dipropylene glycol, and diethylene glycol, and mixtures thereof in an amount of about 0.05% to about 5.0% by weight of the reaction mixture.

8. The article of manufacture of claim 6 wherein the polyoxyethylene is present in an amount of at least 80% by weight of the reaction mixture.

9. The article of manufacture of claim 6 wherein the substrate is selected from the group consisting of an elastomer, plastic, woven cloth, nonwoven cloth and metal.

10. The article of manufacture of claim 9 wherein the non-woven cloth is formed of polypropylene, polyester, polyethylene, polytetrafluoroethylene, acrylic and silk.

11. A body implant comprising the article of manfacture of claim 9 selected from a suture, venous graft, vascular graft, arterial graft, synthetic vein and synthetic artery.

12. The body implant of claim 6 comprising an antithrobomogenic agent selected from the group consisting of prostaglandin, urokinase, streptokinase, tissue plasminogen activator and heparinoid.

13. An article of manufacture formed of a coating of an amphiphilic polyurethane comprising a reaction product of a hydrophilic diol of polyoxyethylene diol having a number average molecular weight of about 4,000 to about 20,000 in an amount of about 45% to about 96% by weight of the reaction mixture and polyoxyethylene diol having a number average molecular weight of about 600 to about 2,000 in an amount of about 2.0% to about 10% by weight of the reaction mixture;

hydrophobic polyoxyalkylene diol selected from at least one hydrophobic diol selected from the group consisting of polyoxytetramethylene diol having a number average molecular weight of from about 600 to about 3,000 polyoxypropylene diol having a number average molecular weight of from about 400 to about 2,500, a polyether polycarbonate diol having a number average molecular weight of about 1,000 to about 2,000, and a polydimethysiloxane polyoxyalkylene copolymer having a number average molecular weight of about 500 to about 3,000, the amount by weight of the hydrophobic diol in the reaction mixture being from about 0.5% to about 10; and water in an amount by weight of about 0.005% to about 0.30% of the reaction mixture, the ratio of NCO to OH of the diol and water by about 0.80 to about 0.99.

14. The article of manufacture of claim 13 wherein the substrate is an elastomer.

15. The article of manufacture of claim 14 wherein the substrate is a glove.

16. The article of manufacture of claim 1 which is a catheter, infusion therapy catheter, midline catheter, intravenous catheter, cardiovascular catheter, stent, port, dilator or dialysis catheter.

17. An article of manufacture comprising:

a substrate carrying a layer of an amphiphilic polyether polyurethane, said polyurethane comprising the reaction product of a mixture of:

a hydrophilic diol of polyoxvethlene diol having a number average molecular weight of about 400 to about 20,000, the amount by weight of the hydrophilic diol in the reaction mixture being from about 1% to about 40%;

at least one hydrophobic diol selected from the group consisting of polyoxytetramethylene diol having a number average molecular weight of from about 400 to about 3,000, polyoxypropylene diol having a number average molecular weight of from about 400 to about 3,000, polyether polycarbonate diol having a number average molecular weight of about 1,000 to about 2,400, polybutylene oxide having a number average molecular weight of about 1,000 to about 2,200, and polydimethylsiloxane polyoxyalkylene copolymer having a number average molecular weight of about 500 to about 3,800, wherein the polyoxyalkelene is selected from the group consisting of polyoxyethylene and polyoxypropylene, the amount by weight of the hydrophobic diol in the reaction mixture being from about 5% to about 70%;

an alkylene glycol selected from the group consisting of ethylene glycol, propylene glycol, 2-ethyl-1,3-hexanediol, tripropylene glycol, triethylene glycol, 2,-4-pentane diol, 2-methyl-1,3-propanediol, 2,-methyl-1,3-pentanediol, cyclohexanediol, diethylene glycol, cyclohexanedimethanol, dipropylene glycol, and mixtures thereof, an organic diisocyanate; and water in an amount by weight of about 0.10% to about 0.50% of the reaction mixture, the ratio of NCO to OH of the diols, the alkylene glycol and the water being from about 0.90 to about 0.99, and an active agent added to said polyurethane, said active agent selected from a pharmacologically active agent, antithrombogenic agent, anticancer agent, cellular growth agent and anticoagulant agent, wherein said active agent is entrapped for a period of time in said polyurethane;

a second layer coated over said first layer said second layer comprising: a hydrophilic diol of at least about 60% by weight of the reaction mixture of polyoxyethylene having a number average molecular weight of from about 400 to about 20,000;

a catalyst;

an organic diisocyanate; and water in an amount by weight of from about 0.03% to about 0.45% of the reaction mixture, the ratio of NCO to OH of the diols, and water being from about 0.88 to about 0.99.

18. The article of manufacture of claim 2 wherein said plastic is pre-treated with plasma energy and oxidative gases.

19. The article of manufacture of claim 6 wherein said reaction product further comprises a hydrophobic diol in an amount of about 0.1% to about 15% of the reaction mixture, said hydrophobic diol selected from at least one of the following polyoxypropylene diol having a number average molecular weight of about 200 to about 4,000, polyoxytetramethylene diol having a number average molecular weight of about 200 to about 4,000, polyetherpolycarbonate diol having a number average molecular weight of about 1,000 to about 2,200, polydimethylsiloxane polyoxyethylene copolymer diol having a number average molecular weight of about 500 to about 3,000, or polybutylene oxide having a number average molecular weight of about 1,000 to about 3,000.

20. The article of manufacture of claim 6 wherein said catalyst is selected from dibutyl tin dilaurate, stanous octoacte, bismuth neodecante and bismuth octoate.

21. The article of manufacture of claim 6 wherein the substrate is selected from polyurethane, chlorinated elastomer, non-chlorinated elastomer, latex rubber, silicone rubber, acrylonitrile methacrylic acid terpolymer, butadiene styrene copolymer, polyvinyl chloride, and polstrene.

22. An article of manufacture comprising: a substrate carrying a first layer of an amphiphilic polyether polyurethane, said polyurethane comprising the reaction product of a hydrophilic diol of at least about 60% by weight of the reaction mixture of polyoxyethylene diol having a number average molecular weight of from about 400 to about 20,000;

a catalyst;

an organic diisoyanate;

water in an amount by weight of from about 0.03% to about 0.45% of the reaction mixture, the ratio of NCO to OH of the diols, and water being from about 0.88 to about 0.99; and an active agent added to said polyurethane, said active agent selected from a pharmacologically active agent, an antithrombogenic agent, anticancer agent, cellular growth agent and an anticoagulant agent, said active agent is entrapped for a period of time in said polyurethane; and a second layer coated over said first layer said second layer comprising a polyurethane comprising the reaction product of:

a hydrophilic diol of polyoxyethlene diol having a number average molecular weight of about 400 to about 20,000, the amount by weight of the hydrophilic diol in the reaction mixture being from about 1% to about 40%;

at least one hydrophobic diol selected from the group consisting of polyoxytetramethylene diol having a number average molecular weight of from about 400 to about 3,000, polyoxypropylene diol having a number average molecular weight of from about 400 to about 3,000, a polyether polycarbonate diol having a number average molecular weight of about 1,000 to about 2,400, and a polydimethylsiloxane polyoxyalkylene copolymer having a number average molecular weight of about 500 to about 3,800, wherein the polyoxyalklene is selected from the group consisting of polyoxyethylene and polyoxypropylene the amount by weight of the hydrophobic diol in the reaction mixture being from about 5% to about 70%;

an alkylene glycol selected from the group consisting of ethylene glycol, propylene glycol, 2-ethyl-1,3-hexanediol, tripropylene glycol, triethylene glycol, 2,-4-pentane diol, 2methyl-1,3-propanediol, 2,-methyl-1,3-pentanediol, cyclohexanediol, diethylene glycol, cyclohexanedimethanol, dipropylene glycol, and mixtures thereof, an organic diisocyanate; and water in an amount by weight of about 0.10% to about 0.50% of the reaction mixture, the ratio of NCO to OH of the diols, the alkylene glycol and the water being from about 0.90 to about 0.99.

23. The article of manufacture of claim 9 wherein said plastic is pre-treated with plasma energy and oxidative gases.

24. A coating formed of a hydrophilic polyether polyurethane, said polyurethane comprising the reaction product of a hydrophilic diol of at least 60% by weight of the reaction mire of polyoxyethylene diol having a number average molecular weight of from about 400 to about 20,000;

a catalyst;

an organic diisocyanate; and water in an amount by weight of from about 0.03% to about 0.45% of the reaction mixture, the ratio of NCO to OH of the diols, and water being from about 0.88 to about 0.99; and an active agent added to said polyurethane, said active agent selected from a pharmacologically active agent, an antithrombogenic agent, anticancer agent, cellular growth agent and an anticoagulant agent, wherein said active agent is entrapped for a period of time in said polyurethane.

25. The coating of claim 24 further comprising:

an alkylene glycol selected from ethylene glycol, propylene glycol, 2-ethyl-1,3-hexane diol, tripropylene glycol, triethylene glycol, 2,4-pentane diol, 2-methyl-1,3-propanediol, cyclohexanediol, cyclohexanedimethanol, dipropylene glycol, and diethylene glycol, and mixtures thereof in an amount of about 0.05% to about 5.0% by weight of the reaction mixture.

26. The coating of claim 24 wherein said coating is applied to a substrate selected from metal, glass, elastomer, plastic, polyurethane, chlorinated elastomer, nonchlorinated elastomer, latex rubber, silicone rubber, butadiene acrylonitrile methacrylic, acid terpolymer, butadiene styrene copolymer, polyvinyl chloride or polstrene.

27. The article of manufacture of claim 26 wherein said plastic is pre-treated with plasma energy and oxidative gases.

28. A coating formed of a first layer of an amphiphilic polyether polyurethane, said polyurethane comprising the reaction product of a hydrophilic diol of at least 60% by weight of the reaction mixture of polyoxyethylene diol having a number average molecular weight of from about 400 to about 20,000;

a catalyst;

an organic diisocyanate;

water in an amount by weight of from about 0.03% to about 0.45% of the reaction mixture, the ratio of NCO to OH of the diols, and water being from about 0.88 to about 0.99; and an active agent added to said polyurethane, said active agent selected from a pharmacologically active agent, an antithrombogenic agent, anticancer agent, cellular growth agent and an anticoagulant agent, wherein said active agent is entrapped for a period of time in said polyurethane; and a second layer coated over said first layer said second layer comprising a polyurethane comprising the reaction product of:

a hydrophilic diol of polyoxyethlene diol having a number average molecular weight of about 400 to about 20,000, the amount by weight of the hydrophilic diol in the reaction mixture being from about 1% to about 40%;

at least one hydrophobic diol selected from the group consisting of polyoxytetramethylene diol having a number average molecular weight of from about 400 to about 3,000, polyoxypropylene diol having a number average molecular weight of from about 400 to about 3,000, a polyether polycarbonate diol having a number average molecular weight of about 1,000 to about 2,400, and a polydimethylsiloxane polyoxyalkylene copolymer having a number average molecular weight of about 500 to about 3,800, wherein the polyoxyalkylene is selected from the group consisting of polyoxyethylene and polyoxypropylene, the amount by weight of the hydrophobic diol in the reaction mixture being from about 5% to about 70%;

an alkylene glycol selected from the group consisting of ethylene glycol, propylene glycol, 2-ethyl-1,3-hexanediol, tripropylene glycol, triethylene glycol, 2,-4-pentane diol, 2methyl-1,3-propanediol, 2,-methyl-1,3-pentanediol, cyclohexanediol, diethylene glycol, cyclohexanedimethanol, dipropylene glycol, and mixtures thereof, an organic diisocyanate; and water in an amount by weight of about 0.10% to about 0.50% of the reaction mixture, the ratio of NCO to OH of the diols, the alkylene glycol and the water being from about 0.90 to about 0.99.

29. A coating formed of an amphiphilic polyurethane, said polyurethane comprising a reaction product of a hydrophilic diol of polyoxyethylene diol having a number average molecular weight of about 3,000 to about 20,000 in an amount by weight of about 50% to about 85% of the reaction mixture and a polyoxyethylene diol having a number average molecular weight of about 200 to about 2,000 in an amount of about 0.1% to about 25% by weight of the reaction mixture; and at least one hydrophobic polyoxyalkylene diol selected from the group consisting of polyoxypropylene having a number average molecular weight of about 400 to about 3000, a polyoxytetramethylene diol having a number average molecular weight of about 400 to about 3000, a polyether polycarbonate diol having a number average molecular weight of about 1000 to about 3000 polybutylene oxide having a number average molecular weight of about 200 to about 3000, a polydimethylsiloxane polyoxyalkylene copolymer having a number average molecular weight of about 500 to about 3200 wherein the polyoxyalkylene is selected from polyoxyethylene and polyoxypropylene, the amount by weight of the hydrophobic diol in the reaction mixture being from about 0.1% to about 30% by weight of the reaction mixture;

organic diisocyanate; and water in an amount by weight of the reaction mixture of about 0.005% to about 0.30% in an equivalent mole weight ratio of NCO to OH of the diols, from about 0.85 to about 0.99.

30. The coating of claim 29 wherein the amount by weight of polydimethylsiloxane polyoxyethylene copolymer used in the reaction mixture is about 0.1% to about 25% and the amount of water in the reaction mixture is about 0.01% to about 0.20%.

31. The coating of claim 29 wherein the polyether polycarbonate diol is present in an amount by weight of the reaction mixture of about 0.1% to about 15% and the amount by weight of the water in the reaction mixture is about 0.015% to about 0.15%.

* * * * *